(12) United States Patent
Fiorina et al.

(10) Patent No.: US 12,221,476 B2
(45) Date of Patent: Feb. 11, 2025

(54) ANTIBODIES AND USES THEREOF

(71) Applicants: OSPEDALE SAN RAFFAELE S.R.L., Milan (IT); ENTHERA S.R.L., Milan (IT)

(72) Inventors: Paolo Fiorina, Boston, MA (US); Francesca D'Addio, Milan (IT); Francesca Zagari, Milan (IT)

(73) Assignees: OSPEDALE SAN RAFFAELE S.R.L., Milan (IT); ENTHERA S.R.L., Milan (IT)

( * ) Notice: Subject to any disclaimer, the term of this patent is extended or adjusted under 35 U.S.C. 154(b) by 947 days.

(21) Appl. No.: 17/281,874

(22) PCT Filed: Oct. 2, 2019

(86) PCT No.: PCT/EP2019/076771
§ 371 (c)(1),
(2) Date: Mar. 31, 2021

(87) PCT Pub. No.: WO2020/070224
PCT Pub. Date: Apr. 9, 2020

(65) Prior Publication Data
US 2021/0388072 A1 Dec. 16, 2021

(30) Foreign Application Priority Data
Oct. 2, 2018 (EP) .................................... 18198252

(51) Int. Cl.
*C07K 16/22* (2006.01)
*A61K 39/00* (2006.01)

(52) U.S. Cl.
CPC ........ *C07K 16/22* (2013.01); *A61K 2039/505* (2013.01); *C07K 2317/21* (2013.01); *C07K 2317/24* (2013.01); *C07K 2317/33* (2013.01); *C07K 2317/76* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 3,773,919 A | 11/1973 | Boswell et al. | |
| 5,215,534 A | 6/1993 | De Harde et al. | |
| 6,066,464 A | 5/2000 | Khosravi et al. | |
| 6,428,781 B1 | 8/2002 | Sakano et al. | |
| 6,602,684 B1 | 8/2003 | Umana et al. | |
| 7,083,784 B2 | 8/2006 | Dall'Acqua et al. | |
| 7,521,541 B2 | 4/2009 | Eigenbrot et al. | |
| 8,101,396 B2 | 1/2012 | Sabbadini et al. | |
| 8,323,962 B2 | 12/2012 | Dall'Acqua et al. | |
| 9,248,242 B2 | 2/2016 | Verespej et al. | |
| 9,427,531 B2 | 8/2016 | Hourmand et al. | |
| 9,566,395 B2 | 2/2017 | Denny et al. | |
| 10,682,391 B2 | 6/2020 | D'Addio et al. | |
| 11,020,453 B2 | 6/2021 | D'Addio et al. | |
| 11,786,585 B2 | 10/2023 | Oh et al. | |
| 2003/0157108 A1 | 8/2003 | Presta | |
| 2004/0093621 A1 | 5/2004 | Shitara et al. | |
| 2004/0132028 A1 | 7/2004 | Stumpp et al. | |
| 2005/0123546 A1 | 6/2005 | Umana et al. | |
| 2015/0044209 A1 | 2/2015 | Brodt et al. | |
| 2018/0169184 A1 | 6/2018 | D'Addio et al. | |
| 2018/0172708 A1 | 6/2018 | D'Addio et al. | |
| 2018/0243367 A1 | 8/2018 | D'Addio et al. | |
| 2020/0316168 A1 | 10/2020 | D'Addio et al. | |
| 2021/0169973 A1 | 6/2021 | D'Addio et al. | |
| 2023/0039165 A1 | 2/2023 | Amabile et al. | |
| 2023/0192827 A1 | 6/2023 | Amabile et al. | |
| 2023/0242649 A1 | 8/2023 | Fiorina et al. | |

FOREIGN PATENT DOCUMENTS

| | | |
|---|---|---|
| CN | 105504058 A | 4/2016 |
| CN | 107921094 A | 4/2018 |
| CN | 107921132 A | 4/2018 |
| EP | 0965596 A1 | 12/1999 |
| EP | 3632929 A1 | 4/2020 |
| JP | 2018-516975 A | 6/2018 |
| JP | 2018-520212 A | 7/2018 |
| WO | WO 1997/030087 A1 | 8/1997 |
| WO | WO 1997/039032 A1 | 10/1997 |
| WO | WO 98/029451 A1 | 7/1998 |
| WO | WO 1998/058964 A1 | 12/1998 |
| WO | WO 1999/022764 A1 | 5/1999 |
| WO | WO 1999/046597 A1 | 9/1999 |
| WO | WO 2001/053837 A1 | 7/2001 |
| WO | WO 01/87238 A2 | 11/2001 |
| WO | WO 2002/020565 A2 | 3/2002 |

(Continued)

OTHER PUBLICATIONS

PCT International Search Report and Written Opinion, International Application No. PCT/EP2019/076771, dated Mar. 16, 2020, 28 Pages.

Ingermann, A.R. et al, "Identification of a Novel Cell Death Receptor Mediating IGFBP-3-induced Anti-tumor Effects in Breast and Prostate Cancer," Journal of Biological Chemistry, 2010, vol. 285, No. 39, pp. 30233-30246.

Flynn, R.S., et al., "Endogenous IGFBP-3 Regulates Excess Collagen Expression in Intestinal Smooth Muscle Cells of Crohn's Disease Strictures," Inflammatory Bowel Diseases, 2011, vol. 11, No. 1, pp. 193-201.

Lui, J.C., et al., "EZH1 and EZH2 promote skeletal growth by repressing inhibitors of chondrocyte proliferation and hypertrophy," Nature Communications, 2016, vol. 7, No. 1, pp. 13685-13685.

(Continued)

*Primary Examiner* — Elizabeth C. Kemmerer
(74) *Attorney, Agent, or Firm* — Fenwick & West LLP

(57) ABSTRACT

The present invention relates to an antibody or antigen binding fragment thereof that binds specifically to IGFBP3 and does not displace the binding of IGF-I to IGFBP3. The antibody inhibits or reduces the binding of IGFBP3 to the TMEM219 receptor. The invention also relates to methods for their production, pharmaceutical compositions containing said antibodies, and uses thereof.

22 Claims, 18 Drawing Sheets
Specification includes a Sequence Listing.

(56) References Cited

FOREIGN PATENT DOCUMENTS

| | | | |
|---|---|---|---|
| WO | WO 2002/034916 A2 | 5/2002 |
| WO | WO 2003/011878 A2 | 2/2003 |
| WO | WO 2016/113880 A2 | 10/2006 |
| WO | WO 2007/024715 A2 | 3/2007 |
| WO | WO 2008/153788 A2 | 12/2008 |
| WO | WO 2011/133886 A2 | 10/2011 |
| WO | WO 2012/113900 A1 | 8/2012 |
| WO | WO 2013/152989 A2 | 10/2013 |
| WO | WO 2014/089262 A1 | 6/2014 |
| WO | WO 2016/062792 A1 | 4/2016 |
| WO | WO 2016/193496 A1 | 12/2016 |
| WO | WO 2016/193497 A1 | 12/2016 |
| WO | WO 2019/099706 A1 | 5/2019 |
| WO | WO 2020/070224 A1 | 4/2020 |
| WO | WO 2021/094620 A1 | 5/2021 |
| WO | WO 2021/099574 A1 | 5/2021 |
| WO | WO 2021/165499 A1 | 8/2021 |

OTHER PUBLICATIONS

D'Addio, F., et al., "Circulating IGF-I and IGFBP3 Levels Control Human Colonic Stem Cell Function and Are Disrupted in Diabetic Enteropathy," Cell Stem Cell, 2015, vol. 17, No. 4, pp. 486-498.

International Search Report and Written Opinion, Patent Cooperation Treaty Application No. PCT/EP2021/054215, dated Apr. 19, 2021, 11 pages.

Kim, KS, et al., "Induction of Cellular Senescence by Insulin-like Growth Factor Binding Protein-5 through a p53-dependent Mechanism," *Molecular Biology of the Cell*, vol. 18, No. 11, DOI:10.2091/MBC.E07-03-0280, Sep. 2007, p. 4543-4552, Retrieved from the Internet:URL:https://www.ncbi.nlm.nih.gov/pmc/articles/PMC2043568/pdf/zmk4543.pdf, Abstract, p. 4545, right-hand column last paragraph through p. 4547, left-hand column, 1st paragraph, figures 1 and 2, p. 4549, left-hand column, last paragraph through right-hand column, 1st paragraph.

Lecca, M.R., et al., "Fibrotic response in fibroblasts from congenital disorders of glycosylation," *Journal of Cellular and Molecular Medicine*, vol. 15, Issue 8, Aug. 2011, p. 1788-1796, Abstract, p. 1789, right-hand column, last paragraph, figure 3, p. 1794, left-hand column, 1st paragraph through right-hand column, 1st paragraph.

Melone, M.A.B., et al., "Increased expression of IGF-binding protein-5 in Duchenne muscular dystrophy (DMD) fibroblasts correlates with the fibroblast induced downregulation of DMD myoblast growth: an in vitro analysis," *Journal of Cellular Physiology, Wiley Subscription Services, Inc, US*, vol. 185, Jan. 2000, p. 143-153, abstract, p. 145, last paragraph, p. 136, 2nd paragraph, p. 148, left-hand column 1st paragraph through p. 149, right-hand column, 1st paragraph.

United States Office Action, U.S. Appl. No. 17/174,893, filed Sep. 20, 2023, 14 pages.

Wright, C.S., et al., "Cell motility in models of wounded human skin is improved by Gap27 despite raised glucose, insulin and IGFBP-5," *Experimental Cell Research*, vol. 319, Issue 4, Feb. 15, 2013, , p. 390-401, DOI: 10.1016/j.yexcr.2012.12.013, ISSN:0014-4827, Abstract, p. 391, left-hand column, paragraph 2; p. 393, right-hand column, paragraph 2, figure 2, figure 3, p. 398, right-hand column, paragraph 3.

International Search Report and Written Opinion, Patent Cooperation Treaty Application No. PCT/EP2020/082292, Mar. 29, 2021, 17 pages.

Abdiche, Y.N. et al., "Exploring blocking assays using Octet, ProteOn, and Biacore biosensors," Analytical Biochemistry, Mar. 2009, vol. 386, No. 2, pp. 172-180.

Alper, C.A. et al., "Incomplete penetrance of susceptibility genes for MHC-determined immunoglobin deficiencies in monozygotic twins discordant for type 1 diabetes," Journal of Autoimmunity, 2006, vol. 27, pp. 89-95.

Angal, S. et al., "A single amino acid substitution abolishes the heterogeneity of chimeric mouse/human (IgG4) antibody," Molecular Immunology, 1993, vol. 30, No. 1, pp. 105-108.

Atkinson, M.A. et al., "Current concepts on the pathogenesis of type 1 diabetes—considerations for attempts to prevent and reverse the disease," Diabetes Care, 2015, vol. 38, pp. 979-988.

Atkinson, M.A. et al., "Does the gut microbiata have a role in type 1 diabetes? Early evidence from humans and animal models of the disease," Diabetologia, 2012, vol. 55, pp. 2868-2877.

Atkinson, M.A. et al., "Type 1 diabetes," Lancet, 2013, vol. 383, pp. 69-82.

Barker, N., "Adult intestinal stem cells: critical drivers of epithelial homeostasis and regeneration," Nat Rev Mol Cell Biol, 2014, vol. 15, pp. 19-33.

Bartfeld, S. et al., "In Vitro Expansion of Human Gastric Epithelial Stem Cells and Their Responses to Bacterial Infection," Gastroenterology, 2015, vol. 148, pp. 126-136.

Baxter, R., "IGF binding proteins in cancer: mechanistic and clinical insights," Nature Reviews, 2014, vol. 14, pp. 329-341.

Baxter, R.C., "Insulin-like growth factor binding protein-3 (IGFBP-3): Novel ligands mediate unexpected functions," J Cell Commun Signal, 2013, vol. 7, pp. 179-189.

Beck, A. et al., "Strategies and challenges for the next generation of therapeutic antibodies," Nature Reviews Immunology, 2010, vol. 10, pp. 345-352.

Ben Nasr, M. et al., "Co-transplantation of autologous MSCs delays islet allograft rejection and generates a local immunoprivileged site," Acta Diabetologica, 2015, vol. 52, pp. 917-927.

Ben Nasr, M. et al., "The rise, fall, and resurgence of immunotherapy in type 1 diabetes," Pharmacological Research, 2015, vol. 98, pp. 31-38.

Binz, H.K. et al., "Designing Repeat Proteins: Well-expressed, Soluble and Stable Proteins from Combinatorial Libraries of Consensus Ankyrin Repeat Proteins," J Mol Biol, 2003, vol. 332, pp. 489-503.

Bluestone, J.A. et al., "Genetics, pathogenesis and clinical interventions in type 1 diabetes," Nature, 2010, vol. 464, pp. 1293-1300.

Boman, B.M. et al., "Human colon cancer stem cells: a new paradigm in gastrointestinal oncology," Journal of Clinical Oncology, 2008, vol. 26, pp. 2828-2838.

Bondy, C.A. et al., "Clinical uses of insulin-like growth factor I.," Ann Intern Med, 1994, vol. 120, pp. 593-601.

Bortvedt, S.F. et al., "Insulin-like growth factor 1," *Current Opinion in Gastroenterology*, vol. 28, No. 2, Mar. 1, 2012, pp. 89-98.

Boucher, J. et al., "A kinase-independent role for unoccupied insulin and IGF-1 receptors in control of apoptosis," Sci Signal, 2010, vol. 3, pp. ra87.

Breault, D.T. et al., "Generation of mTert-GFP mice as a model to identify and study tissue progenitor cells," Proc Natl Acad Sci, 2008, vol. 105, pp. 10420-10425.

Brennand, K. et al., "Slow and steady is the key to beta-cell replication," Journal of Cellular and Molecular Medicine, 2009, vol. 13, pp. 472-487.

Brooks, B.D., "The Importance of Epitope Binning in Drug Discovery," Current Drug Discovery Technology, 2014, vol. 11, pp. 109-112.

Burgess, W.H. et al., "Possible Dissociation of the Heparin-binding and Mitogenic Activities of Heparin-binding (Acidic Fibroblast) Growth Factor-1 from Its Receptor-binding Activities by Site-directed Mutagenesis of a Single Lysine Residue," The Journal of Cell Biology, Nov. 1990, vol. 111, pp. 2129-2138.

Bytzer, P. et al., "GI symptoms in diabetes mellitus are associated with both poor glycemic control and diabetic complications," Am J Gastroenterol, 2002, vol. 97, pp. 604-611.

Camilleri, M., "Diabetic gastroparesis," N Engl J Med, 2007, vol. 356, pp. 820-829.

Cano, A.E. et al., "Gastrointestinal symptoms in patients with end-stage renal disease undergoing treatment by hemodialysis or peritoneal dialysis," Am J Gastroenterol, 2007, vol. 102, pp. 1990-1997.

Carlone, D.L. et al., "Tales from the crypt: the expanding role of slow cycling intestinal stem cells," Cell Stem Cell, 2012, vol. 10, pp. 2-4.

(56) References Cited

OTHER PUBLICATIONS

Carpentino, J.E. et al., "Aldehyde dehydrogenase-expressing colon stem cells contribute to tumorigenesis in the transition from colitis to cancer," Cancer Res, 2009, vol. 69, pp. 8208-8215.

Carrington, E.V. et al., "Traditional measures of normal anal sphincter function using high-resolution anorectal manometry (HRAM) in 115 healthy volunteers," Neurogastroenterology and Motility: The Official Journal of the European Gastrointestinal Motility Society, 2014, vol. 26, pp. 625-635.

Carvello, M. et al., "Inotuzumab ozogamicin murine analog-mediated B-cell depletion reduces anti-islet allo- and autoimmune responses," Diabetes, 2012, vol. 61, pp. 155-165.

Chothia, C. et al., "Structural repertoire of the human VH segments," Journal of Molecular Biology, 1992, vol. 227, No. 3, pp. 799-817.

Cui, S. et al., "Current understanding concerning intestinal stem cells," World J Gastroenterol, 2016, vol. 22, No. 31, pp. 7099-7110.

D'Addio, F. et al., "Autologous nonmyeloablative hematopoietic stem cell transplantation in new-onset type 1 diabetes: a multicenter analysis," Diabetes, 2014, vol. 63, pp. 3041-3046.

Dall'Acqua, W.F. et al., "Properties of Human IgG1s Engineered for Enhanced Binding to the Neonatal Fc Receptor (FcRn)*," The Journal of Biological Chemistry, 2006, vol. 281, No. 33, pp. 23514-23524.

De Kort, S. et al., "Diabetes mellitus, genetic variants in the insulin-like growth factor pathway and colorectal cancer risk," International Journal of Cancer, 2019, vol. 145, pp. 1774-1781.

De Santi, M. et al., "Use of hormones in doping and cancer risk," Annali di igiene: medicina preventiva e di comunita, 2019, vol. 31, No. 6, pp. 590-594.

Dhingra, A.K. et al., "An update on anti-inflammatory compounds: a review," Anti-Inflammatory & Anti-Allergy Agents in Medicinal Chemistry, 2015, vol. 14, No. 2, pp. 81-97.

Di Cairano, E.S. et al., "The glial glutamate transporter (GLT1) is expressed by pancreatic beta-cells and prevents glutamate-induced beta-cell death," The Journal of Biological Chemistry, 2011, vol. 286, pp. 14007-14018.

D'Mello, S. et al., "Innate Dysfunction Promotes Linear Growth Failure in Pediatric Crohn Disease and Growth Hormone Resistance in Murine Ileitis," Inflammatory Bowel Diseases, 2012, vol. 18, pp. 236-245.

Domenech, A. et al., "Morphofunctional changes underlying intestinal dysmotility in diabetic RIP-I/hIFNbeta transgenic mice," Int J Exp Pathol, 2011, vol. 92, pp. 400-412.

Drogan, D. et al., "Insulin-Like Growth Factor 1 and Insulin-Like Growth Factor-Binding Protein 3 in Relation to the Risk of Type 2 Diabetes Mellitus: Results from the EPIC-Potsdam Study," Am J Epidemiol, 2016, vol. 183, No. 6, pp. 553-560.

Eichele, D.D. et al., "Dextran sodium sulfate colitis murine model: an indispensable tool for advancing our understanding of inflammatory bowel disease pathogenesis," World J Gastroenterol, 2017, vol. 23, No. 33, pp. 6016-6029.

Eisenbarth, G.S., "Type I diabetes mellitus. A chronic autoimmune disease," The New England Journal of Medicine, 1986, vol. 314, pp. 1360-1368.

Faraj, J. et al., "Oesophageal dysmotility, delayed gastric emptying and gastrointestinal symptoms in patients with diabetes mellitus," Diabet Med, 2007, vol. 24, pp. 1235-1239.

Feldman, M. et al., "Disorders of gastrointestinal motility associated with diabetes mellitus," Ann Intern Med, 1983, vol. 98, pp. 378-384.

Filippi, C.M. et al., "Viral trigger for type 1 diabetes: pros and cons," Diabetes, 2008, vol. 57, pp. 2863-2871.

Fiorina, P. et al., "Effects of kidney-pancreas transplantation on atherosclerotic risk factors and endothelial function in patients with uremia and type 1 diabetes," Diabetes, 2001, vol. 50, pp. 496-501.

Fiorina, P. et al., "Long-term beneficial effect of islet transplantation on diabetic macro-/microangiopathy in type 1 diabetic kidney-transplanted patients," Diabetes Care, 2003, vol. 26, pp. 1129-1136.

Fiorina, P. et al., "Natural history of kidney graft survival, hypertrophy, and vascular function in end-stage renal disease type 1 diabetic kidney-transplanted patients: beneficial impact of pancreas and successful islet cotransplantation," Diabetes Care, 2005, vol. 28, pp. 1303-1310.

Fiorina, P. et al., "Normalization of multiple hemostatic abnormalities in uremic type 1 diabetes patients after kidney-pancreas transplantation," Diabetes, 2004, vol. 53, pp. 2291-2300.

Folli, F. et al., "Proteomics reveals novel oxidative and glycolytic mechanisms in type 1 diabetic patients' skin which are normalized by kidney-pancreas transplantation," PLoS One, 2010, vol. 5, pp. e9923.

Forbes, K. et al., "Transforming growth factor-β (TGFβ) receptors I/II differentially regulate TGFβ1 and IGF-binding protein-3 mitogenic effects in the human placenta," Endocrinology, 2010, vol. 151, pp. 1723-1731.

Ge et al., "Generation of Soluble Leptin Receptor by Ectodomain Shedding of Membrane-spanning Receptors in Vitro and in Vivo," *Journal of Biological Chemistry*, vol. 277, Issue 48, Nov. 29, 2002, pp. 45898-45903.

GenBank: AAH17488.1 "TMEM219 protein, partial [*Homo sapiens*]" NCBI, Jun. 16, 2008, 2 Pages, can be retrieved at <URL:https://www.ncbi.nlm.nih.gov/protein/AAH17488>.

George, M.J. et al., Current Treatment Option for Type 2 Diabetes Mellitus in Youth: Today's Realities and Lessons from the TODAY Study, Curr Diab Rep, 2013, vol. 13, No. 1, pp. 72-80.

Gersemann, M. et al., "From intestinal stem cells to inflammatory bowel diseases," World Journal of Gastroenterology, 2011, vol. 17, pp. 3198-3203.

Giustina, A. et al., "Insulin and GH-IGF-I axis: endocrine pacer or endocrine disruptor?" Acta Diabetol, 2014, vol. 52, pp. 433-443.

Goswami, S. et al., "Developments and Challenges for mAb-Based Therapeutics," Antibodies, 2013, vol. 2, pp. 452-500.

Gracz, A.D. et al., "Brief Report: CD24 and CD44 mark human intestinal epithelial cell populations with characteristics of active and facultative stem cells," Stem Cells, 2013, vol. 31, pp. 2024-2030.

Hinton, P.R. et al., "An Engineered Human IgG1 Antibody with Longer Serum Half-Life," The Journal of Immunology, 2006, vol. 176, No. 1, pp. 346-356.

Huch, M. et al., "In vitro expansion of single Lgr5+ liver stem cells induced by Wnt-driven regeneration," Nature, 2013, vol. 494, pp. 247-250.

Hughes, K.R. et al., "Expression profiling of Wnt family of genes in normal and inflammatory bowel disease primary human intestinal myofibroblasts and normal human colonic crypt epithelial cells," Inflamm Bowel Dis, 2011, vol. 17, pp. 213-220.

International Search Report and Written Opinion, Patent Cooperation Treaty Application No. PCT/EP2020/082890, Feb. 22, 2021, thirteen pages.

Jain, V., "Management of Type 1 Diabetes in Children and Adolescents," Indian J Pediatr, 2014, vol. 81, No. 2, pp. 170-177.

Jung, P. et al., "Isolation and in vitro expansion of human colonic stem cells," Nat Med, 2011, vol. 17, pp. 1225-1227.

Kam, N.W.S. et al., "Carbon nanotubes as multifunctional biological transporters and near-infrared agents for selective cancer cell destruction," PNAS, 2005, vol. 102, No. 33, pp. 11600-11605.

Kaplan, G.G., "The global burden of IBD: from 2015 to 2025," Nat Rev Gastroenterol Hepatol, 2015, vol. 12, No. 12, pp. 720-727.

Katsanos, K.H. et al., "Reduced serum insulin-like growth factor-1 (IGF-1) and IGF-binding protein-3 levels in adults with inflammatory bowel disease," Growth Hormone & IGF Research, 2001, vol. 11, pp. 364-367.

Keenan, H.A. et al., "Residual insulin production and pancreatic β-cell turnover after 50 years of diabetes: Joslin Medalist Study," Diabetes, 2010, vol. 59, No. 11, pp. 2846-2853.

Kirman, I. et al., "Insulin-like Growth Factor Binding Protein 3 in Inflammatory Bowel Disease," Digestive Diseases and Sciences, Apr. 2005, vol. 50, No. 4, pp. 780-784.

Kohl, A. et al., "Designed to be stable: Crystal structure of a consensus ankyrin repeat protein," PNAS, 2003, vol. 100, No. 4, pp. 1700-1705.

Kosinksi, C. et al., "Gene expression patterns of human colon tops and basal crypts and BMP antagonists as intestinal stem cell niche

(56) References Cited

OTHER PUBLICATIONS factors," Proceedings of the National Academy of Sciences of the United States of America, 2007, vol. 104, pp. 15418-15423.

Kuemmerle, J.F. et al., "IGFBP-3 actives TFG-β receptors and directly inhibits growth in human intestinal smooth muscle cells," Am J Physiol Gastrointest Liver Physiol, Jun. 3, 2004, vol. 287, pp. G795-G802.

Kundu, P. et al., "An EphB-Abl signaling pathway is associated with intestinal tumor initiation and growth," Science Translational Medicine, 2015, vol. 7, pp. 281ra44.

Lazar, E. et al., "Transforming Growth Factor alpha: mutation of aspartic acid 47 and leucine 48 results in different biological activities," Molecular and Cellular Biology, Mar. 1988, vol. 8, No. 3, pp. 1247-1252.

Le Roith, D., "Seminars in medicine of the Beth Israel Deaconess Medical Center. Insulin-like growth factors," N Engl J Med, 1997, vol. 336, pp. 633-640.

Lin, M.C. et al. "Structure-function relations in glucagon. Properties of highly purified Des-his1-, monoiodo-, and [Des-Asn28, Thr29](homoserine lactone27)-glucagon," Biochemistry, 1975, vol. 14, No. 8, pp. 1559-1563.

Ma, X. et al., "A new mutation in BFSP2 (G1091A) causes autosomal dominant congenital lamellar cataracts," Molecular Vision, 2008, vol. 14, pp. 1906-1911.

Mahe, M.M. et al., "Establishment of gastrointestinal epithelial organoids," Curr Protoc Mouse Biol, 2013, vol. 3, pp. 217-240.

Marsha, J.D., "Lipid Management in Patients with Type 2 Diabetes," Am Health Drug Benefits, 2011, vol. 4, No. 5, pp. 312-322.

McLean, M.H. et al., "Does the microbiota play a role in the pathogenesis of autoimmune diseases?", Gut, 2015, vol. 64, pp. 332-341.

Medema, J.P. et al., "Microenvironmental regulation of stem cells in intestinal homeostasis and cancer," Nature, 2011, vol. 474, pp. 318-326.

Meier, J.J. et al., "Sustained beta cell apoptosis in patients with long-standing type 1 diabetes: indirect evidence for islet regeneration?", Diabetologia, 2005, vol. 48, No. 11, pp. 2221-2228.

Merlos-Suarez, A. et al., "The intestinal stem cell signature identifies colorectal cancer stem cells and predicts disease relapse," Cell Stem Cell, 2011, vol. 8, pp. 511-524.

Mullberg at al., "The soluble interleukin-6 receptor is generated by shedding," *European Journal of Immunology*, vol. 23, Issue 2, Feb. 1993, pp. 473-480.

Munoz, J. et al., "The lgr5 intestinal stem cell signature: robust expression of proposed quiescent '+4' cell markers," EMBO J, 2012, vol. 31, pp. 3079-3091.

Muzumdar, R., et al., "Central and Opposing Effects of IGF-1 and IGF-Binding Protein-3 on Systemic Insulin Action," Diabetes, Oct. 2006, vol. 55, pp. 2788-2796.

Nano, R. et al., "Islet isolation for alltransplantation: variables associated with successful islet yield and graft function," Diabetologia, 2005, vol. 48, pp. 906-912.

Nathan, D.M., "Diabetes: Advances in Diagnosis and Treatment," Jama, 2015, vol. 314, pp. 1052-1062.

Nguyen, K.H. et al., "Human IGF Binding Protein-3 Overexpression Impairs Glucose Regulation in Mice via an Inhibition of Insulin Secretion," Endocrinology, 2011, vol. 152, No. 6, pp. 2184-2196.

Oh, Y. et al., "Antiproliferative actions of insulin-like growth factor binding protein (IGFBP)-3 in human breast cancer cells," Prog Growth Factor Res, 1995, vol. 6, pp. 503-512.

Oilinki, T. et al., "Prevalence and characteristics of diabetes among Somali children and adolescents living in Helsinki, Finland," Pediatric Diabetes, 2012, vol. 13, pp. 176-180.

Pambianco, G. et al. "The 30-year natural history of type 1 diabetes complications: the Pittsburgh Epidemiology of Diabetes Complications Study experience," Diabetes, 2006, vol. 55, pp. 1463-1469.

PCT International Preliminary Report on Patentability Chapter II for PCT/EP2016/062792, May 23, 2017, 10 pages.

PCT International Search Report and Written Opinion, PCT Application No. PCT/EP2016/062790, Sep. 26, 2016, 12 pages.

PCT International Search Report and Written Opinion, PCT Application No. PCT/EP2016/062792, Sep. 30, 2016, 9 pages.

Peet, A. et al., "Circulating IGF1 and IGFBP3 in relation to the development of β-cell autoimmunity in young children," Eur J Endocrinol, 2015, vol. 173, No. 2, pp. 129-137.

Petkova, S.B. et al., "Enhanced half-life of genetically engineered human IgG1 antibodies in a humanized FcRn mouse model: potential application in humorally mediated autoimmune disease," International Immunology, 2006, vol. 18, No. 12, pp. 1759-1769.

Petrelli, A. et al., "IL-21 is an antitolerogenic cytokine of the late-phase alloimmune response," Diabetes, 2011, vol. 60, pp. 3223-3234.

Piscaglia, A.C. et al., "Circulating hematopoietic stem cells and putative intestinal stem cells in coeliac disease," Journal of Translational Medicine, 2015, vol. 13, pp. 220.

Pithadia, A.B. et al., "Treatment of inflammatory bowel disease (IBD)" Pharmacological Reports, 2011, vol. 63, pp. 629-642.

Pupim, L.B. et al., "Accelerated lean body mass loss in incident chronic dialysis patients with diabetes mellitus," Kidney Int, 2005, vol. 68, pp. 2368-2374.

Remes-Troche, J.M., et al., "Rectoanal reflexes and sensorimotor response in rectal hyposensitivity," Diseases of the Colon and Rectum, 2010, vol. 53, pp. 1047-1054.

Sato, T. et al., "Growing self-organizing mini-guts from a single intestinal stem cell: mechanism and applications," Science, 2013, vol. 340, pp. 1190-1194.

Schonhoff, S.E. et al., "Minireview: Development and Differentiation of Gut Endocrine Cells," Endocrinology, 2004, vol. 145, pp. 2639-2644.

Schwartz, G.P. et al., "A superactive insulin: [B10 Aspartic acid]insulin(human)," Proc Natl Acad Sci, Sep. 1987, vol. 84, pp. 6408-6411.

Schwarz, P.E. et al., "Nonpharmacological interventions for the prevention of type 2 diabetes mellitus," Nature Reviews Endocrinology, 2012, vol. 8, pp. 363-373.

Secchi, A. et al., "Cardiovascular disease and neoplasms after pancreas transplantation," Lancet, 1998, vol. 352, pp. 65-66.

Senger, S. et al., "Celiac Disease Histopathology Recapitulates Hedgehog Downregulation, Consistent with Wound Healing Processes Activation," PloS One, 2015, vol. 10, pp. e0144634.

Smets, Y.F. et al., "Effect of simultaneous pancreas-kidney transplantation on mortality of patients with type-1 diabetes mellitus and end-stage renal failure," Lancet, 1999, vol. 1915-1919.

Spinelli, A. et al. "Intestinal fibrosis in Crohn's disease: medical treatment or surgery?" Current Drug Targets, 2010, vol. 11, No. 2, pp. 242-248.

Sridhar, S.S. et al., "Insulin-insulin-like growth factor axis and colon cancer," J Clin Oncol, 2009, vol. 27, pp. 165-167.

Stange, D.E. et al., "Concise review: the yin and yang of intestinal (cancer) stem cells and their progenitors," Stem Cells, 2013, vol. 31, pp. 2287-2295.

Svedlund, J. et al., "GSRS—a clinical rating scale for gastrointestinal symptoms in patients with irritable bowel syndrome and peptic ulcer disease," Digestive diseases, 1988, vol. 33, pp. 129-134.

Taghipour, N. et al., "An experimental model of colitis induced by dextran sulfate sodium from acute progresses to chronicity in C57BL/6: correlation between conditions of mice and the environment," Gastroenterology and Hepatology from Bed to Bench, 2016, vol. 9, No. 1, pp. 45-52.

Talley, N.J. et al., "Impact of chronic gastrointestinal symptoms in diabetes mellitus on health-related quality of life," Am J Gastroenterol, 2001, vol. 96, pp. 71-76.

The Diabetes Control and Complications Research Group, "The effect of intensive treatment of diabetes on the development and progression of long-term complications in insulin-dependent mellitus," N Engl J Med, Sep. 30, 1993, vol. 329, pp. 977-986.

Tomlinson, I.M. et al., "The repertoire of human germline VH sequences reveals about fifty groups of VH segments with different hypervariable loops," Journal of Molecular Biology, 1992, vol. 227, No. 3, pp. 776-798.

United States Office Action, U.S. Appl. No. 16/855,992, filed Apr. 12, 2021, fourteen pages.

(56) References Cited

OTHER PUBLICATIONS

Van Der Flier, L.G. et al., "Stem cells, self-renewal, and differentiation in the intestinal epithelium," Annual Review of Physiology, 2009, vol. 71, pp. 241-290.
Venepalli, N.K. et al., "Phase I Study of IGF-Methotrexate Conjugate in the Treatment of Advanced Tumors Expressing IGF-1 R," American Journal of Clinical Oncology, Nov. 2019, vol. 42, No. 11, pp. 862-869.
Vergani, A. et al., "A novel clinically relevant strategy to abrogate autoimmunity and regulate alloimmunity in NOD mice," Diabetes, 2010, vol. 59, pp. 2253-2264.
Vergani, A. et al., "Effect of the puringeric inhibitor oxidized ATP in a model of islet allograft rejection," Diabetes, 2013, vol. 62, pp. 1665-1675.
Wang, S. et al., "Circulating IGF-1 promotes prostate adenocarcinoma via FOXO31/BIM signaling in a double-transgenic mouse model," Oncogene, Jul. 16, 2019, vol. 38, pp. 6338-6353.
Wang, Z. et al., "Integrin targeted drug and gene delivery," Expert Opinion on Drug Delivery, 2010, vol. 7, No. 2, pp. 159-171.
Williams, A.C. et al., "Insulin-like growth factor binding protein 3 (IGFBP-3) potentiates TRAIL-induced apoptosis of human colorectal carcinoma cells through inhibition of NF-kappaB," Cell Death Differ, 2007, vol. 14, pp. 137-145.
Wright, A. et al., "Effect of glycosylation on antibody function: implications for genetic engineering," Trends in Biotechnology, 1997, vol. 15, No. 1, pp. 26-32.
Wu, M.J. et al., "Colonic transit time in long-term dialysis patients," Am J Kidney Dis, 2004, vol. 44, pp. 322-327.
Yakar, S. et al., "Serum complexes of insulin-like growth factor-1 modulate skeletal integrity and carbohydrate metabolism," FASEB J, 2009, vol. 23, No. 3, pp. 709-719.
Yancu, D. et al., "A phenotype of IGFBP-3 knockout mice revealed by dextran sulfate-induced colitis," Journal of gastroenterology and hepatology, 2017, vol. 32, No. 1, pp. 146-153.
Yeung, Y.A. et al., "Engineering Human IgG1 Affinity to Human Neonatal Fc Receptor: Impact of Affinity Improvement on Pharmacokinetics in Primates," The Journal of Immunology, 2009, vol. 182, No. 12, pp. 7663-7671.
Yi, P. et al., "Perspectives on the activities of ANGPTL8/betatrophin," Cell, 2014, vol. 159, pp. 467-468.
Zahnd, C. et al., "A Designed Ankyrin Repeat Protein Evolved to Picomolar Affinity to Her2," J Mol Biol, 2007, vol. 369, pp. 1015-1028.
Zeki, S.S. et al., "Stem cells and their implications for colorectal cancer," Nature Reviews, Gastroenterology & Hepatology, 2011, vol. 8, pp. 90-100.
Zhao, J. et al., "Biomechanical and morphometric intestinal remodelling during experimental diabetes in rats," Diabetologia, 2003, vol. 46, pp. 1688-1697.
Ziegler, A.G. et al., "Seroconversion to multiple islet autoantibodies and risk of progression to diabetes in children," Jama, 2013, vol. 309, pp. 2473-2479.
Ziskin, J.L. et al., "In situ validation of an intestinal stem cell signature in colorectal cancer," Gut, 2013, vol. 62, pp. 1012-1023.
Collard, T.J. et al., "Transcriptional upregulation of the insulin-like growth factor binding protein IGFBP-3 by sodium butyrate increases IGF-independent apoptosis in human colonic adenoma-derived epithelial cells," Carcinogenesis, 2003, vol. 24, pp. 393-401.
Katrucha, A.G. "Obtaining Recombinant Antibodies and Methods for Increasing their Affinity," Advances in Biological Chemistry, vol. 50, 2010, pp. 207.
Koiko, R. et al., "Detection of Antibodies and Determination of their Characteristics," Immunology, 2008, pp. 61-62.

IBD samples were re-challenged in vitro with IGFBP3 50 ng/ml (n=3 samples)

A

B

ANTIBODIES AND USES THEREOF

SEQUENCE LISTING

The instant application contains a Sequence Listing which has been submitted in ASCII format via EFS-Web and is hereby incorporated by reference in its entirety. Said ASCII copy, created on Apr. 9, 2020, is named eolf-othd-000001.txt and is 58,479 bytes in size.

TECHNICAL FIELD

The present invention relates to an antibody or antigen binding fragment thereof that binds specifically to IGFBP3 and does not displace the binding of IGF-I to IGFBP3. The antibody inhibits or reduces the binding of IGFBP3 to the TMEM219 receptor. The invention also relates to methods for their production, pharmaceutical compositions containing said antibodies, and uses thereof.

BACKGROUND ART

IGFBP3/TMEM219 Axis

The insulin-like growth factor binding proteins is a family of seven binding proteins which modulate the bioavailability of insulin-like growth factors (IGFs). Among them IGFBP3 is the most abundant, being present in almost all tissues, and has the higher affinity for IGFs; indeed, approximately 80-90% of IGFs are bound to IGFBP3 in a ternary complex with the acid labile subunit (ALS)(1).

In addition to its ability to regulate IGFs availability, IGFBP3 has also been shown to have IGF-independent functions (2). Indeed, it is able to associate with cell-surface proteins, cell-surface receptors with integral signaling capacity, intracellular and nuclear proteins (transcription factors) thus influencing cell growth and directly inducing apoptosis (2). Among death receptors, TMEM219, a single-span membrane protein, was shown to bind specifically to IGFBP-3 but not to other IGFBP species (3). Binding of IGFBP3 to TMEM219 induces caspase-8-mediated apoptosis in a variety of cells, including cancer cells (i.e. prostate and breast) (3), but also stem cells (i.e. colonic stem cells) (4). Blocking or enhancing IGFBP3/TMEM219 axis with different strategies has been shown to respectively preventing or increasing cell death. To the best of our knowledge there are no monoclonal antibody against TMEM219 or IGFBP3 commercially available capable of preventing the IGFBP3/TMEM219 binding and halting the IGFBP3, IGF-I independent and Caspase8-mediated, detrimental effects on target tissues/cells.

IGFBP3/TMEM219 Axis in Diabetes

Type 1 (T1D) and type 2 diabetes (T2D) are both characterized by a loss of beta cells, which results in a reduced secretion of insulin, failure to control blood glucose levels and hyperglycemia(5,6). Despite different etiological mechanisms, either autoimmune response in T1D and insulin resistance/inflammation in T2D, both lead to a progressive reduction of beta cell mass. Indeed it is becoming evident that the occurring immune activation do not appear sufficient to fully explain beta cell loss in T1D (5). Moreover, the failure of immunotherapies to cure T1D(7) highlighted that: (i) autoimmunity may not be the sole factor involved in T1D pathogenesis and (ii) alternative strategies that targets different mechanisms of disease, such as beta cell loss, are needed in order to establish an effective treatment for T1D. The observation that scattered beta cells are detected in individuals with long-standing T1D(8) confirms that either new beta cells must be occurring in order to preserve the beta cell turnover(5, 9), or the destroyed beta-cells may be "different" and prone to death(10). This may suggest that the up/down-regulated expression of surface beta cell receptors may have a key role in making them visible to immune system and, more importantly, that other non-immunological determinants may modulate beta cell fate and function. Therefore, preventing the non-immunological beta cell destruction in T1D and the progressive loss of beta cells in T2D may skew the balance between beta cell generation and destruction towards the recovery of the appropriate beta cell mass, thus paving the way for novel therapeutic approaches capable of halting or delaying the very first phase of the disease.

It has been shown that TMEM219, the IGFBP3 receptor, is expressed in a beta cell line and in human/murine islets, and that its ligation is toxic to beta cells. Interestingly, it has been also observed that mice transgenic for human IGFBP3 develop hyperglycemia, exhibit a reduced islets mass and show a decrease response to insulin-glucose stimulation (11), while those knocked down for IGFBP3 did not show any alteration in terms of glycometabolic control (12).

In humans, Drogan and colleagues recently published that elevated circulating levels of IGFBP3 are associated with the development of T2D (13). Moreover, a recent study by the Diabimmune Study group demonstrated that IGFBP3 levels correlate with autoantibody positivity and chance to seroconversion in children at risk for T1D, thus suggesting a role for circulating IGFBP3 in the early development of beta cell autoimmunity (14).

TMEM219, the IGFBP3 receptor, has been already described as a death receptor, whose activation triggers Caspase8-mediated apoptosis within the target cells thus leading to their loss(4).

IGFBP3/TMEM219 Axis in Inflammatory Bowel Disease

Intestinal stem cells (ISCs) reside at the bottom of small and large intestine crypts and control the crypts regeneration and turnover. In particular, ISCs can differentiate along the crypts to generate goblet cells, enterocytes, enteroendocrine cells(4).

Inflammatory bowel disease (IBD) is an immune-mediated chronic condition that encompasses two clinical entities, Crohn's disease (CD) and ulcerative colitis (UC), and affects nearly 2.5 million of individuals in Europe and 1 million in USA(15). The pathogenesis of IBD is still under investigation, but recent evidences suggest that an impaired differentiation of ISCs towards Paneth cells, in ileal CD, and towards goblet cells in UC, may play a key-role in the onset of the disease. In particular, local signaling and inflammatory pathways in the mucosa both respond to external stimuli and preserve ISCs number and function, thus maintaining intestinal homeostasis (16). Indeed recently, Yancu et al., published results that support the role of IGFBP-3 in CD. Indeed, they demonstrated that, the knockout of IGFBP3 has a role in modulating inflammation in the Dextran-Sodium-Sulphate (DSS) colitis murine model(17).

The inventors have recently found that the insulin-like growth factor binding protein 3 (IGFBP) receptor, TMEM219 receptor, is expressed on ISCs and that its interaction with the circulating hormone IGFBP3 controls ISCs fate and function in a model of intestinal disorders in diabetes, the diabetic enteropathy(4). Since diabetic enteropathy and IBD share common features, these results may add important insights in the still unknown IBD pathogenesis and will possibly lead to the introduction of a new therapeutic approach for IBD treatment.

Current available therapy for IBD is based on the use of anti-inflammatory and immunotherapeutic strategies, which are aggravated by several adverse effects and whose effectiveness in the long-term remains questionable. Surgery is also successfully employed in advanced state of the disease especially in UC (15). Relapsing of the disease mostly in CD is also frequent, thus highlighting the need for a different therapeutic approach. As a result, the identification of novel therapeutic targets and strategies in the treatment of IBD is of a high clinically relevance for the health community.

WO2016193497 and WO2016193496 describe a TMEM219 extracellular domain, ecto-TMEM that is an effective therapeutic agent. However, receptor constructs are less desirable as therapeutic agents than are antibodies. Therefore, there is still a need for antibodies that mimic the effects of ecto-TMEM.

SUMMARY OF THE INVENTION

Disclosed herein are antibodies that bind with high affinity and specificity to human IGF binding protein 3 (IGFBP3) and that are capable of reducing or abrogating binding of IGFBP3 to its cognate receptor, TMEM219. These neutralizing antibodies are useful in treating disorders in which IGFBP3 binding to TMEM219 contributes to the pathophysiology of the disease, including diabetic enteropathy, inflammatory bowel disease (IBD), and type 1 or type 2 diabetes. Such neutralizing antibodies provide a therapeutic agent that retains the activities of the receptor-based ligand trap, ecto-TMEM219 (WO 2016/193497 and WO 2016/193496, incorporated herein by reference in their entireties), with the additional advantages of an antibody therapeutic.

In a first aspect, it is provided an isolated antibody or antigen binding fragment thereof that binds to human IGFBP3 which:
  does not displace the binding of IGF-I to IGFBP3 and/or does not interfere with the binding of IGF-I to IGFBP3 and
  inhibits or reduces the binding of IGFBP3 to the TMEM219 receptor.

Preferably the isolated antibody or antigen binding fragment thereof inhibits, reduces, or neutralizes the activation of the TMEM219 receptor induced by IGFBP3.

Activation of the TMEM219 receptor induced by IGFBP3 may be measured by any known method in the art or as described below. In particular, IGFBP3-induced activation of a TMEM219 receptor may be measured by measuring apoptosis increase or decrease in minigut growth as described therein.

The present invention also provides an isolated antibody or antigen binding fragment thereof that has at least one activity selected from:
  a—increase in IGFBP3 treated healthy subject minigut growth
  b—increase in IBD-patient minigut growth;
  c—increase in diabetic enteropathy serum treated healthy subject minigut growth;
  d—increase in expression of EphB2 and/or LGR5 in IGFBP3 treated healthy subject minigut;
  e—decrease in caspase 8 expression in IGFBP3 treated healthy subject minigut;
  f—decrease in B-cell loss in IGFBP3 treated β-cell;
  g—increase in expression of insulin in IGFBP3 treated β-cell; and
  h—decrease in apoptosis of β-cell in IGFBP3 treated β-cell.

Preferably the increase in a), b) and c) is by at least 20%; the increase in d) and e) is by at least 50%; the decrease in f) and the increase in g) is by at least 10%.

The invention provides an isolated antibody or antigen binding fragment thereof that binds specifically to IGFBP3, preferably free IGFBP3, and does not bind to IGFBP3 bound to IGF-I, Free IGFBP3 is the portion of circulating IGFBP3 not complexed to IGF1 and/or IGF1/ALS.

The invention provides an isolated antibody or antigen binding fragment thereof comprising:
  a. a heavy chain variable domain (VH) comprising:
    i. a CDR1 sequence of the amino acid sequence selected from the group consisting of: SEQ ID NO: 1 to SEQ ID NO: 7;
    ii. a CDR2 sequence of the amino acid sequence selected from the group consisting of: SEQ ID NO:8 to SEQ ID NO: 16; and
    iii. a CDR3 sequence of the amino acid sequence selected from the group consisting of: SEQ ID NO:17 to SEQ ID NO:26; and
  b. a light chain variable domain (VL) comprising:
    i. a CDR1 sequence of the amino acid sequence selected from the group consisting of: SEQ ID NO:27 to SEQ ID NO:36;
    ii. a CDR2 sequence of the amino acid sequence selected from the group consisting of: SEQ ID NO:37 to SEQ ID NO:44; and
    iii. a CDR3 sequence of the amino acid sequence selected from the group consisting of: SEQ ID NO:45 to SEQ ID NO:54;

Preferably the isolated antibody or antigen binding fragment thereof comprises the CDRs as indicated in Table 2 and/or in Table 3.

Preferably said antibody or antigen binding fragment thereof binds specifically to IGFBP3, and does not bind to IGFBP3 bound to IGF-I. Preferably it binds to free IGFBP3 and does not bind to IGFBP3 bound to IGF-I.

Preferably it has at least one activity selected from:
  a—increase in IGFBP3 treated healthy subject minigut growth
  b—increase in IBD-patient minigut growth;
  c—increase in diabetic enteropathy serum treated healthy subject minigut growth;
  d—increase in expression of EphB2 and/or LGR5 in IGFBP3 treated healthy subject minigut;
  e—decrease in caspase 8 expression in IGFBP3 treated healthy subject minigut;
  f—decrease in B-cell loss in IGFBP3 treated β-cell;
  g—increase in expression of insulin in IGFBP3 treated β-cell; and
  h—decrease in apoptosis of β-cell in IGFBP3 treated β-cell.

Preferably the increase in a), b) and c) is by at least 20%; the increase in d) and e) is by at least 50%; the decrease in f) and the increase in g) is by at least 10%.

Preferably the isolated antibody or antigen binding fragment thereof comprises:
  a. a heavy chain variable domain sequence of the amino acid sequence selected from the group consisting of: SEQ ID NO:55 to SEQ ID NO:65;
  b. a light chain variable domain sequence of the amino acid sequence selected from the group consisting of: SEQ ID NO: 66 to SEQ ID NO:76; or
  c. the light chain variable domain of (a) and the heavy chain variable domain of (b).

Still preferably the isolated antibody is Yu139-A02, Yu139-A03, Yu139-B01, Yu139-C01, Yu139-C02, Yu139-D02, Yu139-D03, Yu139-F02, Yu139-G01, Yu139-G03 or Yu139-H03 or antigen binding fragment thereof, preferably Yu139-A03, Yu139-C01, Yu139-G03 or Yu139-H03 or antigen binding fragment thereof, as reported in Tables 2-7.

Still preferably the isolated antibody is Yu139-A02 having SEQ ID NO:55 and SEQ ID NO: 66, Yu139-A03 having SEQ ID NO:56 and SEQ ID NO:67, Yu139-B01 having SEQ ID NO: 57 and SEQ ID NO:68, Yu139-C01 having SEQ ID NO:58 and SEQ ID NO:69, Yu139-C02 having SEQ ID NO:59 and SEQ ID NO:70, Yu139-D02 having SEQ ID NO:60 and SEQ ID NO:71, Yu139-D03 having SEQ ID NO:61 and SEQ ID NO:72, Yu139-F02 having SEQ ID NO:62 and SEQ ID NO:73, Yu139-G01 having SEQ ID NO:63 and SEQ ID NO:74, Yu139-G03 having SEQ ID NO:64 and SEQ ID NO:75 or Yu139-H03 having SEQ ID NO:65 and SEQ ID NO:76, preferably Yu139-A03, Yu139-C01, Yu139-G03 or Yu139-H03.

Preferably the isolated antibody or antigen binding fragment of the invention binds to human IGFBP3 with an affinity constant lower than or equal to $4 \times 10^{-6}$ M.

The invention also provides an isolated antibody or antigen binding fragment thereof that:
(a) binds specifically to an epitope on IGFBP3, e.g., the same or similar epitope as the epitope recognized by the monoclonal antibody Yu139-A02, A03, B01, C01, C02, D02, D03, F02, G01, G03, H03 as defined in Tables 4 and 5; or
(b) cross-competes for binding with the monoclonal antibody Yu139-A02, A03, B01, C01, C02, D02, D03, F02, G01, G03, H03 as defined in Tables 4 and 5; or
(c) shows the same or similar binding affinity or specificity, or both, as any of Yu139-A02, A03, B01, C01, C02, D02, D03, F02, G01, G03, H03 as defined in Tables 4 and 5; or
(d) has one or more biological properties of an antibody molecule described herein, e.g., an antibody molecule chosen from, e.g., any of Yu139-A02, A03, B01, C01, C02, D02, D03, F02, G01, G03, H03 as defined in Tables 4 and 5; or
(e) has one or more pharmacokinetic properties of an antibody molecule described herein, e.g., an antibody molecule chosen from, e.g., any of Yu139-A02, A03, B01, C01, C02, D02, D03, F02, G01, G03, H03 as defined in Tables 4 and 5.

Preferably the isolated antibody or antigen binding fragment thereof of the invention is a human or humanized antibody.

More preferably the isolated antibody or antigen binding fragment thereof of the invention is an IgG2 or IgG4 antibody, preferably an IgG2 kappa antibody, an IgG2 lambda antibody, an IgG4 kappa antibody or an IgG4 lambda antibody.

The invention provides an isolated polynucleotide comprising at least one sequence that encodes the antibody or antigen binding fragment thereof as defined above, preferably said polynucleotide is a cDNA.

The invention provides a vector comprising the polynucleotide as defined above, preferably said vector is selected from the group consisting of a plasmid, a viral vector, a non-episomal mammalian vector, an expression vector, and a recombinant expression vector.

The invention further provides an isolated cell comprising the polynucleotide as defined above or the vector as defined above, preferably the isolated cell is a hybridoma or a Chinese Hamster Ovary (CHO) cell or a Human Embryonic Kidney cells (HEK293).

The invention further provides the antibody or antigen binding fragment thereof or the isolated polynucleotide or the vector or the isolated cell s defined above for use as a medicament, preferably for use in the treatment of: diabetes, intestinal and/or bowel disorder, malabsorption syndrome, cachexia or diabetic enteropathy, preferably diabetes is Type I or Type II diabetes preferably the intestinal and/or bowel disorder is inflammatory bowel disease, celiac disease, ulcerative colitis, Crohn's disease or intestinal obstruction.

The invention provides also a pharmaceutical composition comprising the isolated antibody or antigen binding fragment thereof or the isolated polynucleotide or the vector or the isolated cell as defined above and pharmaceutically acceptable carrier, preferably for use in the treatment of: diabetes, intestinal and/or bowel disorder, malabsorption syndrome, cachexia or diabetic enteropathy, preferably the intestinal and/or bowel disorder is inflammatory bowel disease, celiac disease, ulcerative colitis, Crohn's disease or intestinal obstruction.

The invention provides a method of inhibiting the binding of IGFBP3 to TMEM219 receptor, comprising contacting IGFBP3 with the antibody or composition as defined above.

The invention provides a method of treatment of: diabetes, preferably Type 1 or Type 2 diabetes, intestinal and/or bowel disorder, malabsorption syndrome, cachexia or diabetic enteropathy, preferably the intestinal and/or bowel disorder is inflammatory bowel disease, IBD, celiac disease, Crohn's disease or intestinal obstruction, the method comprising administering to a subject in need thereof a pharmaceutical composition comprising the isolated antibody or antigen binding fragment thereof or the isolated polynucleotide or the vector or the isolated cell as defined above and pharmaceutically acceptable carrier or administering to a subject in need thereof the isolated antibody or antigen binding fragment thereof or the isolated polynucleotide or the vector or the isolated cell as defined above.

The present invention also provides a method for producing an antibody or antigen binding fragment thereof, comprising obtaining the cell as defined above and producing the antibody or antigen binding fragment thereof.

In some embodiments, the combination includes an inhibitor of IGFBP3 (e.g., an anti-IGFBP3 antibody molecule as described herein). Thus, compositions and methods for detecting IGFBP3, as well as methods for treating various disorders including diabetes, as well as intestinal and/or bowel disorders, using the anti-IGFBP3 antibody molecules and combinations thereof are disclosed herein.

Accordingly, in one aspect, the invention features an antibody molecule (e.g., an isolated or recombinant antibody molecule) having one or more of the following properties:
(i) binds to IGFBP3, e.g., human IGFBP3, with high affinity, e.g., with an affinity constant of at least about $4 \times 10^6$ M$^{-1}$, preferably $10^7$ M$^{-1}$, typically about $10^8$ M$^{-1}$ and more typically, about $10^9$ M$^{-1}$ to $10^{10}$ M$^{-1}$ or stronger;
(ii) binds to free IGFBP3 and does not substantially bind to IGFBP3 bound to IGF-I;
(iii) inhibits or reduces binding of IGFBP3 to its receptor, TMEM;
(iv) binds specifically to an epitope on IGFBP3, e.g., a different epitope from the epitope recognized by commercial antibody LSBIO LS-C45037 or clone 83.8F9;
(v) binds specifically to an epitope on IGFBP3, e.g., the same or similar epitope as the epitope recognized by the monoclonal antibody Yu139-A02, A03, B01, C01, C02, D02, D03, F02, G01, G03, H03 as defined in Tables 4 and 5;
(vi) cross-competes for binding with the monoclonal antibody Yu139-A02, A03, B01, C01, C02, D02, D03, F02, G01, G03, H03 as defined in Tables 4 and 5;
(vii) shows the same or similar binding affinity or specificity, or both, as any of Yu139-A02, A03, B01, C01, C02, D02, D03, F02, G01, G03, H03 as defined in Tables 4 and 5;
(viii) shows the same or similar binding affinity or specificity, or both, as an antibody molecule (e.g., an heavy chain variable region and light chain variable region) described in Tables 2-7;
(ix) shows the same or similar binding affinity or specificity, or both, as an antibody molecule (e.g., an heavy chain variable region and light chain variable region) having an amino acid sequence shown in Tables 2-5;
(x) shows the same or similar binding affinity or specificity, or both, as an antibody molecule (e.g., an heavy chain variable region and light chain variable region) encoded by the nucleotide sequence shown in Tables 6-7;
(xi) binds the same or an overlapping epitope with a second antibody molecule to IGFBP3, wherein the second antibody molecule is an antibody molecule described herein, e.g., an antibody molecule chosen from Yu139-A02, A03, B01, C01, C02, D02, D03, F02, G01, G03, H03 as defined in Tables 4 and 5;
(xii) has one or more biological properties of an antibody molecule described herein, e.g., an antibody molecule chosen from, e.g., any of Yu139-A02, A03, B01, C01, C02, D02, D03, F02, G01, G03, H03 as defined in Tables 4 and 5;
(xiii) has one or more pharmacokinetic properties of an antibody molecule described herein, e.g., an antibody molecule chosen from, e.g., any of Yu139-A02, A03, B01, C01, C02, D02, D03, F02, G01, G03, H03 as defined in Tables 4 and 5;
(xiv) inhibits one or more activities of IGFBP3, e.g., results in one or more of: an increase of at least 20% in the development of minigut from IBD-patient derived tissue sample when compared to untreated samples and/or an increase of at least 20% in the development of minigut growth in presence of IGFBP3 when compared to untreated samples or an increase of at least 20% in the development of minigut growth in presence of diabetic enteropathy serum when compared to untreated samples;
(xv) induces an increase in EphB2 and LGR5 of at least 50% compared to the IGFBP3-treated samples; or decrease in caspase 8 expression level of at least 50% compared to the IGFBP3-treated samples; or
(xvi) inhibits one or more activities of IGFBP3, e.g., results in one or more of: a reduction in beta cell loss, or an increase in Insulin; The reduction in beta cell loss or the increase in insulin is at least 10% compared to IGFBP3 treated samples;
(xvii) inhibits, reduces or neutralizes one or more activities of IGFBP3, resulting in blockade or reduction of IGFBP3 induced apoptosis;
(xviii) binds human IGFBP3 and is cross-reactive with cynomolgus IGFBP3.

Nucleic acid molecules encoding the antibody molecules, expression vectors, host cells and methods for making the antibody molecules are also provided. Immunoconjugates, multi- or bispecific antibody molecules and pharmaceutical compositions comprising the antibody molecules are also provided.

Without being bound to any theory, it is believed that IGFBP3/TMEM219 axis is dysfunctional in inflammatory bowel diseases (IBD) thus leading to ISCs loss and to altered function of the mucosal barrier, which is further invaded by microbes that trigger and sustain immune response activation and inflammation. The use of agents that block the IGFBP3-TMEM219 interaction in IBD may protect ISCs and preserve the integrity of the intestinal barrier, thus preventing the development of local inflammation.

Further, activation of TMEM219 signaling increases apoptosis of beta cells through upregulation of caspase 8 expression and reduced insulin expression. IGFBP3 is increased in the serum of patients with pre-T1D and pre-T2D as well as in newly diagnosed and long-standing diabetes patients and TMEM219 is expressed in beta cells. An expression or overexpression of TMEM219 favors beta cells destruction and affects beta cell mass, and the consequent hyperglycemia/inflammation perpetuates the process during diabetes onset and progression. Altered glycemic control and inflammation in pre-diabetic conditions favor an increased IGFBP3 hepatic production, which may target TMEM219 expressed on pancreatic beta cells and trigger a loop where TMEM219 overexpression parallels the increase in IGFBP3 release. Then TMEM219 may trigger beta cell death and thus targeting the IGFBP3/TMEM219 axis may prevent such cell death.

The anti-IGFBP3 antibody molecules disclosed herein can be used (alone or in combination with other agents or therapeutic modalities) to treat, prevent and/or diagnose disorders, such as diabetes, as well as intestinal and/or bowel disorders, malabsorption syndrome, inflammatory bowel disease, cachexia, IBD, celiac disease, diabetic enteropathy. Additionally, disclosed herein are methods and compositions comprising a combination of two, three or more therapeutic agents chosen from one, two, or all of the following categories (i)-(iii): (i) an agent that treat diabetes; (ii) an anti-inflammatory agent; or (iii) an immunotherapeutic agent.

The additional therapeutic agent may be selected from an agent that treat diabetes including: insulin, Insulin glargine as detailed in Vandana, 2014 (19, incorporated by reference), biguanide, glucosidase inhibitors, thiazolidinedione, DPP-4 inhibitors, GLP-1 receptor agonists as detailed in George et al 2013 (20, incorporated by reference)), an agent used to prevent diabetes, aspirin, anticoagulation and platelet anti-aggregation agents (such as enoxaparin, eparin, sulodexide); cholesterol-lowering drugs (such as statins, bile acids sequestrants, ezetimibe, fibrates as described in Marsha et al 2011 (21, incorporated by reference)); other blood pressure lowering agents (such as thiazide, ACE inhibitors, beta and alpha blockers); an anti-apoptotic agent, an anti-inflammatory agent, corticosteroids and immune suppressive agent (22, incorporated by reference), adjuvant therapy in organ transplantation, protective agent in cell therapy approach, a pain reliever, antibiotic, probiotics, TNF-alpha blockers (23, incorporated by reference), SGLT2 inhibitors (such as gliflozin derivates), integrin inhibitors (24, incorporated by reference).

Methods to measure an increase in minigut growth when compared to minigut growth in the presence of IGFBP3, and/or in the presence of diabetic entheropathy serum are known in the art and are described in several publications (4, 18, 27, 28) or as described in the method section below.

Methods to measure an increase and/or a decrease in EphB2, LGR5 or caspase 8 expression when compared to expression in the presence of IGFBP3 are known in the art and include quantitative RT-PCR, Realt-Time RT-PCR, microarray, northern blotting, RNA-Seq (29,30) or as described in the method section below.

Methods to measure a decrease in beta-cell loss when compared to beta-cell loss in the presence of IGFBP3 are known in the art and include cell proliferation assays (CFSE staining, Calcein/PI staining, Trypan Blue exclusion, BrdU staining, MTT) apoptosis assays (TUNEL, Caspase activation and detection, Annexin V binding) or as described in the method section below.

Methods to measure an increase in insulin level when compared to insulin level in the presence of IGFBP3 are known in the art and include western blots, ELISA mass spectrometry (31-33).

Methods to measure a decrease in apoptosis when compared to apoptosis in the presence of IGFBP3 are known in the art and include DNA fragmentation, Caspase activation analysis, Mithocondrial membrane permeabilization, Annexin V binding (34) or as described in the method section below.

In some embodiments, the antibody molecule binds to IGFBP3 with high affinity, e.g., with a KD that is about the same, or at least about 10%, 20%, 30%, 40%, 50%, 60%, 70%, 80% or 90% higher or lower than the KD of a murine anti-IGFBP3 antibody molecule or chimeric anti-IGFBP3 antibody molecule or a commercial anti-IGFBP3 antibody molecule. In some embodiments, the KD of the murine or chimeric anti-IGFBP3 antibody molecule is less than about 0.4, 0.3, 0.2, 0.1, or 0.05 nM, e.g., measured by a Biacore method or KinExA=kinetic exclusion assays. In some embodiments, the KD of the murine or chimeric anti-IGFBP3 antibody molecule is less than about 0.2 nM. In other embodiments, the KD of the murine or chimeric anti IGFBP3 antibody molecule is less than about 10, 5, 3, 2, or 1 nM, e.g., measured by binding on cells expressing IGFBP3 (e.g., 300.19 cells). In some embodiments, the KD of the murine or chimeric anti IGFBP3 antibody molecule is less than about 1 nM.

Methods to measure binding to IGFBP3 are known in the art as protein-protein interactions assays and include ELISA, co-immunoprecipitation, surface plasmon resonance, FRET-Forster resonance energy transfer (35) or as described in the method section below.

In some embodiments, the expression level of the antibody molecule is higher, e.g., at least about 0.5, 1, 2, 3, 4, 5, 6, 7, 8, 9 or 10-fold higher, than the expression level of a murine or chimeric antibody molecule, e.g., a murine, commercial or chimeric anti-IGFBP3 antibody molecule such as LSBIO LS-C45037, clone 83.8F9 or Novus NBP2-12364. In some embodiments, the antibody molecule is expressed in HEK293 cells, CHO cells or any suitable mammalian cell line known in the art.

In some embodiments, the anti-IGFBP3 antibody molecule reduces one or more IGFBP3-associated activities with an IC50 (concentration at 50% inhibition) that is about the same or lower, e.g., at least about 10%, 20%, 30%, 40%, 50%, 60%, 70%, 80% or 90% lower, than the IC50 of a murine, commercial or chimeric anti-IGFBP3 antibody molecule, e.g., a murine commercial or chimeric anti-IGFBP3 antibody molecule described herein.

In some embodiments, the anti-IGFBP3 antibody molecule has improved stability, e.g., at least about 0.5, 1, 2, 3, 4, 5, 6, 7, 8, 9 or 10-fold more stable in vivo or in vitro, than a murine, commercial or chimeric anti-IGFBP3 antibody molecule, e.g., a murine, commercial or chimeric anti-IGFBP3 antibody molecule such as LSBIO LS-C45037, clone 83.8F9 or Novus NBP2-12364.

In one embodiment, the anti IGFBP3 antibody molecule is a humanized antibody molecule.

In another embodiment, the anti-IGFBP3 antibody molecule comprises at least one antigen-binding region, e.g., a variable region or an antigen-binding fragment thereof, from an antibody described herein, e.g., an antibody chosen from any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences.

In yet another embodiment, the anti-IGFBP3 antibody molecule comprises at least one, two, three or four variable regions from an antibody described herein, e.g., an antibody chosen from any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences.

In yet another embodiment, the anti-IGFBP3 antibody molecule comprises at least one or two heavy chain variable regions from an antibody described herein, e.g., an antibody chosen from any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences.

In yet another embodiment, the anti-IGFBP3 antibody molecule comprises at least one or two light chain variable regions from an antibody described herein, e.g., an antibody chosen from any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences.

In yet another embodiment, the anti-IGFBP3 antibody molecule includes a heavy chain constant region for an IgG4, e.g., a human IgG4. In one embodiment, the human IgG4 includes a substitution at position 228 (e.g., a Ser to Pro substitution). In still another embodiment, the anti-IGFBP3 antibody molecule includes a heavy chain constant region for an IgG1, e.g., a human IgG1. In one embodiment, the human IgG1 includes a substitution at position 297 (e.g., an Asn to Ala substitution). In one embodiment the human IgG1 includes a substitution at position 250, a substitution at position 428, or both (e.g., a Thr to Gln substitution at position 250 and/or a Met to Leu substitution at position 428). In one embodiment, the human IgG1 includes a substitution at position 234, a substitution at position 235, or both (e.g., a Leu to Ala substitution at position 234 and/or a Leu to Ala substitution at position 235). In one embodiment, the heavy chain constant region comprises an amino sequence set forth in Table 8, or a sequence substantially identical (e.g., at least 80%, 85%, 90%, 92%, 95%, 97%, 98%, 99% or higher identical) thereto.

In yet another embodiment, the anti-IGFBP3 antibody molecule includes a kappa light chain constant region, e.g., a human kappa light chain constant region. In one embodiment, the light chain constant region comprises an amino sequence set forth in Table 8, or a sequence substantially identical (e.g., at least 80%, 85%, 90%, 92%, 95%, 97%, 98%, 99% or higher identical) thereto.

In another embodiment, the anti-IGFBP3 antibody molecule includes a heavy chain constant region for an IgG4, e.g., a human IgG4, and a kappa light chain constant region, e.g., a human kappa light chain constant region, e.g., a heavy and light chain constant region comprising an amino sequence set forth in Table 8, or a sequence substantially identical (e.g., at least 80%, 85%, 90%, 92%, 95%, 97%, 98%, 99% or higher identical) thereto. In yet another embodiment, the anti-IGFBP3 antibody molecule includes a heavy chain constant region for an IgG1, e.g., a human IgG1, and a kappa light chain constant region, e.g., a human kappa light chain constant region, e.g., a heavy and light chain constant region comprising an amino sequence set forth in Table 8, or a sequence substantially identical (e.g., at least 80%, 85%, 90%, 92%, 95%, 97%, 98%, 99% or higher identical) thereto. In one embodiment, the human IgG1 or IgG4 includes a substitution at the variable region to decrease aggregation, reduce charge heterogeneity, increase affinity and modulate antigen binding; removal by mutation of instability hotspot in the CDR, putative N-glycosylation sites in the variable region as described in (26), incorporated by reference.

In another embodiment, the anti-IGFBP3 antibody molecule includes a heavy chain variable domain and a constant region, a light chain variable domain and a constant region, or both, comprising the amino acid sequence of any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences. The anti-IGFBP3 antibody molecule, optionally, comprises a leader sequence from a heavy chain, a light chain, or both.

In yet another embodiment, the anti-IGFBP3 antibody molecule includes at least one, two, or three complementarity determining regions (CDRs) from a heavy chain variable region of an antibody described herein, e.g., an antibody chosen from any of any of Yu139-A02, A03, B01, C01, C02, D02, D03, F02, G01, G03, H03, or BAP058-Clone-O; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences.

In yet another embodiment, the anti-IGFBP3 antibody molecule includes at least one, two, or three CDRs (or collectively all of the CDRs) from a heavy chain variable region comprising an amino acid sequence shown in Tables 2-5 or encoded by a nucleotide sequence shown in Tables 6-7. In one embodiment, one or more of the CDRs (or collectively all of the CDRs) have one, two, three, four, five, six or more changes, e.g., amino acid substitutions or deletions, relative to the amino acid sequence shown in Tables 2-5, or encoded by a nucleotide sequence shown in Tables 6-7.

In yet another embodiment, the anti-IGFBP3 antibody molecule includes at least one, two, or three CDRs from a light chain variable region of an antibody described herein, e.g., an antibody chosen from any of any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequence.

In yet another embodiment, the anti-IGFBP3 antibody molecule includes at least one, two, or three CDRs (or collectively all of the CDRs) from a light chain variable region comprising an amino acid sequence shown in Tables 2-5 or encoded by a nucleotide sequence shown in Tables 6-7. In one embodiment, one or more of the CDRs (or collectively all of the CDRs) have one, two, three, four, five, six or more changes, e.g., amino acid substitutions or deletions, relative to the amino acid sequence shown in Tables 2-5, or encoded by a nucleotide sequence shown in Tables 6-7. In certain embodiments, the anti-IGFBP3 antibody molecule includes a substitution in a light chain CDR, e.g., one or more substitutions in a CDR1, CDR2 and/or CDR3 of the light chain.

In another embodiment, the anti-IGFBP3 antibody molecule includes at least one, two, three, four, five or six CDRs (or collectively all of the CDRs) from a heavy and light chain variable region comprising an amino acid sequence shown in Tables 2-5, or encoded by a nucleotide sequence shown in Tables 6-7. In one embodiment, one or more of the CDRs (or collectively all of the CDRs) have one, two, three, four, five, six or more changes, e.g., amino acid substitutions or deletions, relative to the amino acid sequence shown in Tables 2-5, or encoded by a nucleotide sequence shown in Tables 6-7.

In one embodiment, the anti-IGFBP3 antibody molecule includes all six CDRs from an antibody described herein, e.g., an antibody chosen from any of any of Yu139-A02, A03, B01, C01, C02, D02, D03, F02, G01, G03, H03; or as described in Tables 2-5, or encoded by the nucleotide sequence in Tables 6-7, or closely related CDRs, e.g., CDRs which are identical or which have at least one amino acid alteration, but not more than two, three or four alterations (e.g., substitutions, deletions, or insertions, e.g., conservative substitutions). In one embodiment, the anti-IGFBP3 antibody molecule may include any CDR described herein. In certain embodiments, the anti-IGFBP3 antibody molecule includes a substitution in a light chain CDR, e.g., one or more substitutions in a CDR1, CDR2 and/or CDR3 of the light chain. In another embodiment, the anti-IGFBP3 antibody molecule includes at least one, two, or three CDRs according to Kabat et al. (e.g., at least one, two, or three CDRs according to the Kabat definition as set out in Tables 2-5) from a heavy chain variable region of an antibody described herein, e.g., an antibody chosen from any of any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Tables 2-3.

In another embodiment, the anti-IGFBP3 antibody molecule includes at least one, two, or three CDRs according to Kabat et al. (e.g., at least one, two, or three CDRs according to the Kabat definition as set out in Tables 2-3) from a light chain variable region of an antibody described herein, e.g., an antibody chosen from any of any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs according to Kabat et al. shown in Tables 2-3.

In yet another embodiment, the anti-IGFBP3 antibody molecule includes at least one, two, three, four, five, or six CDRs according to Kabat et al. (e.g., at least one, two, three, four, five, or six CDRs according to the Kabat definition as set out in Tables 2-3) from the heavy and light chain variable regions of an antibody described herein, e.g., an antibody chosen from any of any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, three, four, five, or six CDRs according to Kabat et al. shown in Tables 2-3.

In yet another embodiment, the anti-IGFBP3 antibody molecule includes all six CDRs according to Kabat et al. (e.g., all six CDRs according to the Kabat definition as set out in Tables 2-3) from the heavy and light chain variable regions of an antibody described herein, e.g., an antibody chosen from any of any of Yu139-A02, A03, B01, C01, C02, D02, D03, F02, G01, G03, H03; or as described in Tables 2-5, or encoded by the nucleotide sequence in Tables 6-7; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to all six CDRs according to Kabat et al. shown in Tables 2-3. In one embodiment, the anti-IGFBP3 antibody molecule may include any CDR described herein.

In another embodiment, the anti-IGFBP3 antibody molecule includes at least one, two, or three Chothia or Kabat hypervariable loops (e.g., at least one, two, or three hypervariable loops according to the Chothia or Kabat definition as set out in Tables 2-5) from a heavy chain variable region of an antibody described herein, e.g., an antibody chosen from any of any of Yu139-A02, A03, B01, C01, C02, D02, D03, F02, G01, G03, H03; or as described in Tables 2-5, or encoded by the nucleotide sequence in Tables 6-7; or at least the amino acids from those hypervariable loops that contact IGFBP3; or which have at least one amino acid alteration, but not more than two, three or four alterations (e.g., substitutions, deletions, or insertions, e.g., conservative substitutions) relative to one, two, or three hypervariable loops according to Chothia et al. shown in Tables 2-5.

In another embodiment, the anti-IGFBP3 antibody molecule includes at least one, two, or three Chothia hypervariable loops (e.g., at least one, two, or three hypervariable loops according to the Chothia definition as set out in Tables 2-5) of a light chain variable region of an antibody described herein, e.g., an antibody chosen from any of any of Yu139-A02, A03, B01, C01, C02, D02, D03, F02, G01, G03, H03; or as described in Tables 2-5, or encoded by the nucleotide sequence in Tables 6-7; or at least the amino acids from those hypervariable loops that contact IGFBP3; or which have at least one amino acid alteration, but not more than two, three or four alterations (e.g., substitutions, deletions, or insertions, e.g., conservative substitutions) relative to one, two, or three hypervariable loops according to Chothia et al. shown in Tables 2-5.

In yet another embodiment, the anti-IGFBP3 antibody molecule includes at least one, two, three, four, five, or six hypervariable loops (e.g., at least one, two, three, four, five, or six hypervariable loops according to the Chothia definition as set out in Tables 2-5) from the heavy and light chain variable regions of an antibody described herein, e.g., an antibody chosen from any of any of Yu139-A02, A03, B01, C01, C02, D02, D03, F02, G01, G03, H03; or as described in Tables 2-5, or encoded by the nucleotide sequence in Tables 6-7; or at least the amino acids from those hypervariable loops that contact IGFBP3; or which have at least one amino acid alteration, but not more than two, three or four alterations (e.g., substitutions, deletions, or insertions, e.g., conservative substitutions) relative to one, two, three, four, five or six hypervariable loops according to Chothia et al. shown in Tables 2-5.

In one embodiment, the anti-IGFBP3 antibody molecule includes all six hypervariable loops (e.g., all six hypervariable loops according to the Chothia definition as set out in Tables 2-5) of an antibody described herein, e.g., an antibody chosen from any of any of Yu139-A02, A03, B01, C01, C02, D02, D03, F02, G01, G03, H03, or closely related hypervariable loops, e.g., hypervariable loops which are identical or which have at least one amino acid alteration, but not more than two, three or four alterations (e.g., substitutions, deletions, or insertions, e.g., conservative substitutions); or which have at least one amino acid alteration, but not more than two, three or four alterations (e.g., substitutions, deletions, or insertions, e.g., conservative substitutions) relative to all six hypervariable loops according to Chothia et al. shown in Tables 2-5. In one embodiment, the anti-IGFBP3 antibody molecule may include any hypervariable loop described herein.

In still another embodiment, the anti-IGFBP3 antibody molecule includes at least one, two, or three hypervariable loops that have the same canonical structures as the corresponding hypervariable loop of an antibody described herein, e.g., an antibody chosen from any of any of Yu139-A02, A03, B01, C01, C02, D02, D03, F02, G01, G03, H03, e.g., the same canonical structures as at least loop 1 and/or loop 2 of the heavy and/or light chain variable domains of an antibody described herein. See, e.g., Chothia et al., (1992) J. Mol. Biol. 227:799-817; Tomlinson et al., (1992) J. Mol. Biol. 227:776-798 for descriptions of hypervariable loop canonical structures. These structures can be determined by inspection of the tables described in these references.

In certain embodiments, the anti-IGFBP3 antibody molecule includes a combination of CDRs or hypervariable loops defined according to the Kabat et al. and Chothia et al.

In one embodiment, the anti-IGFBP3 antibody molecule includes at least one, two or three CDRs or hypervariable loops from a heavy chain variable region of an antibody described herein, e.g., an antibody chosen from any of any of Yu139-A02, A03, B01, C01, C02, D02, D03, F02, G01, G03, H03, according to the Kabat and Chothia definition (e.g., at least one, two, or three CDRs or hypervariable loops according to the Kabat and Chothia definition as set out in Tables 2-5); or encoded by the nucleotide sequence in Tables 6-7; or a sequence substantially identical (e.g., at least 80%, 85%, 90%, 92%, 95%, 97%, 98%, 99% or higher identical) to any of the aforesaid sequences; or which have at least one amino acid alteration, but not more than two, three or four alterations (e.g., substitutions, deletions, or insertions, e.g., conservative substitutions) relative to one, two, or three CDRs or hypervariable loops according to Kabat and/or Chothia shown in Tables 2-5.

For example, the anti-IGFBP3 antibody molecule can include VH CDR1 according to Kabat et al. or VH hypervariable loop 1 according to Chothia et al., or a combination thereof, e.g., as shown in Tables 2-5. The anti-IGFBP3 antibody molecule can further include, e.g., VH CDRs 2-3 according to Kabat et al. and VL CDRs 1-3 according to Kabat et al., e.g., as shown in Tables 2-5. Accordingly, in some embodiments, framework regions are defined based on a combination of CDRs defined according to Kabat et al. and hypervariable loops defined according to Chothia et al. For example, the anti-IGFBP3 antibody molecule can include VH FR1 defined based on VH hypervariable loop 1 according to Chothia et al. and VH FR2 defined based on VH CDRs 1-2 according to Kabat et al., e.g., as shown in Tables 2-5. The anti-IGFBP3 antibody molecule can further include, e.g., VH FRs 3-4 defined based on VH CDRs 2-3 according to Kabat et al. and VL FRs 1-4 defined based on VL CDRs 1-3 according to Kabat et al.

The anti-IGFBP3 antibody molecule can contain any combination of CDRs or hypervariable loops according to the Kabat and Chothia definitions. In one embodiment, the anti-IGFBP3 antibody molecule includes at least one, two or three CDRs from a light chain variable region of an antibody described herein, e.g., an antibody chosen from any of any of Yu139-A02, Yu139-A03, Yu139-B01, Yu139-C01, Yu139-C02, Yu139-D02, Yu139-D03, Yu139-F02, Yu139-G01, Yu139-G03, Yu139-H03, according to the Kabat and Chothia definition (e.g., at least one, two, or three CDRs according to the Kabat and Chothia definition as set out in Tables 2-5). Preferred anti-IGFBP3 antibodies are Yu139-A03, Yu139-C01, Yu139-H03 or Yu139-G03.

In an embodiment, e.g., an embodiment comprising a variable region, a CDR (e.g., Chothia CDR or Kabat CDR), or other sequence referred to herein, e.g., in Tables 2-5, the antibody molecule is a monospecific antibody molecule, a bispecific antibody molecule, or is an antibody molecule that comprises an antigen binding fragment of an antibody, e.g., a half antibody or antigen binding fragment of a half antibody. In embodiments the antibody molecule is a bispecific antibody molecule having a first binding specificity for IGFBP3 and a second binding specificity for TNF-alpha, integrin, IL1, IL12 and IL23, CD3, CD20, CD80, CD86.

In one embodiment, the anti-IGFBP3 antibody molecule includes:
  (i) a heavy chain variable region (VH) including a VHCDR1 amino acid sequence chosen from any one of SEQ ID NO: 1 to SEQ ID NO: 7; a VHCDR2 amino acid sequence chosen from any one of SEQ ID NO: 8 to SEQ ID NO: 16; and a VHCDR3 amino acid sequence chosen from any one of SEQ ID NO: 17 to SEQ ID NO: 26; and
  (ii) a light chain variable region (VL) including a VLCDR1 amino acid sequence chosen from any one of SEQ ID NO: 27 to SEQ ID NO: 36, a VLCDR2 amino acid sequence chosen from any one of SEQ ID NO: 37 to SEQ ID NO: 44, and a VLCDR3 amino acid sequence chosen from SEQ ID NO: 45 to SEQ ID NO: 54.

In another embodiment, the anti-IGFBP3 antibody molecule includes:
  (i) a heavy chain variable region (VH) including a VHCDR1 amino acid sequence chosen from SEQ ID NO: 2, SEQ ID NO: 4 or SEQ ID NO: 7; a VHCDR2 amino acid sequence of SEQ ID NO: 9, SEQ ID NO: 11, SEQ ID NO: 12 or SEQ ID NO: 16 and a VHCDR3 amino acid sequence of SEQ ID NO: 18, SEQ ID NO: 20, SEQ ID NO: 25 or SEQ ID NO: 26 and
  (ii) a light chain variable region (VL) including a VLCDR1 amino acid sequence of SEQ ID NO: 28, SEQ ID NO: 30, SEQ ID NO: 35, SEQ ID NO: 36, a VLCDR2 amino acid sequence of SEQ ID NO: 38, SEQ ID NO: 39, SEQ ID NO: 43, SEQ ID NO: 44 and a VLCDR3 amino acid sequence of SEQ ID NO: 46, SEQ ID NO: 48, SEQ ID NO: 53, SEQ ID NO: 54.

In one embodiment, the light or the heavy chain variable framework (e.g., the region encompassing at least FR1, FR2, FR3, and optionally FR4) of the anti-IGFBP3 antibody molecule can be chosen from: (a) a light or heavy chain variable framework including at least 80%, 85%, 87% 90%, 92%, 93%, 95%, 97%, 98%, or preferably 100% of the amino acid residues from a human light or heavy chain variable framework, e.g., a light or heavy chain variable framework residue from a human mature antibody, a human germline sequence, or a human consensus sequence; (b) a light or heavy chain variable framework including from 20% to 80%, 40% to 60%, 60% to 90%, or 70% to 95% of the amino acid residues from a human light or heavy chain variable framework, e.g., a light or heavy chain variable framework residue from a human mature antibody, a human germline sequence, or a human consensus sequence; (c) a non-human framework (e.g., a rodent framework); or (d) a non-human framework that has been modified, e.g., to remove antigenic or cytotoxic determinants, e.g., deimmunized, or partially humanized.

In one embodiment, the light or heavy chain variable framework region (particularly FR1, FR2 and/or FR3) includes a light or heavy chain variable framework sequence at least 70, 75, 80, 85, 87, 88, 90, 92, 94, 95, 96, 97, 98, 99% identical or identical to the frameworks of a VL or VH segment of a human germline gene.

In certain embodiments, the anti-IGFBP3 antibody molecule comprises a heavy chain variable domain having at least one, two, three, four, five, six, seven, ten, fifteen, twenty or more changes, e.g., amino acid substitutions or deletions.

In one embodiment, the heavy or light chain variable region, or both, of the anti-IGFBP3 antibody molecule includes an amino acid sequence encoded by a nucleic acid sequence described herein or a nucleic acid that hybridizes to a nucleic acid sequence described herein (e.g., a nucleic acid sequence as shown in Tables 6 and 7) or its complement, e.g., under low stringency, medium stringency, or high stringency, or other hybridization condition described herein.

In another embodiment, the anti-IGFBP3 antibody molecule comprises at least one, two, three, or four antigen-binding regions, e.g., variable regions, having an amino acid sequence as set forth in Tables 2-5, or a sequence substantially identical thereto (e.g., a sequence at least about 85%, 90%, 95%, 99% or more identical thereto, or which differs by no more than 1, 2, 5, 10, or 15 amino acid residues from the sequences shown in Tables 2-5. In another embodiment, the anti-IGFBP3 antibody molecule includes a VH and/or VL domain encoded by a nucleic acid having a nucleotide sequence as set forth in Tables 2-5, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 2-5.

In yet another embodiment, the anti-IGFBP3 antibody molecule comprises at least one, two, or three CDRs from a heavy chain variable region having an amino acid sequence as set forth in Tables 2-5, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-IGFBP3 antibody molecule comprises at least one, two, or three CDRs from a light chain variable region having an amino acid sequence as set forth in Tables 2-5, or a sequence substantially homologous thereto (e.g., a sequence at least about 85%, 90%, 95%, 99% or more identical thereto, and/or having one, two, three or more substitutions, insertions or deletions, e.g., conserved substitutions). In yet another embodiment, the anti-IGFBP3 antibody molecule comprises at least one, two, three, four, five or six CDRs from heavy and light chain variable regions having an amino acid sequence as set forth in Tables 2-5), or a sequence substantially homologous thereto (e.g., a sequence at least about 85%, 90%, 95%, 99% or more identical thereto, and/or having one, two, three or more substitutions, insertions or deletions, e.g., conserved substitutions).

In yet other embodiments, the anti-IGFBP3 antibody molecule has a heavy chain constant region (Fc) chosen from, e.g., the heavy chain constant regions of IgG1, IgG2, IgG3, IgG4, IgM, IgA1, IgA2, IgD, and IgE; particularly, chosen from, e.g., the heavy chain constant regions of IgG1, IgG2, IgG3, and IgG4, more particularly, the heavy chain constant region of IgG1 or IgG4 (e.g., human IgG1, IgG2 or IgG4). In one embodiment, the heavy chain constant region is human IgG1. In another embodiment, the anti-IGFBP3 antibody molecule has a light chain constant region chosen from, e.g., the light chain constant regions of kappa or lambda. In one embodiment, the constant region is altered, e.g., mutated, to modify the properties of the anti-IGFBP3 antibody molecule (e.g., to increase or decrease one or more of: Fc receptor binding, antibody glycosylation, the number of cysteine residues, effector cell function, complement function, half-life, aggregation and stability). In certain embodiments, the anti-IGFBP3 antibody molecules comprises a human IgG4 mutated In one embodiment, the anti-IGFBP3 antibody molecule is isolated or recombinant.

In one embodiment, the anti-IGFBP3 antibody molecule is a humanized or human antibody molecule.

The invention also features a nucleic acid molecule that comprise one or both nucleotide sequences that encode heavy and light chain variable regions, CDRs, hypervariable loops, framework regions of the anti-IGFBP3 antibody molecules, as described herein.

In certain embodiments, the nucleotide sequence that encodes the anti-IGFBP3 antibody molecule is codon optimized. For example, the invention features a first and second nucleic acid encoding heavy and light chain variable regions, respectively, of an anti-IGFBP3 antibody molecule chosen from one or more of, e.g., any of Yu139-A02, A03, B01, C01, C02, D02, D03, F02, G01, G03, H03, as summarized in Tables 2-5, or a sequence substantially identical thereto. For example, the nucleic acid can comprise a nucleotide sequence as set forth in Tables 6-7, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 6-7).

In other embodiments, the nucleic acid molecule comprises a nucleotide sequence that encodes a heavy chain variable domain and/or a heavy chain constant region comprising the amino acid sequence of any of Yu139-A02, A03, B01, C01, C02, D02, D03, F02, G01, G03, H03; or as described in Tables 2-5; or the nucleotide sequence in Tables 6-7; or a sequence substantially identical (e.g., a sequence at least about 85%, 90%, 95%, 99% or more identical) to any of the aforesaid sequences.

In other embodiments, the nucleic acid molecule comprises a nucleotide sequence that encodes a light chain variable domain and/or a light chain constant region comprising the amino acid sequence of any of Yu139-A02, A03, B01, C01, C02, D02, D03, F02, G01, G03, H03; or as described in Tables 2-5; or the nucleotide sequence in Tables 6-7; or a sequence substantially identical (e.g., a sequence at least about 85%, 90%, 95%, 99% or more identical) to any of the aforesaid sequences.

The aforesaid nucleotide sequences encoding the anti-IGFBP3 heavy and light chain variable domain and constant regions can be present in a separate nucleic acid molecule, or in the same nucleic acid molecule. In certain embodiments, the nucleic acid molecules comprise a nucleotide sequence encoding a leader sequence.

In certain embodiments, the nucleic acid molecule comprises a nucleotide sequence encoding at least one, two, or three CDRs, or hypervariable loops, from a heavy chain variable region having an amino acid sequence as set forth in Tables 2-5, or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule comprises a nucleotide sequence encoding at least one, two, or three CDRs, or hypervariable loops, from a light chain variable region having an amino acid sequence as set forth in Tables 2-5, or a sequence substantially homologous thereto (e.g., a sequence at least about 85%, 90%, 95%, 99% or more identical thereto, and/or having one, two, three or more substitutions, insertions or deletions, e.g., conserved substitutions).

In yet another embodiment, the nucleic acid molecule comprises a nucleotide sequence encoding at least one, two, three, four, five, or six CDRs, or hypervariable loops, from heavy and light chain variable regions having an amino acid sequence as set forth in Tables 2-5, or a sequence substantially homologous thereto (e.g., a sequence at least about 85%, 90%, 95%, 99% or more identical thereto, and/or having one, two, three or more substitutions, insertions or deletions, e.g., conserved substitutions).

In another embodiment, the nucleic acid molecule includes one or more heavy chain framework region (e.g., any of VHFW1 (type a), VHFW1 (type b), VHFW1 (type c), VHFW1 (type d), VHFW2 (type a), VHFW2 (type a'), VHFW2 (type b), VHFW2 (type c), VHFW2 (type d), VHFW2 (type e), VHFW3 (type a), VHFW3 (type b), VHFW3 (type c), VHFW3 (type d), VHFW3 (type e), or VHFW4, or any combination thereof, e.g., a framework combination as described herein) for any of Yu139-A02, A03, B01, C01, C02, D02, D03, F02, G01, G03, H03, as summarized in Tables 2-5, or a sequence substantially identical thereto. For example, the nucleic acid molecule can comprise a nucleotide sequence as set forth in Tables 6-7, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 6-7).

In another embodiment, the nucleic acid molecule includes one or more light chain framework region (e.g., any of VLFW1 (type a), VLFW1 (type b), VLFW1 (type c), VLFW1 (type d), VLFW1 (type e), VLFW1 (type f), VLFW2 (type a), VLFW2 (type c), VLFW3 (type a), VLFW3 (type b), VLFW3 (type c), VLFW3 (type d), VLFW3 (type e), VLFW3 (type f), VLFW3 (type g), or VLFW4, or any combination thereof, e.g., a framework combination as described herein) for of any of Yu139-A02, A03, B01, C01, C02, D02, D03, F02, G01, G03, H03, as summarized in Tables 2-5, or a sequence substantially identical thereto. For example, the nucleic acid molecule can comprise a nucleotide sequence as set forth in Tables 6-7, or a sequence substantially identical thereto (e.g., a sequence at least about 85%, 90%, 95%, 99% or more identical thereto, or which differs by no more than 3, 6, 15, 30, or 45 nucleotides from the sequences shown in Tables 6-7).

In another embodiment, the nucleic acid molecule includes one or more heavy chain framework region and one or more light chain framework region as described herein. The heavy and light chain framework regions may be present in the same vector or separate vectors.

In another aspect, the application features host cells and vectors containing the nucleic acids described herein or modified for codon optimization according to known methods. The nucleic acids may be present in a single vector or separate vectors present in the same host cell or separate host cell. The host cell can be a eukaryotic cell, e.g., a mammalian cell, an insect cell, a yeast cell, or a prokaryotic cell, e.g., E. coli. For example, the mammalian cell can be a cultured cell or a cell line. Exemplary mammalian cells include lymphocytic cell lines (e.g., NSO), Chinese hamster ovary cells (CHO), COS cells, oocyte cells, and cells from a transgenic animal, e.g., mammary epithelial cell.

In one aspect, the invention features a method of providing an antibody molecule described herein. The method includes: providing a IGFBP3 antigen (e.g., an antigen comprising at least a portion of a IGFBP3 epitope); obtaining an antibody molecule that specifically binds to the IGFBP3 polypeptide; and evaluating if the antibody molecule specifically binds to the IGFBP3 polypeptide, or evaluating efficacy of the antibody molecule in modulating, e.g., inhibiting, the activity of the IGFBP3. The method can further include administering the antibody molecule to a subject, e.g., a human or non-human animal.

In another aspect, the invention provides, compositions, e.g., pharmaceutical compositions, which include a pharmaceutically acceptable carrier, excipient or stabilizer, and at least one of the anti-IGFBP3 antibody molecules described herein. In one embodiment, the composition, e.g., the pharmaceutical composition, includes a combination of the antibody molecule and one or more agents, e.g., a therapeutic agent or other antibody molecule, as described herein. In one embodiment, the antibody molecule is conjugated to a label or a therapeutic agent.

The anti-IGFBP3 antibody molecules disclosed herein can inhibit, reduce or neutralize one or more activities of IGFBP3 as indicated above. Thus, such antibody molecules can be used to treat or prevent disorders where the inhibition, reduction or neutralization of IGFBP3-induced activities in a subject is desired.

Uses of the Anti-IGFBP3 Antibody Molecules

The present antibodies are used in methods of treatment of various disorders or conditions such as diabetes, as well as intestinal bowel diseases, malabsorption syndrome, inflammatory bowel disease, cachexia, Crohn's disease, ulcerative colitis, celiac disease, diabetic enteropathy.

Accordingly, in another aspect, a method of modulating the IGFBP3/TMEM219 axis in a subject is provided. The method comprises administering to the subject an anti-IGFBP3 antibody molecule disclosed herein (e.g., a therapeutically effective amount of an anti-IGFBP3 antibody molecule), alone or in combination with one or more agents or procedures, such that the IGFBP3/TMEM219 axis in the subject is modulated. In one embodiment, the antibody molecule inhibits, reduce or neutralize or block the IGFBP3/TMEM219 axis activity in the subject. The subject can be a mammal, e.g., a primate, preferably a higher primate, e.g., a human (e.g., a patient having, or at risk of having, a disorder described herein). In one embodiment, the subject is in need of inhibiting, reducing, neutralizing or blocking the IGFBP3/TMEM219 axis. In one embodiment, the subject has, or is at risk of, having a disorder described herein, e.g, diabetes, or inflammatory bowel disorder (IBD), malabsorption syndrome, irritable bowel disease, cachexia, celiac disease, diabetic enteropathy as described herein.

BRIEF DESCRIPTION OF THE DRAWINGS

FIG. 1A provides a schematic of the assay. In this ELISA, the plate is coated with LSBIO anti-IGFBP3 monoclonal antibody (capture antibody). Then a premix of IGFBP3 and ecto-TMEM219 is added. IGFBP3 in the IGFBP3/ecto-TMEM219 complex should bind to the commercial LSBio antibody on the plate. If the capture antibody competes with ecto-TMEM219, the ecto-TMEM219 should be displaced from the complex and removed with washing. Detection of bound TMEM219 is performed with an anti-His tag reagent (ecto-TMEM219 has the His tag); if ecto-TMEM219 is displaced, absorbance is low. FIG. 1B shows the results. The leftmost three bars show various controls. In each case the commercial LSBio anti-IGFBP3 is coated on the plate. In the first control experiment (leftmost bar), IGFBP3/ecto-TMEM219 mix is omitted to control for nonspecific binding of the anti-His tag to the plate or the commercial anti-IGFBP3 antibody coated on the plate. In the second control experiment, only IGFBP3 is omitted to control for nonspecific binding of ecto-TMEM219 to the plate or to the LSBio anti-IGFBP3 capture antibody. In the third control, ecto-TMEM219 is omitted, to control for nonspecific binding of the anti-His tag to IGFBP3. The rightmost bar shows absorbance after addition of IGFBP3:TMEM-219 (1:1) complex. The high absorbance indicates that the LSBio antibody does not compete with ecto-TMEM219 for binding to IGFBP3.

DETAILED DESCRIPTION OF THE INVENTION

Figure 1:
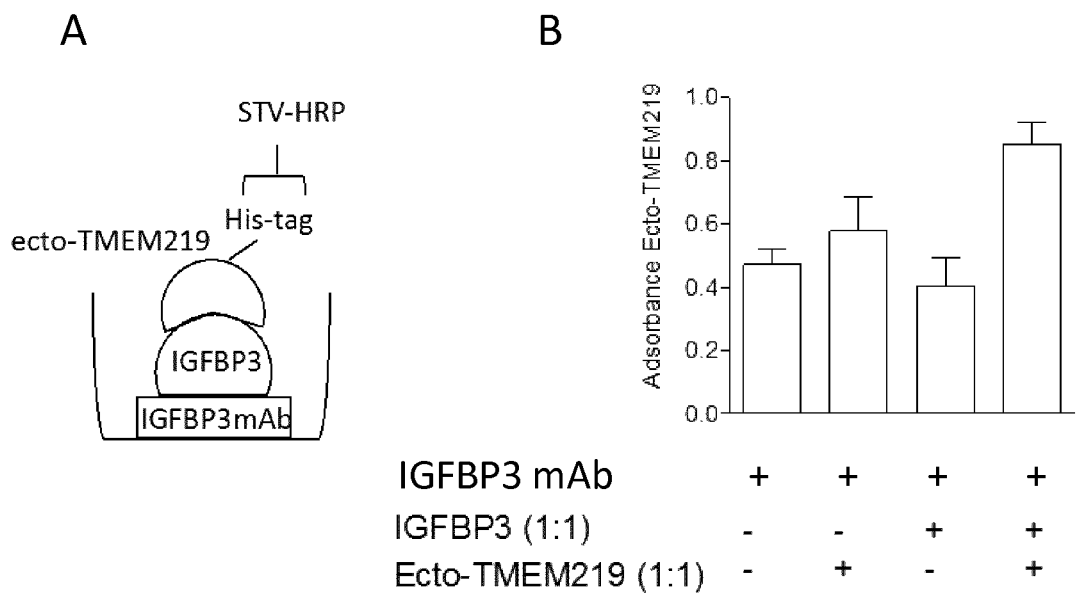
FIGS. 1A-1B. Commercial monoclonal antibody anti-IGFBP3 (LSBIO LSC45037 clone 83.8F9) binds IGFBP3 but does not inhibit the interaction with the extracellular domain of TMEM219.

The antibodies of the invention include antibodies that specifically bind IGFBP3. As discussed herein, these antibodies are collectively referred to as "anti-IGFBP3 antibodies". Thus, by "anti-IGFBP3 antibodies" is intended antibodies specific for IGFBP3. All of these antibodies are encompassed by the discussion herein. The respective antibodies can be used alone or in combination in the methods of the invention.

By "antibodies that specifically bind" is intended that the antibodies will not substantially cross react with another polypeptide. By "not substantially cross react" is intended that the antibody or fragment has a binding affinity for a non-homologous protein which is less than 10%, more preferably less than 5%, and even more preferably less than 1%, of the binding affinity for IGFBP3.

As used herein, the term "antigen binding molecule" refers in its broadest sense to a molecule that specifically binds an antigenic determinant. Examples of antigen binding molecules are antibodies, antibody fragments and scaffold antigen binding proteins.

The term "antigen binding moiety" refers to a polypeptide molecule that specifically binds to an antigenic determinant. In one aspect, the antigen binding moiety is able to activate signaling through its target cell antigen. In a particular aspect, the antigen binding moiety is able to direct the entity to which it is attached to a target site. Antigen binding moieties include antibodies and fragments thereof capable of specific binding to a target cell antigen. In addition, antigen binding moieties capable of specific binding to a target cell antigen include scaffold antigen binding proteins as defined herein below, e.g. binding domains which are based on designed repeat proteins or designed repeat domains such as designed ankyrin repeat proteins (DARPins) (see e.g. WO 2002/020565) or Lipocalins (Anticalin).

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

Additional terms are defined below and throughout the application.

The term "antibody" is intended to refer to immunoglobulin molecules comprising at least one heavy (H) chain or at least one light (L) chain. Said chains may be inter-connected by disulfide bonds. The term "antibody" also comprises multimers of said chains (e.g., IgM). Each heavy chain comprises a heavy chain variable region (abbreviated herein as HCVR or VH) and a heavy chain constant region. The heavy chain constant region comprises three domains, CH1, CH2 and CH3. Each light chain comprises a light chain variable region (abbreviated herein as LCVR or VL) and a light chain constant region. The light chain constant region comprises one domain (CL1). The VH and VL regions can be further subdivided into regions of hypervariability, termed complementarity determining regions (CDRs), interspersed with regions that are more conserved, termed framework regions (FR). Each VH and VL is composed of at least one CDR, preferably three CDRs and at least one FR, preferably four FRs, arranged from amino-terminus to carboxy-terminus in the following order: FR1, CDR1, FR2, CDR2, FR3, CDR3, FR4. In some embodiments, the FRs of the antibody (or antigen-binding portion thereof) may be identical to the human germline sequences or may be naturally or artificially modified. An amino acid consensus sequence may be defined based on a side-by-side analysis of two or more CDRs.

The term "antibody," as used herein, also includes ADC (antibody drug conjugate), payload fusion antibodies, bispecific, Fab, scFv, diabodies, triabodies, minibodies and single domain antibodies, camelid IgG, IgNAR, as described in (25) incorporated by reference.

The term "antibody," as used herein, also includes antigen-binding fragments of full antibody molecules. The terms "antigen-binding portion" of an antibody, "antigen-binding fragment" of an antibody, and the like, as used herein, include any naturally occurring, enzymatically obtainable, synthetic, or genetically engineered polypeptide or glycoprotein that specifically binds an antigen to form a complex. Antigen-binding fragments of an antibody may be derived, e.g., from full antibody molecules using any suitable standard techniques such as proteolytic digestion or recombinant genetic engineering techniques involving the manipulation and expression of DNA encoding antibody variable and optionally constant domains. Such DNA is known and/or is readily available from, e.g., commercial sources, DNA libraries (including, e.g., phage-antibody libraries), or can be synthesized. The DNA may be sequenced and manipulated chemically or by using molecular biology techniques, for example, to arrange one or more variable and/or constant domains into a suitable configuration, or to introduce codons, create cysteine residues, modify, add or delete amino acids, etc.

Designed Ankyrin Repeat Proteins (DARPins) are derived from Ankyrin which is a family of proteins that mediate attachment of integral membrane proteins to the cytoskeleton.

A single ankyrin repeat is a 33-residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100 (4), 1700-1705 (2003) and J. Mol. Biol. 369, 1015-1028 (2007) and US20040132028.

A single-domain antibody is an antibody fragment consisting of a single monomeric variable antibody domain. The first single domain was derived from the variable domain of the antibody heavy chain from camelids (nanobodies or VHH fragments). Furthermore, the term single-domain antibody includes an autonomous human heavy chain variable domain (aVH) or VNAR fragments derived from sharks.

Non-limiting examples of antigen-binding fragments include: (i) Fab fragments; (ii) F(ab')2 fragments; (iii) Fd fragments; (iv) Fv fragments; (v) single-chain Fv (scFv) molecules; (vi) dAb fragments; and (vii) minimal recognition units consisting of the amino acid residues that mimic the hypervariable region of an antibody (e.g., an isolated complementarity determining region (CDR) such as a CDR3 peptide), or a constrained FR3-CDR3-FR4 peptide. Other engineered molecules, such as domain-specific antibodies, single domain antibodies, domain-deleted antibodies, chimeric antibodies, CDR-grafted antibodies, diabodies, triabodies, tetrabodies, minibodies, nanobodies (e.g., monovalent nanobodies, and bivalent nanobodies), small modular immunopharmaceuticals (SMIPs), and shark variable IgNAR domains, are also encompassed within the expression "antigen-binding fragment," as used herein.

An antigen-binding fragment of an antibody will typically comprise at least one variable domain. The variable domain may be of any size or amino acid composition and will generally comprise at least one CDR which is adjacent to or in frame with one or more framework sequences. In antigen-binding fragments having a VH domain associated with a VL domain, the VH and VL domains may be situated relative to one another in any suitable arrangement. For example, the variable region may be dimeric and contain VH-VH, VH-VL or VL-VL dimers. Alternatively, the antigen-binding fragment of an antibody may contain a monomeric VH or VL domain.

In certain embodiments, an antigen-binding fragment of an antibody may contain at least one variable domain covalently linked to at least one constant domain. Non-limiting, exemplary configurations of variable and constant domains that may be found within an antigen-binding fragment of an antibody include: (i) VH-CH1; (ii) VH-CH2; (iii) VH-CH3; (iv) VH-CH1-CH2; (v) VH-CH1-CH2-CH3; (vi) VH-CH2-CH3; (vii) VH-CL; (viii) VL-CH1; (ix) VL-CH2; (x) VL-CH3; (xi) VL-CH1-CH2; (xii) VL-CH1-CH2-CH3; (xiii) VL-CH2-CH3; and (xiv) VL-CL. In any configuration of variable and constant domains, including any of the exemplary configurations listed above, the variable and constant domains may be either directly linked to one another or may be linked by a full or partial hinge or linker region. A hinge region may in various embodiments consist of at least 2 (e.g., 5, 10, 15, 20, 40, 60 or more) amino acids which result in a flexible or semi-flexible linkage between adjacent variable and/or constant domains in a single polypeptide molecule. Moreover, an antigen-binding fragment of an antibody may in various embodiments comprise a homo-dimer or hetero-dimer (or other multimer) of any of the variable and constant domain configurations listed above in non-covalent association with one another and/or with one or more monomeric VH or VL domain (e.g., by disulfide bond(s)).

In certain embodiments, antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. TIBTECH 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in antigen binding molecules may be made in order to create variants with certain improved properties. In one aspect, variants of antigen binding molecules are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). Further variants of antigen binding molecules of the invention include those with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain embodiments, it may be desirable to create cysteine engineered variants of the antigen binding molecule of the invention, e.g., "thioMAbs," in which one or more residues of the molecule are substituted with cysteine residues. In particular embodiments, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate.

In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

In certain aspects, the antigen binding molecules provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-l,3,6-trioxane, ethylene/maleic anhydride copolymer, polyaminoacids (either homopolymers or random copolymers), and dextran or poly(n-vinyl pyrrolidone)polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc. In another aspect, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed. In another aspect, immunoconjugates of the antigen binding molecules provided herein may be obtained. An "immunoconjugate" is an antibody conjugated to one or more heterologous molecule(s), including but not limited to a cytotoxic agent.

As with full antibody molecules, antigen-binding fragments may be monospecific or multispecific (e.g., bispecific). A multispecific antigen-binding fragment of an antibody will typically comprise at least two different variable domains, wherein each variable domain is capable of specifically binding to a separate antigen or to a different epitope on the same antigen. Any multispecific antibody format, including the exemplary bispecific antibody formats disclosed herein, may in various embodiments be adapted for use in the context of an antigen-binding fragment of an anti-IL-6R antibody using routine techniques available in the art.

The constant region of an antibody is important in the ability of an antibody to fix complement and mediate cell-dependent cytotoxicity. Thus, the isotype of an antibody may be selected on the basis of whether it is desirable for the antibody to mediate cytotoxicity.

The term "human antibody", as used herein, is intended to include antibodies having variable and constant regions derived from human germline immunoglobulin sequences. The human antibodies featured in the invention may in various embodiments nonetheless include amino acid residues not encoded by human germline immunoglobulin sequences (e.g., mutations introduced by random or site-specific mutagenesis in vitro or by somatic mutation in vivo), for example in the CDRs and in in some embodiments CDR3. However, the term "human antibody", as used herein, is not intended to include antibodies in which CDR sequences derived from the germline of another mammalian species, such as a mouse, have been grafted onto human framework sequences.

The term "recombinant human antibody", as used herein, is intended to include all human antibodies that are prepared, expressed, created or isolated by recombinant means, such as antibodies expressed using a recombinant expression vector transfected into a host cell (described further below), antibodies isolated from a recombinant, combinatorial human antibody library (described further below), antibodies isolated from an animal (e.g., a mouse) that is transgenic for human immunoglobulin genes (see e.g., Taylor et al. (1992) Nucl. Acids Res.20:6287-6295, incorporated herein by reference in its entirety) or antibodies prepared, expressed, created or isolated by any other means that involves splicing of human immunoglobulin gene sequences to other DNA sequences. Such recombinant human antibodies have variable and constant regions derived from human germline immunoglobulin sequences. In certain embodiments, however, such recombinant human antibodies are subjected to in vitro mutagenesis (or, when an animal transgenic for human Ig sequences is used, in vivo somatic mutagenesis) and thus the amino acid sequences of the VH and VL regions of the recombinant antibodies are sequences that, while derived from and related to human germline VH and VL sequences, may not naturally exist within the human antibody germline repertoire in vivo.

Human antibodies can exist in two forms that are associated with hinge heterogeneity.

In an embodiment, an immunoglobulin molecule comprises a stable four chain construct of approximately 150-160 kDa in which the dimers are held together by an interchain heavy chain disulfide bond. In another embodiment, the dimers are not linked via interchain disulfide bonds and a molecule of about 75-80 kDa is formed composed of a covalently coupled light and heavy chain (half-antibody). These embodiments/forms have been extremely difficult to separate, even after affinity purification. The frequency of appearance of the second form in various intact IgG isotypes is due to, but not limited to, structural differences associated with the hinge region isotype of the antibody. A single amino acid substitution in the hinge region of the human IgG4 hinge can significantly reduce the appearance of the second form (Angal et al. (1993) Molecular Immunology 30:105) to levels typically observed using a human IgG1 hinge. The instant invention encompasses in various embodiments antibodies having one or more mutations in the hinge, CH2 or CH3 region which may be desirable, for example, in production, to improve the yield of the desired antibody form.

An "isolated antibody," as used herein, means an antibody that has been identified and separated and/or recovered from at least one component of its natural environment. For example, an antibody that has been separated or removed from at least one component of an organism, or from a tissue or cell in which the antibody naturally exists or is naturally produced, is an "isolated antibody." In various embodiments, the isolated antibody also includes an antibody in situ within a recombinant cell. In other embodiments, isolated antibodies are antibodies that have been subjected to at least one purification or isolation step. In various embodiments, an isolated antibody may be substantially free of other cellular material and/or chemicals.

The term "specifically binds," or the like, means that an antibody or antigen-binding fragment thereof forms a complex with an antigen that is relatively stable under physiologic conditions. Methods for determining whether an antibody specifically binds to an antigen are well known in the art and include, for example, equilibrium dialysis, surface plasmon resonance, and the like. For example, an antibody that "specifically binds" IGFBP3, as used herein, includes antibodies that bind IGFBP3 or portion thereof with a KD of less than about 1000 nM, less than about 500 nM, less than about 300 nM, less than about 200 nM, less than about 100 nM, less than about 90 nM, less than about 80 nM, less than about 70 nM, less than about 60 nM, less than about 50 nM, less than about 40 nM, less than about 30 nM, less than about 20 nM, less than about 10 nM, less than about 5 nM, less than about 4 nM, less than about 3 nM, less than about 2 nM, less than about 1 nM or about 0.5 nM, as measured in a surface plasmon resonance assay.

The term "surface plasmon resonance", as used herein, refers to an optical phenomenon that allows for the analysis of real-time interactions by detection of alterations in protein concentrations within a biosensor matrix, for example using the BIAcore™ system (Biacore Life Sciences division of GE Healthcare, Piscataway, NJ) or kinetic exclusion assays.

The term "KD", as used herein, is intended to refer to the equilibrium dissociation constant of an antibody-antigen interaction.

The term "epitope" refers to an antigenic determinant that interacts with a specific antigen binding site in the variable region of an antibody molecule known as a paratope. A single antigen may have more than one epitope. Thus, different antibodies may bind to different areas on an antigen and may have different biological effects. Epitopes may be either conformational or linear. A conformational epitope is produced by spatially juxtaposed amino acids from different segments of the linear polypeptide chain. A linear epitope is one produced by adjacent amino acid residues in a polypeptide chain. In certain circumstance, an epitope may include moieties of saccharides, phosphoryl groups, or sulfonyl groups on the antigen.

The anti-IGFBP3 antibodies useful for the methods featured herein may in various embodiments include one or more amino acid substitutions, insertions and/or deletions in the framework and/or CDR regions of the heavy and light chain variable domains as compared to the corresponding germline sequences from which the antibodies were derived. Such mutations can be readily ascertained by comparing the amino acid sequences disclosed herein to germline sequences available from, for example, public antibody sequence databases. The present invention includes in various embodiments methods involving the use of antibodies, and antigen-binding fragments thereof, which are derived from any of the amino acid sequences disclosed herein, wherein one or more amino acids within one or more framework and/or CDR regions are mutated to the corresponding residue(s) of the germline sequence from which the antibody was derived, or to the corresponding residue(s) of another human germline sequence, or to a conservative amino acid substitution of the corresponding germline residue(s) (such sequence changes are referred to herein collectively as "germline mutations"). Numerous antibodies and antigen-binding fragments may be constructed which comprise one or more individual germline mutations or combinations thereof. In certain embodiments, all of the framework and/or CDR residues within the VH and/or VL domains are mutated back to the residues found in the original germline sequence from which the antibody was derived. In other embodiments, only certain residues are mutated back to the original germline sequence, e.g., only the mutated residues found within the first 8 amino acids of FR1 or within the last 8 amino acids of FR4, or only the mutated residues found within CDR1, CDR2 or CDR3. In other embodiments, one or more of the framework and/or CDR residue(s) are mutated to the corresponding residue(s) of a different germline sequence (i.e., a germline sequence that is different from the germline sequence from which the antibody was originally derived). Furthermore, the antibodies may contain any combination of two or more germline mutations within the framework and/or CDR regions, e.g., wherein certain individual residues are mutated to the corresponding residue of a certain germline sequence while certain other residues that differ from the original germline sequence are maintained or are mutated to the corresponding residue of a different germline sequence. Once obtained, antibodies and antigen-binding fragments that contain one or more germline mutations can be easily tested for one or more desired property such as, improved binding specificity, increased binding affinity, improved or enhanced antagonistic or agonistic biological properties (as the case may be), reduced immunogenicity, etc. The use of antibodies and antigen-binding fragments obtained in this general manner are encompassed within the present invention.

The present invention also includes methods involving the use of anti-IGFBP3 antibodies comprising variants of any of the HCVR, LCVR, and/or CDR amino acid sequences disclosed herein having one or more conservative substitutions. For example, the present invention includes the use of anti-IL-6R antibodies having HCVR, LCVR, and/or CDR amino acid sequences with, e.g., 10 or fewer, 8 or fewer, 6 or fewer, 4 or fewer, etc. conservative amino acid substitutions relative to any of the HCVR, LCVR, and/or CDR amino acid sequences disclosed herein.

The term "bioequivalent" as used herein, refers to a molecule having similar bioavailability (rate and extent of availability) after administration at the same molar dose and under similar conditions (e.g., same route of administration), such that the effect, with respect to both efficacy and safety, can be expected to be essentially same as the comparator molecule. Two pharmaceutical compositions comprising an anti-IGFBP3 antibody are bioequivalent if they are pharmaceutically equivalent, meaning they contain the same amount of active ingredient (e.g., IGFBP3 antibody), in the same dosage form, for the same route of administration and meeting the same or comparable standards. Bioequivalence can be determined, for example, by an in vivo study comparing a pharmacokinetic parameter for the two compositions. Parameters commonly used in bioequivalence studies include peak plasma concentration (Cmax) and area under the plasma drug concentration time curve (AUC).

The invention in certain embodiments relates to methods comprising administering to the subject an antibody which comprises the heavy chain variable region comprising a sequence chosen from the group of: SEQ ID NO:55 to SEQ ID NO:65 and the light chain variable region comprising a sequence chosen from the group of: SEQ ID NO:66 to SEQ ID NO:76. The disclosure provides pharmaceutical compositions comprising such antibody, and methods of using these compositions.

The antibody is administered to the subject in various embodiments in a formulation comprising suitable carriers, excipients, and other agents to provide improved transfer, delivery, tolerance, and the like, and suitable for an intravenous or subcutaneous injection.

The injectable preparations may be prepared by methods publicly known. For example, injectable preparations may be prepared, e.g., by dissolving, suspending or emulsifying the antibody or its salt described above in a sterile aqueous medium or an oily medium conventionally used for injections. As the aqueous medium for injections, there are, for example, physiological saline, an isotonic solution containing glucose and other auxiliary agents, etc., which may be used in combination with an appropriate solubilizing agent such as an alcohol (e.g., ethanol), a polyalcohol (e.g., propylene glycol, polyethylene glycol), a nonionic surfactant [e.g., polysorbate 20 or 80, HCO-50 (polyoxyethylene (50 mol) adduct of hydrogenated castor oil)], etc. As the oily medium, there are employed, e.g., sesame oil, soybean oil, etc., which may be used in combination with a solubilizing agent such as benzyl benzoate, benzyl alcohol, etc. The injectable preparation thus prepared can be filled in an appropriate ampoule.

The antibody according to the invention can be administered to the subject using any acceptable device or mechanism. For example, the administration can be accomplished using a syringe and needle or with a reusable pen and/or autoinjector delivery device.

The methods of the present invention include the use of numerous reusable pen and/or autoinjector delivery devices to administer an antibody (or pharmaceutical formulation comprising the antibody). Examples of such devices include, but are not limited to AUTOPEN™ (Owen Mumford, Inc., Woodstock, UK), DISETRONIC™ pen (Disetronic Medical Systems, Bergdorf, Switzerland), HUMALOG MIX 75/25™ pen, HUMALOG™ pen, HUMALIN 70/30™ pen (Eli Lilly and Co., Indianapolis, IN), NOVOPEN™ I, II and III (Novo Nordisk, Copenhagen, Denmark), NOVOPEN JUNIOR™ (Novo Nordisk, Copenhagen, Denmark), BD™ pen (Becton Dickinson, Franklin Lakes, NJ), OPTIPEN™, OPTIPEN PRO™, OPTIPEN STARLET™, and OPTICLIK™ (Sanofi-Aventis, Frankfurt, Germany), to name only a few. Examples of disposable pen and/or autoinjector delivery devices having applications in subcutaneous delivery of a pharmaceutical composition of the present invention include, but are not limited to, the SOLOSTAR™ pen (Sanofi-Aventis), the FLEXPEN™ (Novo Nordisk), and the KWIKPEN™ (Eli Lilly), the SURECLICK™ Autoinjector (Amgen, Thousand Oaks, CA), the PENLET™ (Haselmeier, Stuttgart, Germany), the EPIPEN (Dey, L. P.), the HUMIRA™ Pen (Abbott Labs, Abbott Park, IL), the DAI® Auto Injector (SHL Group) and any auto-injector featuring the PUSHCLICK™ technology (SHL Group), to name only a few.

In one embodiment, the antibody is administered with a prefilled syringe. In another embodiment, the antibody is administered with a prefilled syringe containing a safety system. For example, the safety system prevents an accidental needlestick injury. In various embodiments, the antibody is administered with a prefilled syringe containing an ERIS™ safety system (West Pharmaceutical Services Inc.). See also U.S. Pat. Nos. 5,215,534 and 9,248,242, incorporated herein by reference in their entireties. In another embodiment, the antibody is administered with an auto-injector. In various embodiments, the antibody is administered with an auto-injector featuring the PUSHCLICK™ technology (SHL Group). In various embodiments, the auto-injector is a device comprising a syringe that allows for administration of a dose of the composition and/or antibody to a subject. See also U.S. Pat. Nos. 9,427,531 and 9,566,395, incorporated herein by reference in their entireties.

According to the invention, "subject" means a human subject or human patient.

EXAMPLES

Methods
Patients and Study Design
Healthy subjects (CTRL) were enrolled (n=10) among patients undergoing to colonoscopy or intestinal surgery for diverticulosis, colon cancer, irritable bowel syndrome. Age: 41.3±2.2 (mean±SEM); Sex (M/F): 7/3.

IBD individuals had a 5-year history of Crohn's disease and were enrolled at the moment of surgery procedure for disease complications (strictures, fistulas) or during an endoscopy routine examination before undergoing surgery. Age: 47.1±3.1 (mean±SEM); Sex (M/F): 4/6.

DE serum was obtained from n=10 individuals with long-standing type 1 diabetes (history of diabetes >20 years), intestinal symptoms and motility dysfunction, with age ranging from 41 to 43 years old, and pooled for in vitro experiments. All subjects provided informed consent before study enrollment.

Recombinant Proteins and Interventional Studies

Recombinant human IGFBP3 was obtained from Life Technologies (IGFBP3, Life Technologies, 10430H07H5). ecto-TMEM219 was obtained through Genescript's customized protein service. The protein, produced in E. coli, has the following amino acid sequence, (SEQ ID NO: 104)
THRTGLRSPDIPQDWVSFLRSFGQLTLCPRNGTVTGKWRGSHVVGLLTT

LNFGDGPDRNKTRTFQATVLGSQMGLKGSSAGQLVLITARVTTERTAGT

CLYFSAVPGILPSSQPPISCSEEGAGNATLSPRMGEECVSVWSHEGLVL

TKLLTSEELALCGSR.

IGFBP3 at 50 ng/ml and ecto-TMEM219 at 130 ng/ml were added to culture medium at day +1 from mini-guts culture (see below).

Monoclonal and polyclonal anti-IGFBP3 (LSBio LS-C45037/107162 mouse IgG1 clone 83.8F9; LSBIO LS-C149975/72664, goat IgG) were added to culture medium at day +1 from mini-guts culture at 1, 10, 50 ug/ml and at 10 ug/ml final concentration respectively. Newly generated anti-IGFBP3 monoclonal antibodies were added at 1:1 molecular ratio as compared to IGFBP3 at 10 ug/ml final concentration.

Crypts Isolation and Mini-Guts Development

Crypts were extracted from mucosa and sub-mucosa of intestinal samples of healthy subjects (healthy controls) or obtained from patients with established Crohn's disease undergoing surgery for disease complications (strictures, fistulae). Mucosa was incubated with a mixture of antibiotics Normocin, [Invivogen, San Diego, California 92121, USA ant-nr], Gentamycin [Invitrogen, Carlsbad, CA, USA ant-gn] and Fungizone [Invitrogen 15290018]) for 15 minutes at room temperature, and then tissue was minced into small pieces and incubated with 10 mM Dithiothreitol (DTT) (Sigma) in PBS 2-3 times for several minutes. Samples were then transferred to 8 mM EDTA in PBS and incubated for 30 minutes at 37° C. After this step, vigorous shaking of the sample yielded supernatants enriched in colonic crypts. Fetal bovine serum (FBS, Sigma 12103C-500 ML) was added to a final concentration of 5%, and single cells were removed by centrifugation 40×g for 2 minutes. Crypts were mixed with 50 µl of Matrigel (BD Biosciences 354234) and plated on pre-warmed culture dishes. After solidification, crypts were overlaid with complete crypt culture medium: Wnt3a-conditioned medium and Advanced DMEM/F12 (Life Technologies 1263010) 50:50, supplemented with Glutamax, 10 mM (Life Technologies 35050038) HEPES (Life Technologies 15630080), N-2 [1×] (Life Technologies 17502048), B-27 without retinoic acid [1×] (Life Technologies 12587010), 10 mM Nicotinamide (Sigma N0636), 1 mM N-Acetyl-L-cysteine (Sigma A965), 50 ng/ml human EGF (Life Technologies PHG0311), 1 µg/ml RSPO1 (Sino Biological 11083-H08H), 100 ng/ml human Noggin (Peprotech 12010C), 1 µg/ml Gastrin (Sigma-Aldrich SCP0152), 500 nM LY2157299 (Axon MedChem 1491), 10 µM SB202190 (Sigma S7067) and 0.01 µM PGE2 (Sigma P6532). Isolated crypts have been cultured for 8 days with/without recombinant proteins/Antibodies as described in the Recombinant proteins and interventional studies section. After 8 days, crypts were collected, and the morphology, mini-gut growth, expression of intestinal signature markers (EphB2, LGR5, h-TERT), and Caspase 8 (Life Technologies) were examined using RT-PCR. Percentage of developed mini-guts with at least one crypt domain was assessed as already described (4,18).

In Vitro Mini-Gut Generation Study

Crypts were isolated from healthy subject biopsy samples and cultured as previously described to generate mini-guts. To mimic the pathologic conditions, the crypt culturing medium was modified by adding human serum of individuals with diabetic enteropathy (DE), namely "DE" medium, in place of regular FBS, L-Wnt3 cells were grown in 10% "DE" serum to generate conditioned medium that was further added 50:50 to Advanced DMEM/F12 medium in order to obtain the crypts culture medium as described above (see Crypts isolation and mini-guts development). After 8 days, crypts were collected, and the morphology, mini-gut growth, expression of intestinal signature markers (EphB2, LGR5, h-TERT), and Caspase 8 (Life Technologies) were examined using RT-PCR. This has been established as model of intestinal stem cells-damage (4).

qRT-PCR Analysis

RNA from purified intestinal crypts was extracted using Trizol Reagent (Invitrogen), and qRT-PCR analysis was performed using TaqMan assays (Life Technologies, Grand Island, NY) according to the manufacturer's instructions. The normalized expression values were determined using the $\Delta\Delta Ct$ or the $\Delta Ct$ method. Quantitative reverse transcriptase polymerase chain reaction (qRT-PCR) data were normalized for the expression of ACTB, and $\Delta Ct$ values were calculated. Analysis was performed in technical and biological triplicates.

The list of genes which expression have been quantified by qRT-PCR is reported below.

TABLE 1

| Gene Symbol | UniGene # | Refseq Accession # | Band Size (bp) | Reference Position |
|---|---|---|---|---|
| LGR5 | Hs.658889 | NM_003667 | 91 | 1665 |
| EPHB2 | Hs.523329 | NM_004442 | 68 | 2908 |
| TERT | Hs.492203 | NM_198253 | 106 | 1072 |
| ACTB | Hs.520640 | NM_001101 | 174 | 730 |
| CasDase 8 | Hs.599762 | NM_001080124.1 | 124 | 648 |

Competitive ELISA Binding Assay

The following reagents were used to screen the newly generated anti-IGFBP3 antibodies: Recombinant Human IGFBP3 (0,223 mg/ml R&D System 8874-B3-025), Ecto-TMEM219 (0.5 mg/ml GenScript), newly generated anti-IGFBP3 mAbs (Yumab, under contract), goat polyclonal anti-IGFBP3 (LS-C149975 LSBio), mouse monoclonal anti-IGFBP3 (LS-C45037 LSBio), mouse 6× His tag HRP (GTX30506 Genetex), bovine serum albumin (BSA A9418 Sigma), Tween 20 (TW P2287 Sigma), ELISA colorimetric TMB reagent (HRP substrate, Item H Sigma, RABTMB3), ELISA STOP solution (Item I, Sigma, RABSTOP3), blocking reagent (3% BSA in PBS) and a diluent solution (0.5% BSA, 0.05% Tw in PBS).

Microplate was coated with 50 μl/well of 4 μg/ml rhIGFBP3 dissolved in PBS or PBS alone (no coating). Plate was incubated 90 minutes at 37° C. and washed with PBS (300 μl/well) and incubated with the blocking reagent (200 μl/well) 2 hours at room temperature. Samples were then diluted in the diluent solution (50 μl/well) and added to the plate as follows: diluent solution (none), ecto-TMEM 10 μg/ml, ecto-TMEM 10 μg/ml+anti-IGFBP3 mAbs 10 μg/ml, anti-IGFBP3 mAbs 10 μg/ml alone. After washing steps, plate was then incubated at room temperature for 1 hour with anti 6× His tag HRP diluted 1:2000 in Diluent solution (50 μl/well). ELISA plate was then read after adding visualization solution at ELISA reader and adsorbance was measured.

Epitope Binning

Epitope binning is a competitive immunoassay used to characterize and then sort a library of monoclonal antibodies against a target protein (Abdiche, Y. N.; D. S. Malashock; A. Pinkerton; J. Pons (March 2009). "Exploring blocking assays using Octet, ProteOn, and Biacore biosensors". Analytical Biochemistry. 386 (2): 172-180. doi: 10.1016/j.ab.2008.11.038. PMID 19111520). Antibodies against a similar target are tested against all other antibodies in the library in a pairwise fashion to see if antibodies block one another's binding to the epitope of an antigen. After each antibody has a profile created against all of the other antibodies in the library, a competitive blocking profile is created for each antibody relative to the others in the library. Closely related binning profiles indicate that the antibodies have the same or a closely related epitope and are "binned" together. Epitope binning is referenced in the literature under different names such as epitope mapping and epitope characterization (Brooks, B. D. (2014). "The Importance of Epitope Binning in Drug Discovery". Current Drug Discovery Technology. 11).

CVC microplates were coated with: i) 100 μl/well of 2 μg/ml rhIGFBP3 dissolved in PBS or PBS alone (no coating) and incubated 60 minutes at RT; ii) 100 μl/well of 2 μg/ml anti-IGFBP3 (LS-C45037 LSBio) and incubated o.n at 4° C. Plates were washed with $H_2O$-Tween20 (0.05%) and incubated with the blocking reagent (2% BSA-PBS-T (0.05%)). For condition ii) 100 μl/well of 2 μg/ml rhIGFBP3 was incubated o.n at 4° C. After washing the newly generated antibodies (in 2% BSA-PBS-T (0.05%)) were titrated onto the plate and incubated for 1 hour at RT. After washing steps, detection of bound antibodies was performed using a goat anti-human Fc-HRP antibody (Sigma A0170) in 2% BPS-PBS-T (0.05%) followed by washing and read out with TMB (100 μl/well). ELISA plates were then read measuring the absorbance at 450 nm.

Beta-Cells

Betalox-5 cells, a human beta cell line (36) were grown in culture flasks containing DMEM (glucose 1 g/L), BSA fraction V (0.02% wt/vol), Non-essential amino acids (1×) penicillin (100 units/mL), and streptomycin (100 μg/mL). The cells were cultured at 37° C. in a humidified incubator in 5% CO2. The cells were passaged once every second week. Beta cells were cultured with or without IGFBP3, with or without ecto-TMEM219, with or without newly generated monoclonal antibodies (see Recombinant proteins and interventional studies) and cells were collected for immunofluorescence studies, RNA extraction, apoptosis detection, and protein analysis. Supernatants were collected for assessment of insulin. Insulin levels were assayed with a microparticle enzyme immunoassay (Mercodia Iso-Insulin ELISA, 10-1113-01).

Statistical Analysis

Data are presented as mean and standard deviation (SD) and were tested for normal distribution with the Kolmogorov-Smirnov test and for homogeneity of variances with Levene's test. The statistical significance of differences was tested with two-tailed t-test and the chi-square ($\chi 2$) tests. Significance between the two groups was determined by two-tailed unpaired Student's t test. For multiple comparisons, the 1-way ANOVA test with Bonferroni correction was employed. Statistical analysis was conducted using GraphPad Prism version 5.0 (GraphPad Software, La Jolla, CA). All statistical tests were performed at the 5% significance level.

Example 1

Monoclonal Antibodies Development

Monoclonal anti-IGFBP3 antibodies were discovered from naïve human phage-display libraries using a recombinant full length human IGFBP3 (R&D cat n° 8874-B3) as antigen for the screening. Briefly, human IGFBP3 (R&D cat n° 8874-B3) was biotinylated and immobilized via streptavidin onto 96-well ELISA plates at 4° C. After washing and blocking of the wells with BSA, the antibody-phage libraries were added. Tested libraries were first cleared from antibody-phage that bind to Streptavidin (John deKruif and Ton Logtenberg, Phage Display of Antibodies, Encyclopedia of Immunology (Second Edition) 1998, Pages 1931-1934). Those phages that carried an antigen-specific antibody were captured on the plate surface. After removal by washing with PBS-T of unbound/weakly bound phage with, antigen-specific phage were eluted and amplified by phage infection in E. coli. This amplified library subset was again selected for target binding under more stringent conditions. In total, three selection rounds were performed to enrich antigen specific antibody-phage.

At the end of the discovery process, each selection output was screened for antigen-specific antibodies. For this purpose, 384 clones were chosen from each selection output and used for production of monoclonal scFv antibodies. These were then tested for specific antigen binding by ELISA. 24 target specific hits were identified which were sequenced. All antibodies showing unique CDRs sequences were cloned into a mammalian scFv-Fc expression vector. As a result, the scFv was genetically fused to a Fc Fragment of human IgG4.

This resulted in 11 scFv-Fc antibodies which were produced by transient transfection of HEK293 cells. Then, the antibodies were purified by affinity chromatography (Protein A) and re-buffered in PBS (no additives). The protein concentration was determined by UV/VIS spectrometry and purity was checked by Coomassie staining.

The sequences of the 11 novel anti-IGFBP3 antibodies are reported in the Tables below.

TABLE 2

VH CDR Sequences of exemplified antibodies

| Antibody | VH CDR1 | VH CDR2 | VH CDR3 |
|---|---|---|---|
| YU139-A02 | SYAIS (SEQ ID NO: 1) | GIIPIFGTANYAQKFQG (SEQ ID NO: 8) | DYYDSSGYYFDAFDI (SEQ ID NO: 17) |
| YU139-A03 | SYGIH (SEQ ID NO: 2) | IVSYDGRHKYYADSVKG (SEQ ID NO: 9) | DSGNSGLEGIHDY (SEQ ID NO: 18) |
| YU139-B01 | SSNWWS (SEQ ID NO: 3) | EVYHSGSTNYNPSLKS (SEQ ID NO: 10) | NIPLSSSWPNYYYYYGMDV (SEQ ID NO: 19) |
| YU139-C01 | SYGIS (SEQ ID NO: 4) | WINTYNGNTNYAQKLQG (SEQ ID NO: 11) | DIGYSGSYYSPYYYYGMDV (SEQ ID NO: 20) |
| YU139-C02 | SYGIS (SEQ ID NO: 4) | WISAYNGNTNYAQKLQG (SEQ ID NO: 12) | VPSEYYDFWSGYYTEENAFDI (SEQ ID NO: 21) |
| YU139-D02 | SYGMH (SEQ ID NO: 5) | VISYDGSNKYYADSVKG (SEQ ID NO: 13) | DNGDGYYYYYYMDV (SEQ ID NO: 22) |
| YU139-D03 | DYGIS (SEQ ID NO: 6) | WISGDNVKTTYAKKFQG (SEQ ID NO: 14) | GGIVFDY (SEQ ID NO: 23) |
| YU139-F02 | SYGIS (SEQ ID NO: 4) | WISAYNGNTNYAQKLQG (SEQ ID NO: 12) | GGIVFDY (SEQ ID NO: 23) |
| YU139-G01 | SYGIS (SEQ ID NO: 4) | WISAYNGNTYYAQKLQG (SEQ ID NO: 15) | LSYYNYAMDV (SEQ ID NO: 24) |
| YU139-G03 | TYVTS (SEQ ID NO: 7) | GIIPMFDTTEYAQKLEG (SEQ ID NO: 16) | AGGLSHFDY (SEQ ID NO: 25) |
| YU139-H03 | SYGIS (SEQ ID NO: 4) | WISAYNGNTNYAQKLQG (SEQ ID NO: 12) | VKWELGWAFDI (SEQ ID NO: 26) |

TABLE 3

VL CDR sequences of exemplified antibodies

| Antibody | VL CDR1 | VL CDR2 | VL CDR3 |
|---|---|---|---|
| YU139-A02 | SGSSSNIGTNTVS (SEQ ID NO: 27) | NNNERPS (SEQ ID NO: 37) | AAWDDNLTGLV (SEQ ID NO: 45) |
| YU139-A03 | RASQGISSWLA (SEQ ID NO: 28) | AASSLQS (SEQ ID NO: 38) | QQANSFPLT (SEQ ID NO: 46) |
| YU139-B01 | QGDSLRNYYAS (SEQ ID NO: 29) | GKNNRPS (SEQ ID NO: 39) | NSRDSSAKHWV (SEQ ID NO: 47) |
| YU139-C01 | QGDGLRNYFAS (SEQ ID NO: 30) | GKNNRPS (SEQ ID NO: 39) | NSRDGSGKHLV (SEQ ID NO: 48) |
| YU139-C02 | RASQSISSYLN (SEQ ID NO: 31) | AASSLQS (SEQ ID NO: 38) | QQSYSTWT (SEQ ID NO: 49) |
| YU139-D02 | RASQSISRWLA (SEQ ID NO: 32) | DASSLES (SEQ ID NO: 40) | QQSYSTPLT (SEQ ID NO: 50) |
| YU139-D03 | RASQSVSGNYLA (SEQ ID NO: 33) | GASSRAT (SEQ ID NO: 41) | QQYGSSPGT (SEQ ID NO: 51) |
| YU139-F02 | RASQSISSYLN (SEQ ID NO: 31) | AASSLQS (SEQ ID NO: 38) | QQSYSTPLT (SEQ ID NO: 50) |
| YU139-G01 | TGTSSDVGGYNHVS (SEQ ID NO: 34) | EVSNRPS (SEQ ID NO: 42) | SSYTSSNTWV (SEQ ID NO: 52) |
| YU139-G03 | RSSQSLLHSNGNNYLN (SEQ ID NO: 35) | LSSRRAS (SEQ ID NO: 43) | MQGLQTPWT (SEQ ID NO: 53) |
| YU139-H03 | TGSSSNIGAGYDVH (SEQ ID NO: 36) | GNSNRPS (SEQ ID NO: 44) | QSYDSSLSTV (SEQ ID NO: 54) |

TABLE 4

VH amino acid sequences of exemplified antibodies

| Antibody | AA of VH |
|---|---|
| YU139-A02 | QVQLVQSGAEVKKPGSSVKVSCKASGGTFSSYAISWVRQAPGQGLEWMGGIIPIFGTANYAQK FQGRVTITADESTSTAYMELSSLRSEDTAVYYCARDYYDSSGYYFDAFDIWGQGTMVTVSS (SEQ ID NO: 55) |
| YU139-A03 | QVQLVQSGGGVVQPGRSLRLSCAASGFTFSSYGIHWVRQAPGKGLEWVAIVSYDGRHKYYAD SVKGRFTISRDDSKNTIYLQMDSLRAEDTAVYYCAKDSGNSGLEGIHDYWGQGTLVTVSS (SEQ ID NO: 56) |
| YU139-B01 | QVQLQESGPGLVKPSGTLSLTCAVSGGSISSSNWWSWVRQPPGKGLEWIGEVYHSGSTNYNP SLKSRVTISVDKSKNQFSLKLSSVTAADTAVYYCARNIPLSSSWPNYYYYYGMDVWGQGTTVTV SS (SEQ ID NO: 57) |
| YU139-C01 | QVQLVQSGAEVKKPGASVKVSCKASGYTFTSYGISWVRQAPGQGLEWMGWINTYNGNTNYA QKLQGRVTMTTDTSTTTAYMELRSLRSDDTAVYYCARDIGYSGSYYSPYYYYGMDVWGQGTTV TVSS (SEQ ID NO: 58) |
| YU139-C02 | EVQLVQSGAEVKKPGASVKVSCKASGYTFTSYGISWVRQAPGQGLEWMGWISAYNGNTNYA QKLQGRVTMTTDTSTSTAYMELRSLRSDDTAVYYCARVPSEYYDFWSGYYTEENAFDIWGQGT MVTVSS (SEQ ID NO: 59) |
| YU139-D02 | EVQLVESGGGVVQPGRSLRLSCAASGFTFSSYGMHWVRQAPGKGLEWVAVISYDGSNKYYAD SVKGRFTISRDNSKNTLYLQMNSLRAEDTAVYYCAKDNGDYGYYYYYYMDVWGKGTTVTVSS (SEQ ID NO: 60) |
| YU139-D03 | QVQLVQSGAEVKKPGASVKVSCKASGYTFSDYGISWVRQAPGQGLEWMGWISGDNVKTTYA KKFQGRVTLTTDTSTSTAYMELRSLTSDDTAAYYCARGGIVFDYWGQGTLVTVSS (SEQ ID NO: 61) |
| YU139-F02 | QVQLVQSGAEVKKPGASVKVSCKASGYTFTSYGISWVRQATGQGLEWMGWISAYNGNTNYA QKLQGRVTMTTDTSTSTAYMELRSLRSDDTAVYYCARGGIVFDYWGQGTLVTVSS (SEQ ID NO: 62) |
| YU139-G01 | QMQLVQSGAEVKMPGASVKVSCKASGYTFTSYGISWVRQAPGQGLEWMGWISAYNGNTYY AQKLQGRVTMTADTSTSTAYMDLRSLRSDDTAVYYCARLSYYNYAMDVWGQGTTVTVSS (SEQ ID NO: 63) |
| YU139-G03 | QVQLQQSGAEVKKPGSSVKVSCKASGGIFSTYVTSWVRQAPGQGLEWMGGIIPMFDTTEYAQ KLEGRVTITVDESTNTAYMELSSLRFEDTAVYYCARAGGLSHFDYWGQGTLVTVSS (SEQ ID NO: 64) |
| YU139-H03 | QVQLVQSGAEVKKPGASVKVSCKASGYTFTSYGISWVRQAPGQGLEWMGWISAYNGNTNYA QKLQGRVTMTTDTSTSTAYMELRSLRSDDTAVYYCARVKWELGWAFDIWGQGTMVTVSS (SEQ ID NO: 65) |

TABLE 5

VL amino acid sequences of exemplified antibodies

| Antibody | AA of VL |
|---|---|
| YU139-A02 | QAGLTQPPSASGTPGQRVIISCSGSSSNIGTNTVSWYQHLPGTAPKLLIYNNNERPSGVPRRFS GSRSGASASLAISGLQSDDEAHYYCAAWDDNLTGLVFGGGTKLTVL (SEQ ID NO: 66) |
| YU139-A03 | DVVMTQSPSSVSASVGDRVTITCRASQGISSWLAWYQQKPGKAPKLLIYAASSLQSGVPSRFS GSGSGTDFTLTISSLQPEDFGTYYCQQANSFPLTFGGGTKVEIK (SEQ ID NO: 67) |
| YU139-B01 | SSELTQDPAVSVALGQTVRITCQGDSLRNYYASWYQQKPGQAPVLVIYGKNNRPSGIPDRFSG SSSGNTASLTINGAQAEDEADYYCNSRDSSAKHWVFGGGTKLTV (SEQ ID NO: 68) |
| YU139-C01 | SSELTQDPAVSVALGQTVRITCQGDGLRNYFASWYQQKPGQAPVLVIYGKNNRPSGIPDRFSG SSSGNTASLRIAGAQAEDEADYYCNSRDGSGKHLVFGGGTKLTV (SEQ ID NO: 69) |
| YU139-C02 | DIVMTQSPSSLSASVGDRVTITCRASQSISSYLNWYQQKPGKAPKLLIYAASSLQSGVPSRFSGS GSGTDFTLTISSLQPEDFATYYCQQSYSTWTFGQGTKVEIK (SEQ ID NO: 70) |
| YU139-D02 | DIQMTQSPSTLSASVGDRVTITCRASQSISRWLAWYQQKPGKAPKLLIYDASSLESGVPSRFSG SGSGTEFTLTISSLQPDDFATYYCQQSYSTPLTFGPGTKVDIK (SEQ ID NO: 71) |

TABLE 5-continued

VL amino acid sequences of exemplified antibodies

| Antibody | AA of VL |
|---|---|
| YU139-D03 | ETTLTQSPGTLSLSPGERATLSCRASQSVSGNYLAWYQQKPGQPPRLLIFGASSRATGIPDRFSG<br>SGSGTDFTLTISRLEPEDFGVYYCQQYGSSPGTFGQGTKVEIK (SEQ ID NO: 72) |
| YU139-F02 | DVVMTQSPSSLSASVGDRVTITCRASQSISSYLNWYQQKPGKAPKLLIYAASSLQSGVPSRFSGS<br>GSGTDFTLTISSLQPEDFATYYCQQSYSTPLTFGGGTKVEIK (SEQ ID NO: 73) |
| YU139-G01 | QSALTQPPSASGSPGQSVTISCTGTSSDVGGYNHVSWYQQHPGKAPKLMIYEVSNRPSGVPN<br>RFSGSKSGNTASLTISGLQAEDEADYYCSSYTSSNTWVFGGGTKLTVL (SEQ ID NO: 74) |
| YU139-G03 | EIVLTQSPLSLPVTPGEPASISCRSSQSLLHSNGNNYLNWYLQKPGQSPQLLIYLSSRRASGVPDR<br>FSGSGSGTDFTLKISRVEAEDVGVYYCMQGLQTPWTFGQGTKVETK (SEQ ID NO: 75) |
| YU139-H03 | QAVLTQPPSVSGAPGQRVTISCTGSSSNIGAGYDVHWYQQLPGTAPKLLIYGNSNRPSGVPDR<br>FSGSKSGTSAPLAITGLQAEDEADYYCQSYDSSLSTVFGGGTKLTVL (SEQ ID NO: 76) |

TABLE 6

VH nucleotide sequences of exemplified antibodies

| Antibody | DNA of VH |
|---|---|
| YU139-A02 | CAGGTTCAGCTGGTGCAGTCTGGGGCTGAGGTGAAGAAGCCTGGGTCCTCGGTGAAGGT<br>CTCCTGCAAGGCTTCTGGAGGCACCTTCAGCAGCTATGCTATCAGCTGGGTGCGACAGGC<br>CCCTGGACAAGGGCTTGAGTGGATGGGAGGGATCATCCCTATCTTTGGTACAGCAAACTA<br>CGCACAGAAGTTCCAGGGCAGAGTCACGATTACCGCGGACGAATCCACGAGCACAGCCTA<br>CATGGAGCTGAGCAGCCTGAGATCTGAGGACACGGCCGTGTATTACTGTGCGAGAGATTA<br>CTATGATAGTAGTGGTTATTACTTTGATGCTTTTGATATCTGGGGCCAAGGGACAATGGTC<br>ACCGTCTCTTCA (SEQ ID NO: 77) |
| YU139-A03 | CAGGTCCAGCTGGTACAATCTGGGGGAGGCGTGGTCCAGCCTGGGAGGTCCCTGAGACT<br>CTCCTGTGCAGCCTCTGGATTCACCTTCAGTAGCTATGGCATCCACTGGGTCCGCCAGGCT<br>CCAGGCAAGGGGCTGGAGTGGGTGGCAATTGTATCATATGATGGAAGACATAAATATTAT<br>GCAGACTCCGTGAAGGGCCGATTCACCATCTCCAGAGACGATTCCAAGAACACGATCTAT<br>CTGCAAATGGACAGCCTGAGAGCTGAGGACACGGCTGTATATTACTGTGCGAAAGATAGT<br>GGGAACTCCGGTCTGGAAGGTATCCATGACTACTGGGGCCAGGGAACCCTGGTCACCGTC<br>TCCTCA (SEQ ID NO: 78) |
| YU139-B01 | CAGGTGCAGCTGCAGGAGTCGGGCCCAGGACTGGTGAAGCCTTCGGGGACCCTGTCCCTC<br>ACCTGCGCTGTCTCTGGTGGCTCCATCAGCAGTAGTAACTGGTGGAGTTGGGTCCGCCAG<br>CCCCCAGGGAAGGGGCTGGAGTGGATTGGGGAAGTCTATCATAGTGGGAGCACCAACTA<br>CAACCCGTCCCTCAAGAGTCGAGTCACCATATCAGTAGACAAGTCAAGAACCAGTTCTCC<br>CTGAAGCTGAGCTCTGTGACCGCCGCGGACACGGCCGTGTATTACTGTGCGAGAAACATC<br>CCCCTTAGCAGCAGCTGGCCTAATTACTACTACTACTACGGTATGGACGTCTGGGGCCAAG<br>GGACCACGGTCACCGTCTCCTCA (SEQ ID NO: 79) |
| YU139-C01 | CAGGTCCAGCTGGTGCAATCTGGAGCTGAGGTGAAGAAGCCTGGGGCCTCAGTGAAGGT<br>CTCCTGCAAGGCTTCTGGCTACACCTTTACCAGCTATGGTATCAGCTGGGTGCGACAGGCC<br>CCTGGACAAGGGCTTGAGTGGATGGGATGGATCAACACTTACAATGGTAACACAAACTAT<br>GCACAGAAACTCCAGGGCAGAGTCACCATGACCACAGACACATCCACGACCACAGCCTAC<br>ATGGAGCTGAGGAGCCTGAGATCTGACGACACGGCCGTATATTACTGTGCGAGAGATATC<br>GGGTATAGTGGGAGCTACTATTCGCCCTACTACTACTACGGTATGGACGTCTGGGGCCAA<br>GGGACCACGGTCACCGTCTCCTCA (SEQ ID NO: 80) |
| YU139-C02 | GAGGTGCAGCTGGTGCAGTCTGGGGCTGAGGTGAAGAAGCCTGGGGCTTCAGTGAAGGT<br>CTCCTGCAAGGCTTCTGGTTACACCTTTACCAGCTATGGTATCAGCTGGGTGCGACAGGCC<br>CCTGGACAAGGGCTTGAGTGGATGGGATGGATCAGCGCTTACAATGGTAACACAAACTAT<br>GCACAGAAGCTCCAGGGCAGAGTCACCATGACCACAGACACATCCACGAGCACAGCCTAC<br>ATGGAGCTGAGGAGCCTGAGATCTGACGACACGGCCGTGTATTACTGTGCGAGAGTTCCC<br>TCAGAGTATTACGATTTTTGGAGTGGTTATTATACCGAAGAGAATGCTTTTGATATCTGGG<br>GCCAAGGGACAATGGTCACCGTCTCTTCA (SEQ ID NO: 81) |
| YU139-D02 | GAGGTGCAGCTGGTGGAGTCTGGGGGAGGCGTGGTCCAGCCTGGGAGGTCCCTGAGACT<br>CTCCTGTGCAGCCTCTGGATTCACCTTCAGTAGCTATGGCATGCACTGGGTCCGCCAGGCT<br>CCAGGCAAGGGGCTGGAGTGGGTGGCAGTTATATCATATGATGGAAGTAATAAATACTAT<br>GCAGACTCCGTGAAGGGCCGATTCACCATCTCCAGAGACAATTCCAAGAACACGCTGTAT<br>CTGCAAATGAACAGCCTGAGAGCTGAGGACACGGCTGTGTATTACTGTGCGAAAGATAAC<br>GGTGACTACGGATACTACTACTACTACATGGACGTCTGGGGCAAAGGGACCACGGTC<br>ACCGTCTCCTCA (SEQ ID NO: 82) |
| YU139-D03 | CAGGTGCAGCTGGTGCAGTCTGGAGCTGAGGTGAAGAAGCCTGGGGCCTCAGTGAAGGT<br>CTCCTGCAAGGCTTCTGGTTACACCTTTTCCGACTATGGTATCAGCTGGGTGCGACAGGCC<br>CCTGGACAAGGGCTTGAGTGGATGGGATGGATCAGCGGTGACAATGTTAAGACTACCTAT<br>GCAAAGAAGTTCCAGGGCAGAGTCACCCTGACCACAGACACATCCACGAGCACAGCCTAC |

TABLE 6-continued

VH nucleotide sequences of exemplified antibodies

| Antibody | DNA of VH |
|---|---|
| | ATGGAGCTGAGGAGCCTGACATCTGACGACACGGCCGCATATTACTGTGCGAGAGGGG<br>GATCGTATTTGACTACTGGGGCCAGGGAACCCTGGTCACCGTCTCCTCA (SEQ ID NO: 83) |
| YU139-<br>F02 | CAGGTTCAGCTGGTGCAGTCTGGGGCTGAGGTGAAGAAGCCTGGGGCCTCAGTGAAGGT<br>CTCCTGCAAGGCTTCTGGTTACACCTTTACCAGCTATGGTATCAGCTGGGTGCGACAGGCC<br>ACTGGACAAGGGCTTGAGTGGATGGGATGGATCAGCGCTTACAATGGTAACACAAACTAT<br>GCACAGAAGCTCCAGGGCAGAGTCACCATGACCACAGACACATCCACGAGCACAGCCTAC<br>ATGGAGCTGAGGAGCCTGAGATCTGACGACACGGCCGTGTATTACTGTGCGAGAGGGG<br>GATCGTATTTGACTACTGGGGCCAGGGAACCCTGGTCACCGTCTCCTCA (SEQ ID NO: 84) |
| YU139-<br>G01 | CAAATGCAGCTGGTACAGTCTGGGGCTGAGGTGAAGATGCCTGGGGCCTCAGTGAAGGT<br>CTCCTGCAAGGCTTCTGGTTACACCTTTACCAGCTATGGTATCAGCTGGGTGCGACAGGCC<br>CCTGGACAAGGGCTTGAGTGGATGGGGTGGATCAGCGCTTACAATGGTAACACATACTAT<br>GCACAGAAACTCCAGGGCAGAGTCACCATGACCGCAGACACATCCACGAGCACAGCCTAC<br>ATGGACCTGAGGAGCCTGAGATCTGACGACACGGCCGTGTATTACTGTGCGAGACTATCA<br>TATTACAACTACGCTATGGACGTCTGGGGCCAAGGGACCACGGTCACCGTCTCCTCA (SEQ<br>ID NO: 85) |
| YU139-<br>G03 | CAGGTACAGCTGCAGCAGTCAGGGGCTGAGGTGAAGAAGCCTGGGTCCTCGGTGAAGGT<br>GTCCTGCAAGGCTTCTGGAGGCATCTTCAGCACCTATGTGACCAGCTGGGTGCGACAGGC<br>CCCTGGACAAGGGCTTGAGTGGATGGGAGGGATCATCCCTATGTTTGACACAACAGAGTA<br>CGCACAGAAGCTCGAGGGCAGAGTCACGATCACCGTGGACGAATCCACGAACACAGCCT<br>ACATGGAGCTGAGCAGCCTGAGATTTGAGGACACGGCCGTATATTACTGTGCGAGAGCG<br>GGAGGTTTGAGCCACTTTGACTACTGGGGCCAGGGAACTCTGGTCACCGTCTCGTCA<br>(SEQ ID NO: 86) |
| YU139-<br>H03 | CAGGTCCAGCTGGTACAGTCTGGAGCTGAGGTGAAGAAGCCTGGGGCCTCAGTGAAGGT<br>CTCCTGCAAGGCTTCTGGTTACACCTTTACCAGCTATGGTATCAGCTGGGTGCGACAGGCC<br>CCTGGACAAGGGCTTGAGTGGATGGGATGGATCAGCGCTTACAATGGTAACACAAACTAT<br>GCACAGAAGCTCCAGGGCAGAGTCACCATGACCACAGACACATCCACAAGCACAGCCTAC<br>ATGGAGCTGAGGAGCCTGAGATCTGACGACACGGCCGTGTATTACTGTGCGAGAGTGAA<br>GTGGGAGCTAGGGTGGCTTTTGATATCTGGGGCCAAGGGACAATGGTCACCGTCTCTTC<br>A (SEQ ID NO: 87) |

TABLE 7

VL nucleotide sequences

| Antibody | DNA of VL |
|---|---|
| YU139-<br>A02 | CAGGCTGGGCTGACTCAGCCACCCTCAGCGTCTGGGACCCCCGGGCAGAGGGTCATCATC<br>TCTTGTTCTGGAAGCAGCTCCAACATCGGAACTAATACTGTAAGCTGGTATCAACACCTCC<br>CAGGAACGGCCCCCAAGCTCCTCATCTATAACAATAATGAACGGCCCTCAGGGGTCCCTCG<br>CCGATTCTCTGGCTCCAGGTCTGGCGCCTCAGCCTCCCTGGCCATCAGTGGGCTCCAGTCT<br>GACGATGAGGCTCATTATTATTGTGCAGCCTGGGATGACAACCTGACTGGCTTGGTGTTCG<br>GCGGAGGGACCAAACTGACCGTCCTA (SEQ ID NO: 88) |
| YU139-<br>A03 | GATGTTGTGATGACTCAGTCTCCTTCTTCCGTGTCTGCATCTGTAGGAGACAGAGTCACCA<br>TCACTTGTCGGGCGAGTCAGGGTATTAGCAGCTGGTTAGCCTGGTATCAGCAGAAACCAG<br>GGAAAGCCCCTAAGCTCCTGATCTATGCTGCATCCAGTTTGCAAAGTGGGGTCCCATCAAG<br>GTTCAGCGGCAGTGGATCTGGGACAGATTTCACACTCACCATCAGCAGCCTGCAGCCTGA<br>AGATTTTGGAACTTACTATTGTCAACAGGCTAACAGTTTTCCGCTCACTTTCGGCGGAGGG<br>ACCAAGGTGGAGATCAAA (SEQ ID NO: 89) |
| YU139-<br>B01 | TCTTCTGAGCTGACTCAGGACCCTGCTGTGTCTGTGGCCTTGGGACAGACAGTCAGGATCA<br>CATGCCAAGGAGACAGCCTCAGAAACTATTATGCAAGCTGGTACCAGCAGAAGCCAGGAC<br>AGGCCCCTGTACTTGTCATCTATGGTAAAAACAACCGGCCCTCAGGGATCCCAGACCGATT<br>CTCTGGCTCCAGCTCAGGAAACACAGCTTCCTTGACCATCAATGGGGCTCAGGCGGAAGA<br>TGAGGCTGACTATTACTGTAACTCCCGGGACAGCAGTGCTAAACATTGGGTGTTCGGCGG<br>AGGGACCAAGCTGACCGTC (SEQ ID NO: 90) |
| YU139-<br>C01 | TCTTCTGAGCTGACTCAGGACCCTGCTGTGTCTGTGGCCTTGGGACAGACAGTCAGGATCA<br>CGTGCCAAGGAGACGGCCTCAGAAACTATTTTGCAAGTTGGTACCAGCAGAAGCCAGGAC<br>AGGCCCCTGTACTTGTCATCTATGGTAAAAACAACCGGCCCTCAGGGATCCCAGACCGATT<br>CTCTGGCTCCAGCTCAGGAAACACAGCTTCCTTGAGAATCGCTGGGGCTCAGGCGGAAGA<br>TGAGGCTGACTATTACTGTAATTCCCGGGACGGCAGTGGTAAGCATCTGGTATTCGGCGG<br>AGGGACCAAGTTGACCGTC (SEQ ID NO: 91) |

TABLE 7-continued

VL nucleotide sequences

| Antibody | DNA of VL |
|---|---|
| YU139-C02 | GACATCGTGATGACCCAGTCTCCATCCTCCCTGTCTGCATCTGTAGGAGACAGAGTCACCA<br>TCACTTGCCGGGCAAGTCAGAGCATTAGCAGCTATTTAAATTGGTATCAGCAGAAACCAG<br>GGAAAGCCCCTAAGCTCCTGATCTATGCTGCATCCAGTTTGCAAAGTGGGGTCCCATCAAG<br>GTTCAGTGGCAGTGGATCTGGGACAGATTTCACTCTCACCATCAGCAGTCTGCAACCTGAA<br>GATTTTGCAACTTACTACTGTCAACAGAGTTACAGTACCTGGACGTTCGGCCAAGGGACCA<br>AGGTGGAAATCAAA (SEQ ID NO: 92) |
| YU139-D02 | GACATCCAGATGACTCAGTCTCCTTCCACCCTGTCTGCATCTGTAGGAGACAGAGTCACCA<br>TCACTTGCCGGGCCAGTCAGAGTATTAGTAGGTGGTTGGCCTGGTATCAGCAGAAACCAG<br>GGAAAGCCCCTAAGCTCCTGATCTATGATGCCTCCAGTTTGGAAAGTGGGGTCCCATCAA<br>GGTTCAGCGGCAGTGGATCTGGGACAGAATTCACTCTCACCATCAGCAGCCTGCAGCCTG<br>ATGATTTTGCAACTTATTACTGTCAACAGAGTTACAGTACCCCTCTTACTTTCGGCCCTGGG<br>ACCAAAGTGGATATCAAA (SEQ ID NO: 93) |
| YU139-D03 | GAAACGACACTCACGCAGTCTCCAGGCACCCTGTCTTTGTCTCCAGGGGAAAGAGCCACC<br>CTCTCCTGCAGGGCCAGTCAGAGTGTTAGTGGCAACTACTTAGCCTGGTACCAGCAGAAA<br>CCTGGCCAGCCTCCCAGGCTCCTCATCTTTGGTGCATCCAGCAGGGCCACTGGCATCCCAG<br>ACAGGTTCAGTGGCAGTGGGTCTGGGACAGACTTCACTCTCACCATCAGCAGACTGGAGC<br>CTGAAGATTTTGGAGTGTATTACTGTCAGCAGTATGGTAGCTCACCAGGGACGTTCGGCC<br>AAGGGACCAAGGTGGAAATCAAA (SEQ ID NO: 94) |
| YU139-F02 | GATGTTGTGATGACTCAGTCTCCATCCTCCCTGTCTGCATCTGTAGGAGACAGAGTCACCA<br>TCACTTGCCGGGCAAGTCAGAGCATTAGCAGCTATTTAAATTGGTATCAGCAGAAACCAG<br>GGAAAGCCCCTAAGCTCCTGATCTATGCTGCATCCAGTTTGCAAAGTGGGGTCCCATCAAG<br>GTTCAGTGGCAGTGGATCTGGGACAGATTTCACTCTCACCATCAGCAGTCTGCAACCTGAA<br>GATTTTGCAACTTACTACTGTCAACAGAGTTACAGTACCCCGCTCACTTTCGGCGGAGGGA<br>CCAAGGTGGAGATCAAA (SEQ ID NO: 95) |
| YU139-G01 | CAGTCTGCCCTGACTCAGCCTCCCTCCGCGTCCGGGTCCCCTGGACAGTCAGTCACCATCTC<br>CTGCACTGGAACCAGCAGTGATGTTGGTGGTTATAACCATGTCTCCTGGTACCAGCAACAC<br>CCAGGCAAAGCCCCCAAACTCATGATTTATGAGGTCAGTAATCGGCCCTCAGGAGTTCCTA<br>ATCGCTTCTCTGGCTCCAAGTCTGGCAACACGGCCTCCCTGACCATCTCTGGGCTCCAGGC<br>TGAGGACGAGGCTGATTATTACTGCAGCTCATATACAAGCAGCAACACTTGGGTGTTCGG<br>CGGAGGGACCAAGCTGACCGTCCTA (SEQ ID NO: 96) |
| YU139-G03 | GAAATTGTGCTGACTCAGTCTCCACTCTCCCTGCCCGTCACCCCTGGAGAGCCGGCCTCCA<br>TCTCCTGCAGGGTCTAGTCAGAGCCTCCTGCATAGTAATGGAAACAACTATTTGAATTGGTA<br>CCTGCAGAAGCCAGGGCAGTCTCCACAGCTCCTGATCTATTTGAGTTCTCGTCGGGCCTCC<br>GGGGTCCCTGACAGGTTCAGTGGCAGTGGATCAGGCACAGATTTTACACTGAAAATTAGC<br>AGAGTGGAGGCTGAGGATGTTGGGGTTTATTACTGCATGCAAGGTCTACAAACTCCGTGG<br>ACGTTCGGCCAAGGGACCAAGGTGGAAACCAAA (SEQ ID NO: 97) |
| YU139-H03 | CAGGCAGTGCTGACTCAGCCACCCTCAGTGTCTGGGGCCCCAGGGCAGAGGGTCACCATC<br>TCCTGCACTGGGAGCAGCTCCAACATCGGGGCAGGTTATGATGTACACTGGTACCAGCAG<br>CTTCCAGGAACAGCCCCCAAACTCCTCATCTATGGTAACAGCAATCGGCCCTCAGGGGTCC<br>CTGACCGATTCTCTGGCTCCAAGTCTGGCACCTCAGCCCCCTGGCCATCACTGGGCTCCA<br>GGCTGAGGACGAGGCTGATTATTACTGCCAGTCTTATGACAGCAGCCTGAGTACGGTATT<br>CGGCGGAGGGACCAAGCTGACCGTCCTA (SEQ ID NO: 98) |

TABLE 8

Constant region amino acid sequences

| Constant region | AA |
|---|---|
| Human IgG4 heavy chain P01861.1 | ASTKGPSVFPLAPCSRSTSESTAALGCLVKDYFPEPVTVSWNSGALTSGVHTF<br>PAVLQSSGLYSLSSVVTVPSSSLGTKTYTCNVDHKPSNTKVDKRVESKYGPPC<br>PSCPAPEFLGGPSVFLFPPKPKDTLMISRTPEVTCVVVDVSQEDPEVQFNWY<br>VDGVEVHNAKTKPREEQFNSTYRVVSVLTVLHQDWLNGKEYKCKVSNKGL<br>PSSIEKTISKAKGQPREPQVYTLPPSQEEMTKNQVSLTCLVKGFYPSDIAVEW<br>ESNGQPENNYKTTPPVLDSDGSFFLYSRLTVDKSRWQEGNVFSCSVMHEAL<br>HNHYTQKSLSLSLGK (SEQ ID NO: 99) |
| Human IgG2 heavy chain P01859 | ASTKGPSVFPLAPCSRSTSESTAALGCLVKDYFPEPVTVSWNSGALTSGVHTF<br>PAVLQSSGLYSLSSVVTVPSSNFGTQTYTCNVDHKPSNTKVDKTVERKCCVE<br>CPPCPAPPVAGPSVFLFPPKPKDTLMISRTPEVTCVVVDVSHEDPEVQFNW<br>YVDGVEVHNAKTKPREEQFNSTFRVVSVLTVVHQDWLNGKEYKCKVSNKG<br>LPAPIEKTISKTKGQPREPQVYTLPPSREEMTKNQVSLTCLVKGFYPSDISVE<br>WESNGQPENNYKTTPPMLDSDGSFFLYSKLTVDKSRWQQGNVFSCSVMH<br>EALHNHYTQKSLSLSPGK (SEQ ID NO: 100) |

TABLE 8-continued

Constant region amino acid sequences

| Constant region | AA |
| --- | --- |
| Human light chain, lambda 1 P0CG04 | GQPKANPTVTLFPPSSEELQANKATLVCLISDFYPGAVTVAWKADGSPVKA GVETTKPSKQSNNKYAASSYLSLTPEQWKSHRSYSCQVTHEGSTVEKTVAPT ECS (SEQ ID NO: 101) |
| Human light chain, lambda 2 P0DOY2 | GQPKAAPSVTLFPPSSEELQANKATLVCLISDFYPGAVTVAWKADSSPVKAG VETTTPSKQSNNKYAASSYLSLTPEQWKSHRSYSCQVTHEGSTVEKTVAPTE CS (SEQ ID NO: 102) |
| Human light chain, kappa P01834 | RTVAAPSVFIFPPSDEQLKSGTASVVCLLNNFYPREAKVQWKVDNALQSGN SQESVTEQDSKDSTYSLSSTLTLSKADYEKHKVYACEVTHQGLSSPVTKSFNR GEC (SEQ ID NO: 103) |

Example 2

A Commercially Available Anti-IGFBP3 Monoclonal Antibody does not Affect IGFBP3/TMEM219 Binding A commercially available anti-IGFBP3 antibody was tested for its ability to displace the binding of ecto-TMEM219 to IGFBP3. Displacement of binding would indicate both (i) the ability of the antibody to inhibit binding of IGFBP3 to the native TMEM219 receptor, and (ii) the ability of the antibody to mimic the neutralizing activities of the ecto-TMEM219 ligand trap fusion protein.

As shown in FIG. 1A, we coated the plate with the commercial anti-IGFBP3 monoclonal antibody and added a pre-formed complex of IGFBP3 and Ecto-TMEM219, formed by pre-incubating IGFBP3 and Ecto-TMEM219 for 30 minutes. We then assessed the signal of Ecto-TMEM219 by using an anti-His tag and an anti-His-tag Streptavidin-HRP to detect whether Ecto-TMEM219 was still bound to the complex (high signal) or was displaced and washed away (low signal). Results are shown in FIG. 1B.

As shown in FIG. 1B, the commercial anti-IGFBP3 mAb is able to bind the IGFBP3-Ecto-TMEM219 complex, thus suggesting that it did not displace the IGFBP3-Ecto-TMEM219 binding. A monoclonal anti-IGFBP3 antibody (LSBio) was evaluated in a competitive ELISA binding assay (FIG. 1B).

Commercially Available Anti-IGFBP3 Antibodies do not Rescue IGFBP3-Mediated Damage of Mini-Guts in Different Disease Models.

Figure 2:
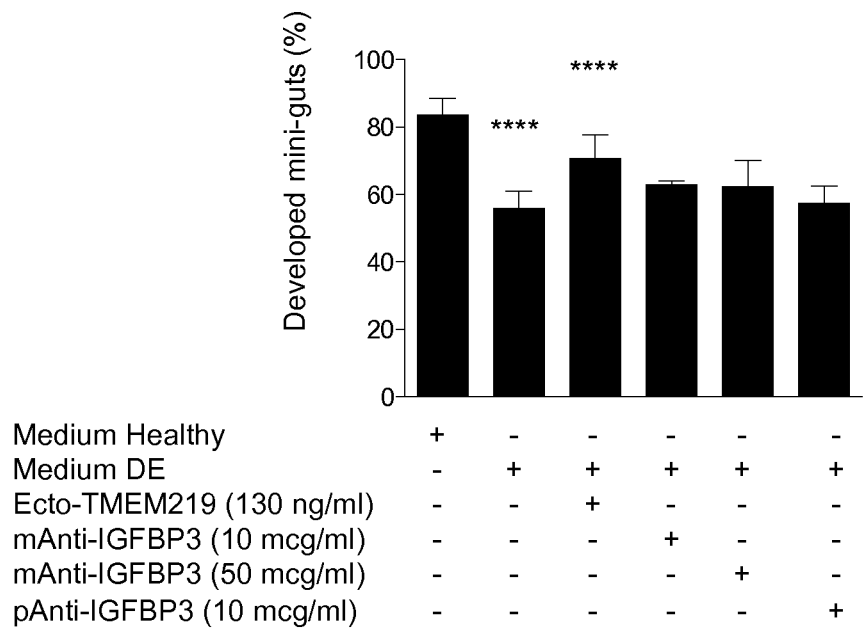
FIG. 2. Effect of commercially available anti-IGFBP3 antibodies, LSBIO LS-C149975/72664 clone 83.8F9) in rescuing mini-guts development in a model of diabetic enteropathy (DE, n=3). Monoclonal antibody was tested at a 1:10 and 1:50 ratio compared to ecto-TMEM219, while polyclonal antibody was tested at a 1:10 ratio, only. ****$p<0.0001$ Medium DE vs. Medium Healthy, Ecto-TMEM219 vs. Medium DE.

In order to assess whether commercially available antibodies, both monoclonal and polyclonal, could mimic the ability of the ecto-TMEM219 ligand trap to rescue mini-gut growth in intestinal stem cell (ISC) injury disease conditions though preventing the binding of IGFBP3 to TMEM219, they were further tested in vitro in the mini-gut assay. Mini-guts were generated from healthy controls as already described (4, 18). As shown in the left-most 3 bars in FIG. 2, incubation in the presence of medium from patients with diabetic enteropathy ("Medium DE") significantly reduced formation of mini-guts as compared to incubation in medium from healthy individuations ("Medium Health"); further addition of Ecto-TMEM219 at 130 ng/ml restored mini-gut growth in the presence of Medium DE.

Monoclonal and polyclonal antibodies were tested at three different concentrations in the presence of medium from individuals with diabetic enteropathy ("Medium DE"). Neither commercially available monoclonal nor polyclonal anti-IGFBP3 antibodies significantly improved the development of mini-guts in the presence of medium from individuals with diabetic enteropathy. None of the tested antibodies mimicked the ability of ecto-TMEM219 to rescue mini-gut development, suggesting that commercial anti-IGFBP3 antibodies would not be able to prevent ISC damage in disease conditions such as diabetic enteropathy; consistent with the data from Example 1, we infer that this lack of functional activity can be attributed to their inability to prevent binding of IGFBP3 to TMEM219 binding.

This highlights the need for other anti-IGFBP3 antibodies that selectively prevent the IGFBP3-TMEM219 interaction.

Antibodies were also tested in mini-gut assays using crypts obtained from patients with established Crohn's disease (an inflammatory bowel disease, IBD) undergoing surgery for disease complications (strictures, fistulae). This model is highly clinically relevant as it recapitulates in vitro the major features of the disease condition in patients.

Figure 3:
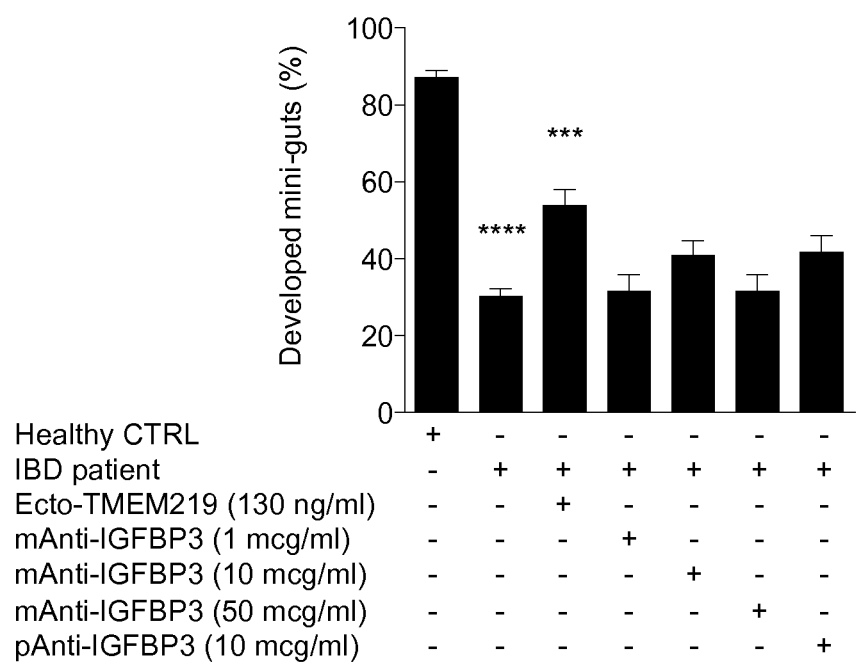
FIG. 3. Effect of commercially available anti-IGFBP3 antibodies (LSBIO LS-C45037/clone 83.8F9) in rescuing mini-guts development in the model of Crohn's disease (IBD, n=3). Monoclonal antibody was tested at a 1:1, 1:10 and 1:50 ratio compared to ecto-TMEM219, while polyclonal antibody was tested at a 1:10 ratio, only. **$p<0.0001$ IBD patient vs. Healthy CTRL; *$p<0.001$ Ecto-TMEM219 vs. IBD patient.

As shown in FIG. 3, we observed that mini-guts of IBD patients failed to fully grow and develop, and that ecto-TMEM219 was able to rescue mini-guts growth and re-establish organoids development. By contrast, commercially available antibodies tested at different molecular ratio did not exert any effect.

Figure 4:
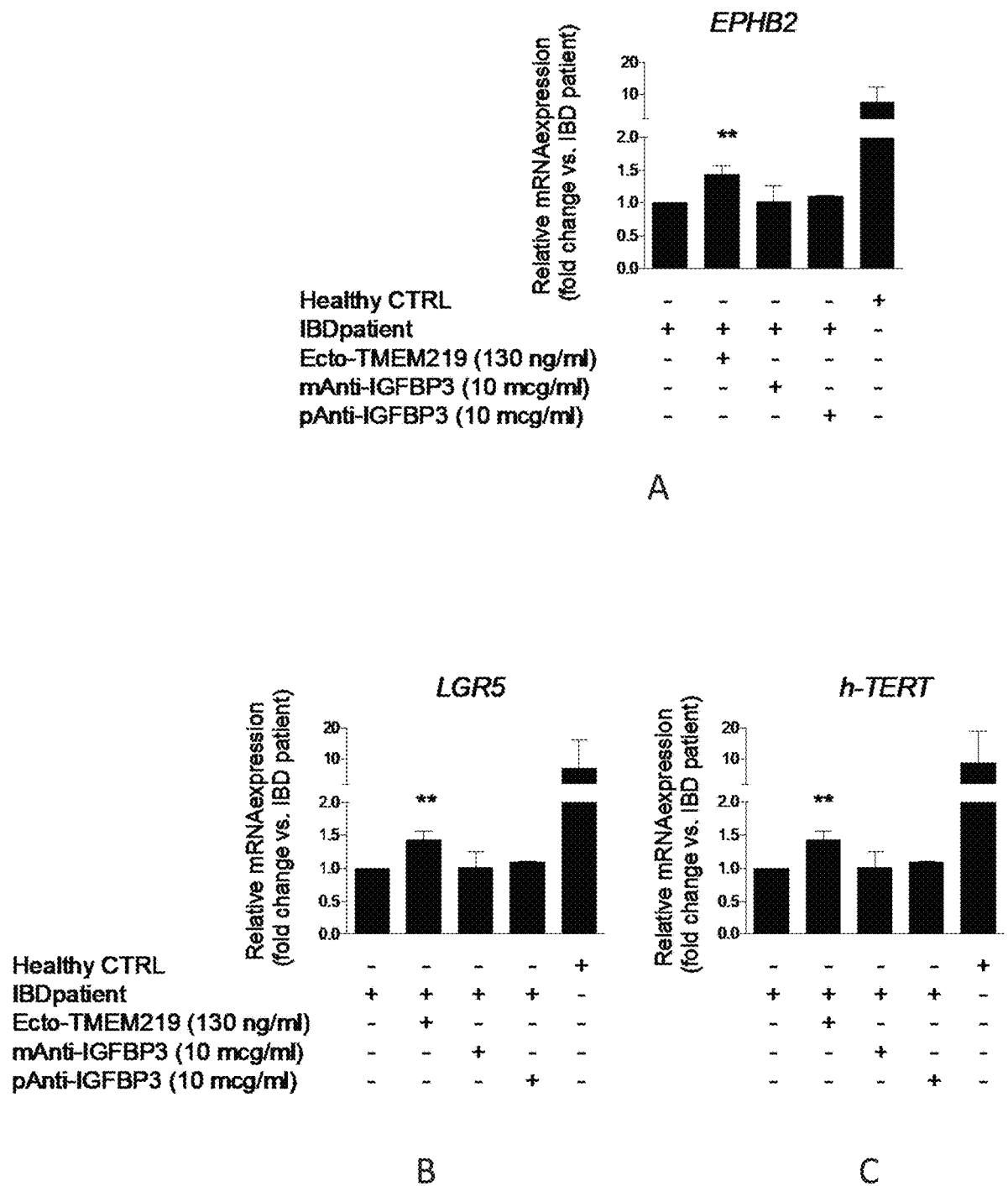
FIG. 4. ISCs (intestinal stem cells) markers expression (A) EphB2, (B) LGR5 and (C) h-TERT analyzed by RT-PCR in mini-guts obtained from Crohn's disease patients (IBD) treated with anti-IGFBP3 commercial antibodies/Ecto-TMEM219 or left untreated (n=3) and in healthy controls (n=3). Monoclonal (clone 83.8F9) and polyclonal antibodies were used at a 1:10 ratio compared to Ecto-TMEM219. **p<0.01 Ecto-TMEM219 vs. IBD patient.

Next, we showed that the expression of the ISC markers EphB2, LGR5, and h-TERT in IBD patients, detected by RT-PCR was not rescued by the addition of commercially available anti-IGFBP3 Abs, in contrast to Ecto-TMEM219 (FIGS. 4A, B and C).

These results confirm the poor effects of the commercial anti-IGFBP3 monoclonal and polyclonal antibodies in targeting ISCs function (mini-guts development) and in rescuing ISC markers expression. This also emphasizes that different disease conditions (e.g. diabetic enteropathy, IBD) in which ISCs are damaged due to the activation of IGFBP3-TMEM219 signaling, may benefit from a strategy that selectively targets it.

Example 3

Novel Anti-IGFBP3 mAbs Inhibit IGFBP3-TMEM219 Binding

Figure 5:
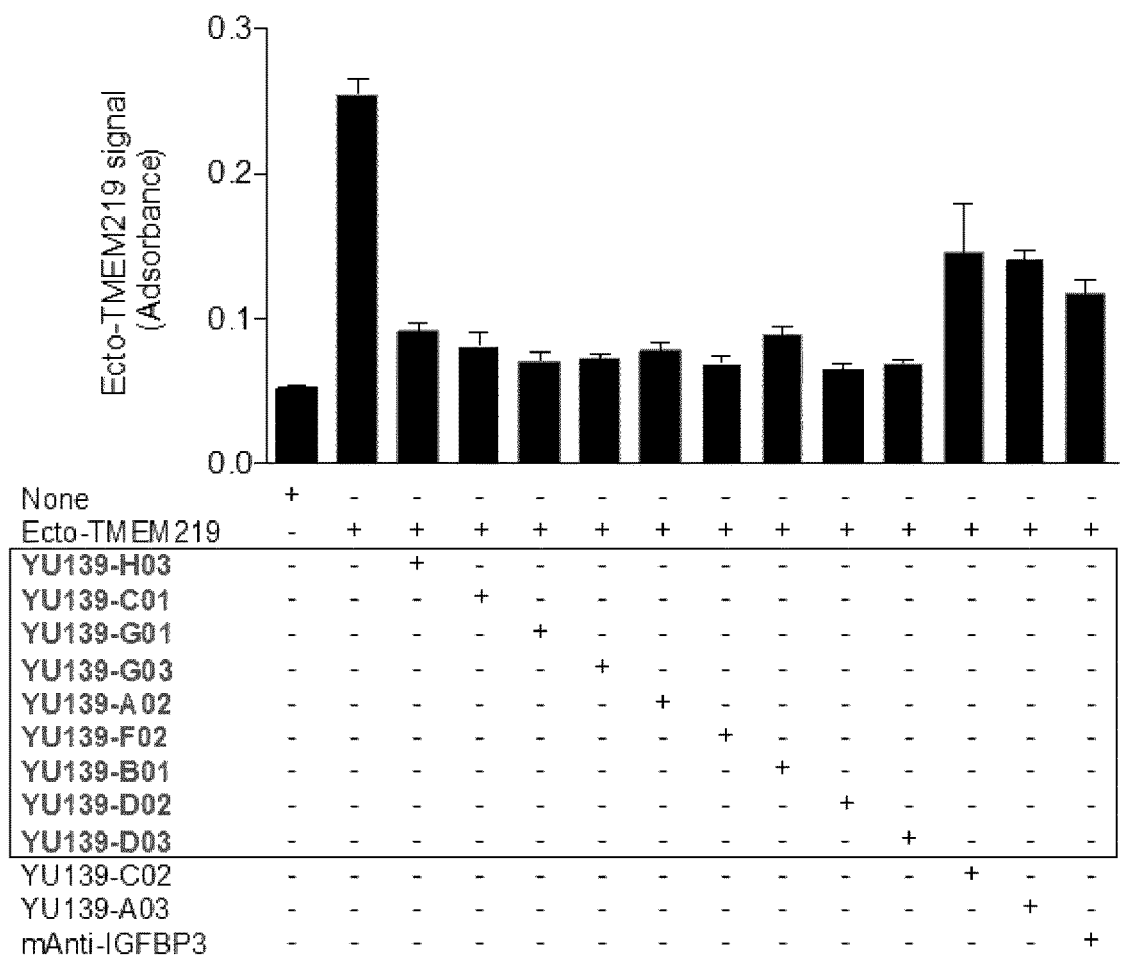
FIG. 5. IGFBP3-Ecto-TMEM219 binding in the presence of newly generated anti-IGFBP3 mAbs (n=11, YU139 antibodies) or Ecto-TMEM219 alone or monoclonal anti-IGFBP3 commercially available (LSBIO LS-C45037/clone 83.8F9, mAnti-IGFBP3) tested by using a competitive ELISA screening assay. In this assay, the microtiter plate was coated with rhIGFBP3, and labeled ecto-TMEM219 added. Each candidate monoclonal antibody was added and its ability to displace ecto-TMEM219 was assessed by measuring Absorbance after the plate was washed. Boxed are anti-IGFBP3 antibodies able to achieve the highest reduction in Ecto-TMEM219 signal (1-way ANOVA, $p<0.00001$).

As discussed in Example 1, a set of anti-IGFBP3 monoclonal antibodies was selected by phage display. These novel antibodies were then screened for their ability to compete with ecto-TMEM for the binding to IGFBP3 using a competitive ELISA binding assay. IGFBP3 (coating), ecto-TMEM219 and the anti-IGFBP3 antibodies selected by phage display were all used in a 1:1 molecular ratio. As shown in FIG. 5, the novel antibodies were capable of inhibiting IGFBP3-ecto-TMEM219 binding, although two of them to a lesser extent. In this assay, the commercially available monoclonal anti-IGFBP3 antibody was poor at inhibiting IGFBP3-ecto-TMEM219 binding.

This demonstrates that the majority of the newly discovered Anti-IGFBP3 mAbs may prevent the IGFBP3-TMEM219 binding to a higher rate as compared to the commercially available anti-IGFBP3 antibody.

Novel Anti-IGFBP3 Antibodies Rescue IGFBP3-Damage in the Mini-Guts Assay

The 11 newly discovered monoclonal antibodies were also tested in the mini-gut assay. Mini-guts were generated from crypts obtained from healthy controls and cultured for 8 days in presence of IGFBP3 and treated with either ecto-TMEM219 or the newly discovered anti-IGFBP3 mAbs All factors were included after the first day of culture at a 1:1 ratio (mAbs/ecto-TMEM219:IGFBP3).

Figure 6:
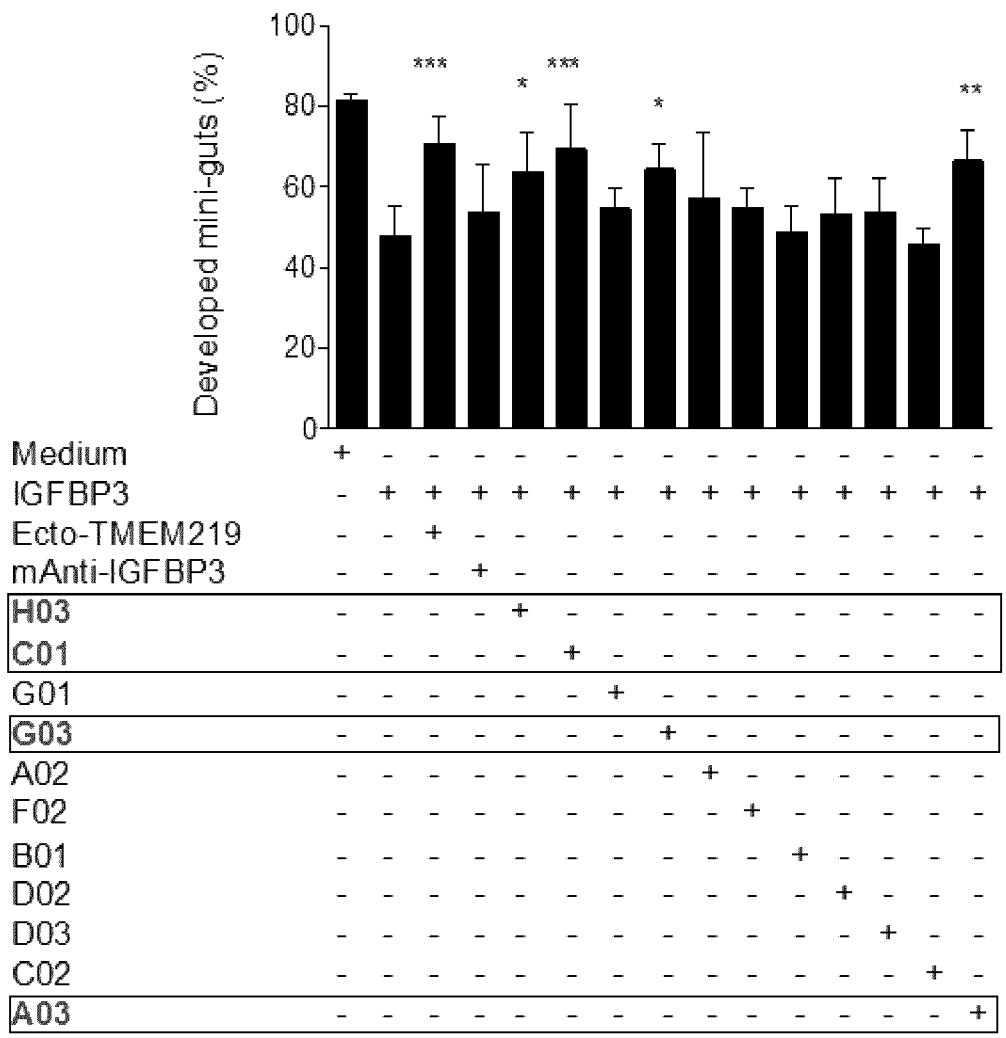
FIG. 6. Effect of anti-IGFBP3 mAbs on mini-gut development upon IGFBP3 exposure. 4 out of 11 of newly generated mAbs significantly rescued mini-guts growth upon IGFBP3 exposure (boxed). *p<0.05, p<0.01, *p<0.001, mAbs/Ecto-TMEM219 vs. IGFBP3. Monoclonal anti-IGFBP3 antibodies were used with 1:1 molecular ratio to IGFBP3 (as Ecto-TMEM219). Commercial monoclonal anti-IGFBP3 antibody was purchased from LSBIO (LSBIO LS-C45037/107162) as described above.
Figure 7:
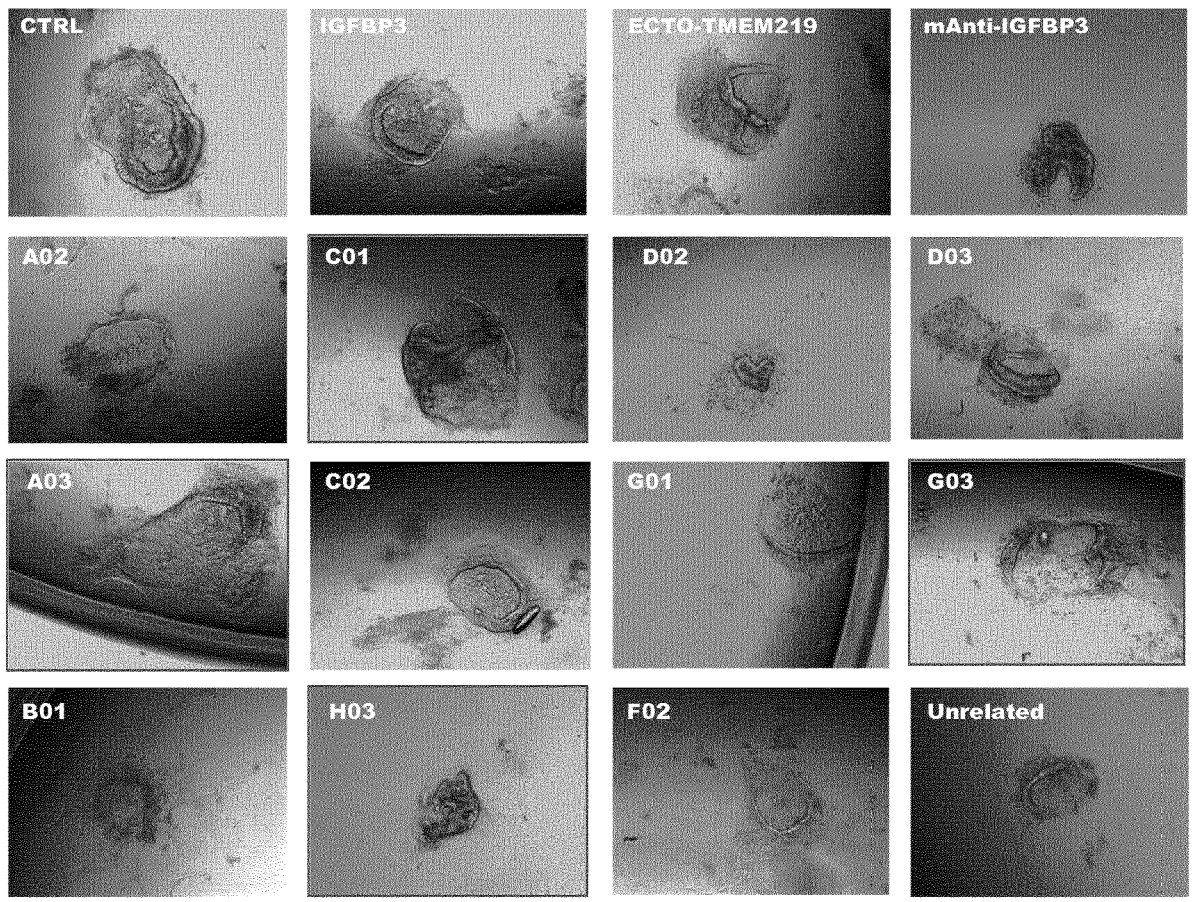
FIG. 7. Effects of anti-IGFBP3 mAbs on mini-gut morphology upon IGFBP3 exposure. 11 newly generated anti-IGFBP3 mAbs, commercial monoclonal anti-IGFBP3 antibody (LSBIO, LS-C45037/107162) and Ecto-TMEM219 were tested on mini-guts treated with IGFBP3 and self-renewal properties were assessed by morphology evaluation. Development of large crypts organoids with at least one crypt domain was considered as main criteria. Unrelated antibody was anti-NLRP3 (IC7578A, R&D Systems). Original magnification X40.

As shown in FIGS. 6 and 7, ecto-TMEM219 rescues the negative effects of IGFBP3 on self-renewal ability (% development) and morphology of large crypt organoids.

Further, antibodies YU139-C01, YU139-A03, YU139-G03, and YU139-H03 also rescue the negative effects of IGFBP3 on self-renewal ability (% development) and morphology (absence of crypts domain, generation of small spheroids) of large crypt organoids (FIGS. 6 and 7), similarly to ecto-TMEM219.

Novel Monoclonal Anti-IGFBP3 Antibodies Rescue IGFBP3-Damage on ISCs Markers

Figure 8:
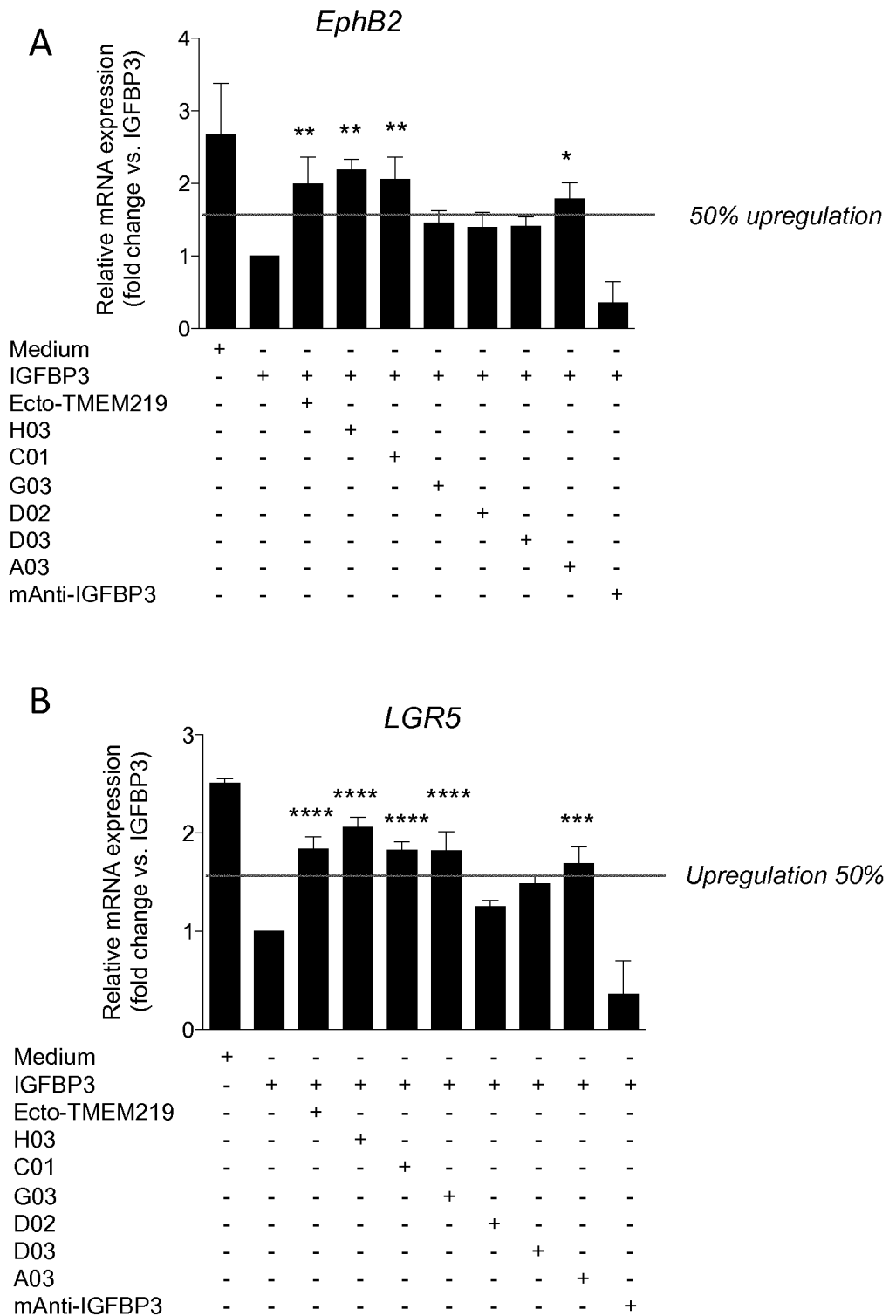
FIG. 8. ISCs markers expression is re-established by newly generated anti-IGFBP3 mAbs in IGFBP3-treated minigut (n=3). Normalized mRNA expression of ISCs markers EphB2 (A) and LGR5 (B) analyzed by using RT-PCR in mini-guts cultured with IGFBP3 and selected anti-IGFBP3 mAbs/Ecto-TMEM219. *p<0.05, **p<0.01 mAbs vs. IGFBP3.

The newly discovered anti-IGFBP3 mAbs which were shown to be effective in promoting mini-guts development upon IGFBP3 exposure were also able to significantly upregulate the expression of ISCs markers EphB2 and LGR5 (FIG. 8) in presence of IGFBP3 by at least 50% compared to samples treated with only IGFBP3. This result is similar to that observed with ecto-TMEM219.

Novel Monoclonal Anti-IGFBP3 Antibodies Inhibit IGFBP3-Mediated Overexpression of Caspase 8

Figure 9:
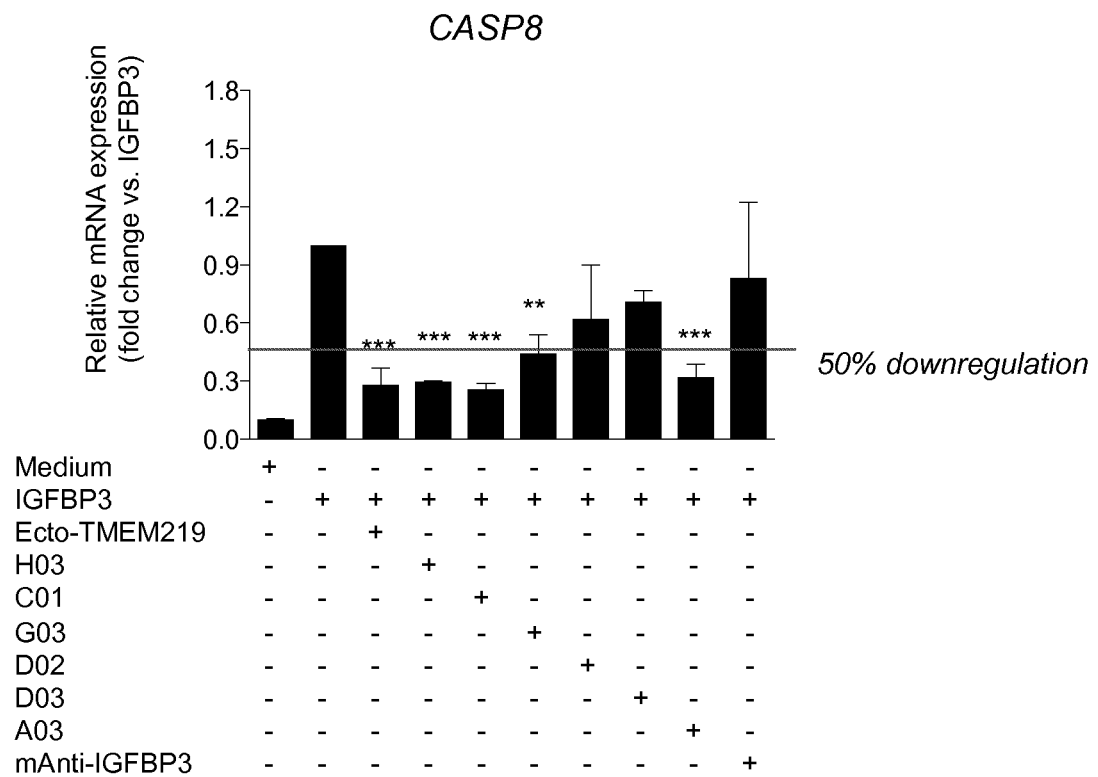
FIG. 9. Caspase 8 expression is down-regulated by newly generated anti-IGFBP3 mAbs in IGFBP3-treated mini-guts. Normalized mRNA expression of Caspase 8 analyzed by using RT-PCR in mini-guts cultured with IGFBP3 and selected anti-IGFBP3 mAbs/Ecto-TMEM219. *p<0.05, **p<0.01 mAbs vs. IGFBP3 (n=3).

IGFBP3-detrimental effects on ISCs are Caspase-8 mediated. Interestingly, newly discovered anti-IGFBP3 mAbs were able to inhibit the caspase-8 upregulation induced by IGFBP3 treatment by at least 50% when compared to samples treated only with IGFBP3 (FIG. 9).

These results suggest that the discovered anti-IGFBP3 mAbs exert a protective effect on ISCs pool by blocking the IGFBP3/TMEM219 Caspase-8-mediated apoptotic injury.

The Newly Discovered Anti-IGFBP3 Antibodies Rescue Mini-Guts Growth in Disease Models.

In order to confirm that the newly discovered monoclonal anti-IGFBP3 antibodies prevent the detrimental effects of IGFBP3 on TMEM219-expressing intestinal stem cells, the inventors further tested them in vitro in the mini-gut assay in an established model of DE.

Figure 10:
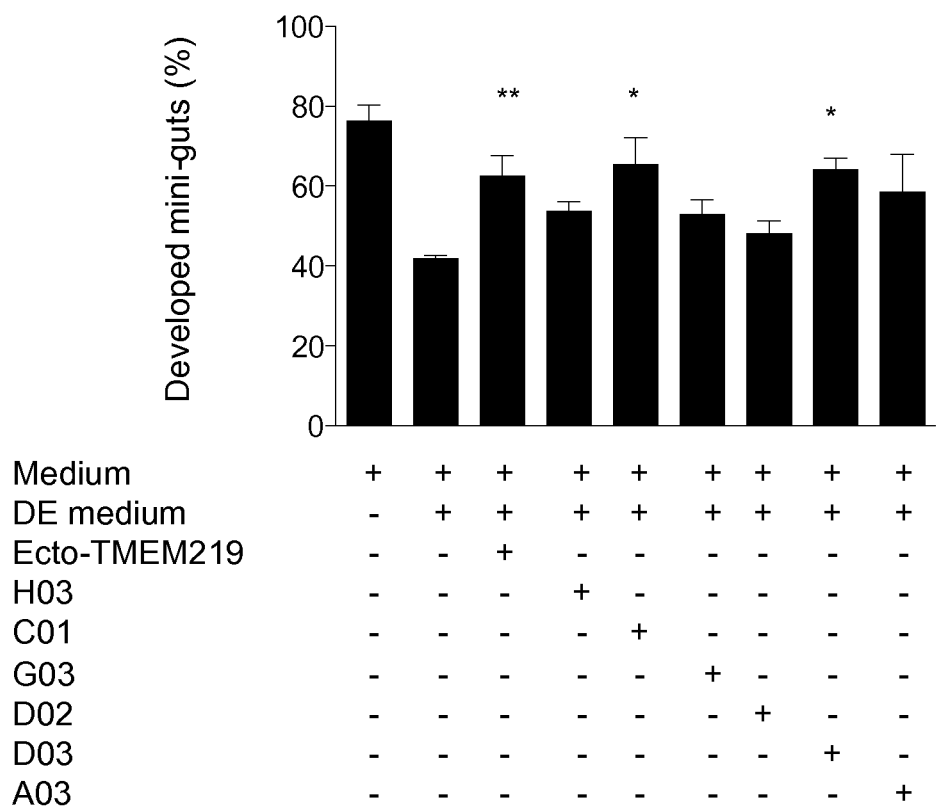
FIG. 10. Effects of anti-IGFBP3 mAbs in rescuing mini-guts growth in DE (n=2). Mini-guts were grown with serum obtained from patients with diabetic enteropathy (DE) as described in the Methods and selected newly generated anti-IGFBP3 mAbs/Ecto-TMEM219 were added. The detrimental effect of on mini-guts growth induced by the DE-conditioning medium was significantly abrogated by some of the anti-IGFBP3 mAbs tested. *p<0.05, **p<0.01 mAbs vs. DE medium.

The novel anti-IGFBP3 mAbs significantly improved the development of mini-guts in DE of at least 20%, similarly to Ecto-TMEM219 treatment (FIG. 10).

This highlights that anti-IGFBP3 mAbs of the invention, selected both for binding to IGFBP3 and screened for their ability to competitively inhibit ecto-TMEM binding to IGFBP3 are capable of rescuing ISCs function and preserve ISCs pool fromIGFBP3-detrimental effects.

Figure 11:
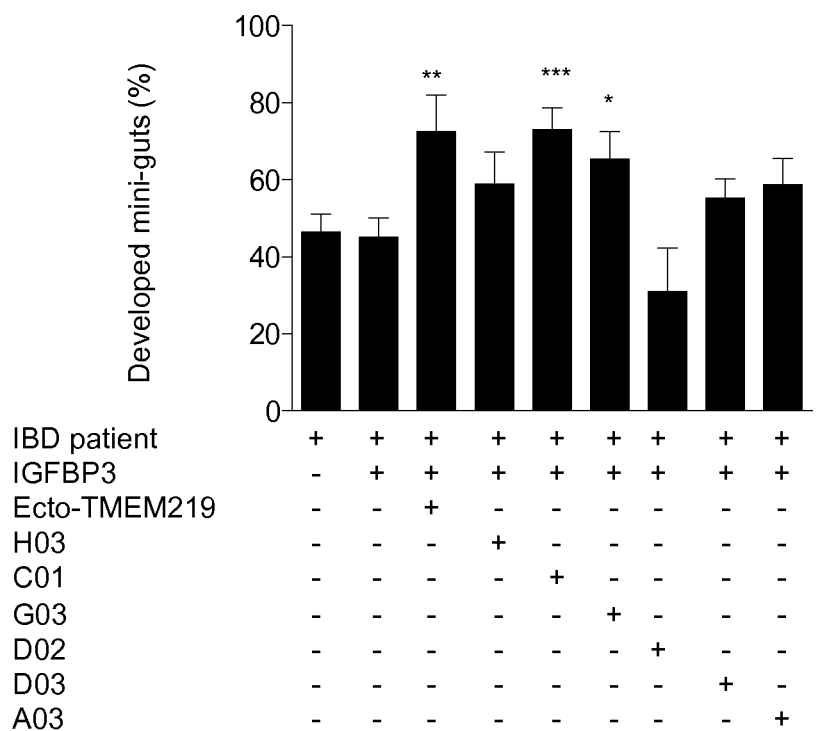
FIG. 11. Effects of anti-IGFBP3 mAbs in rescuing mini-guts growth in IBD (n=3). Mini-guts were obtained from patients with IBD and re-challenged with/without IGFBP3 and newly generated anti-IGFBP3 mAbs/Ecto-TMEM219. Mini-guts development was rescued by some of the anti-IGFBP3 mAbs tested. *p<0.05, p<0.01, *p<0.001 mAbs vs. IBD patient.

The inventors also demonstrated that mini-guts growth was significantly recovered, by at least 20%, when treating mini-guts obtained from IBD patients with the newly discovered anti-IGFBP3 mAbs. The effects obtained with the novel anti-IGFBP3 mAbs were similar to that exerted by ecto-TMEM219 (FIG. 11).

These results show a potential benefit in preserving the ISCs pool and function also in this disease model.

The Newly Discovered Human Monoclonal Anti-IGFBP3 Antibodies Bind a Different Region of the Antigen from the Commercial Mouse Monoclonal Anti-IGFBP3

An epitope binning experiment was performed to check whether commercial antibody LSBIO LS-C45037 (clone 83.8F9) and the newly developed anti-IGFBP3 antibodies bind to the same epitope region of IGFBP3. Briefly, a sandwich ELISA was performed coating the multiwell plate with the prior art antibody. All of the novel anti-IGFBP3 monoclonal antibodies selected by phage display were able to bind to IGFBP3 in the presence of commercial antibody LSBIO LS-C45037 (clone 83.8F9).

Figure 12:
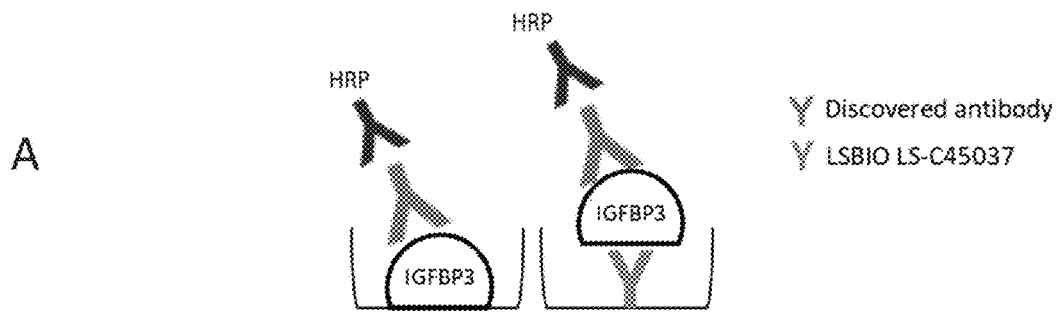
FIG. 12. Epitope binning experiments: (A) IGFBP3 was directly coated on the plate (black line) or captured by the coated commercial antibody (LSBIO LS-C45037/clone 83.8F9) (red line). (B, C, D, E, F, G) A dose-dependent binding is observed for all tested newly generated anti-IGFBP3 antibodies even when IGFBP3 is captured by the commercial LSBIO, LS-C45037/clone 83.8F9 antibody.
Figure 12:
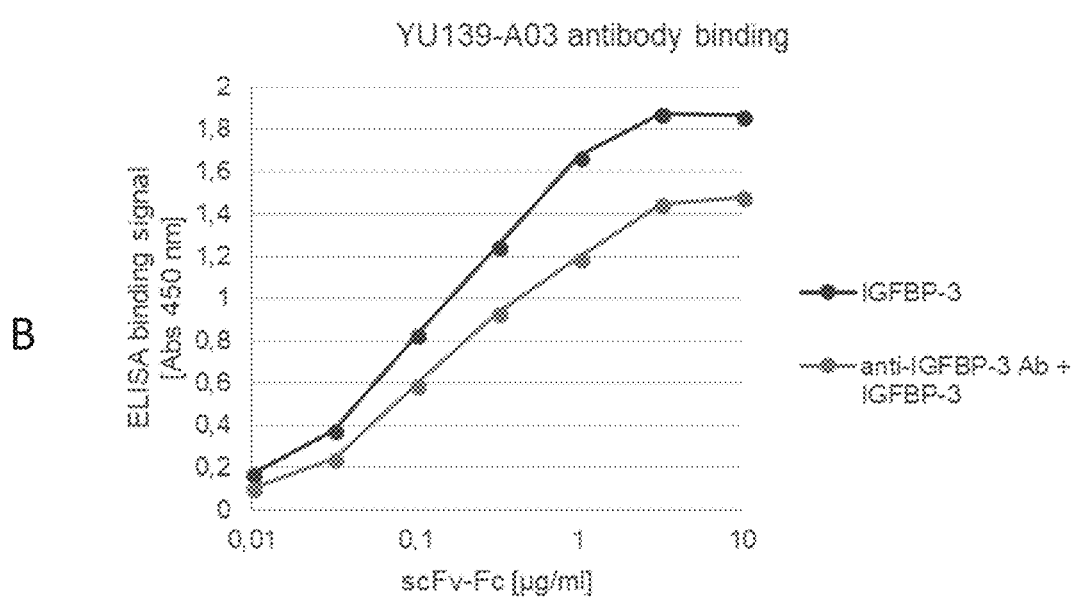
Figure 12:
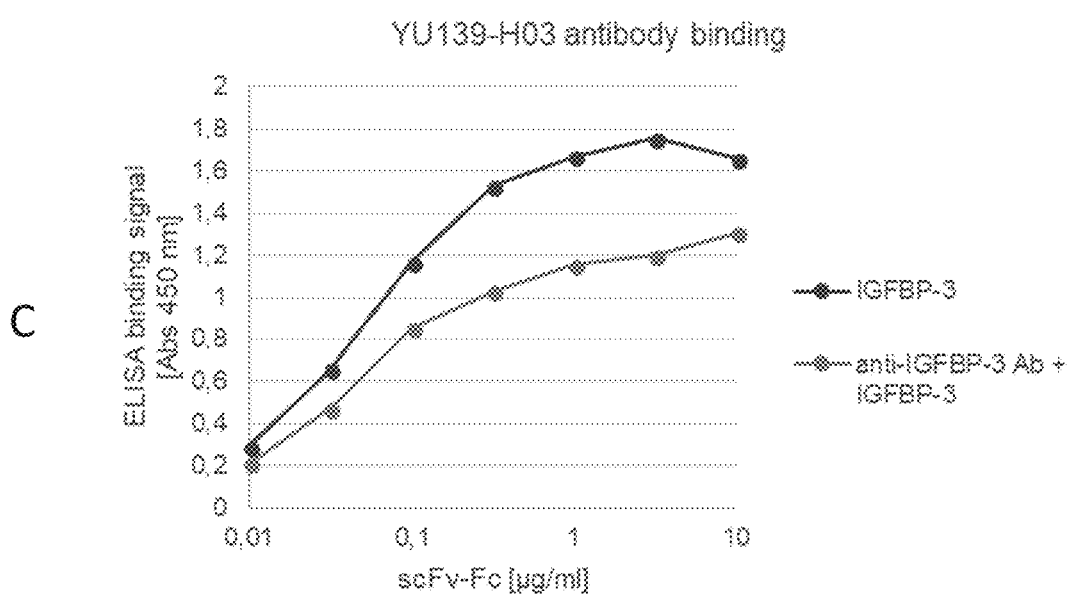
Figure 12:
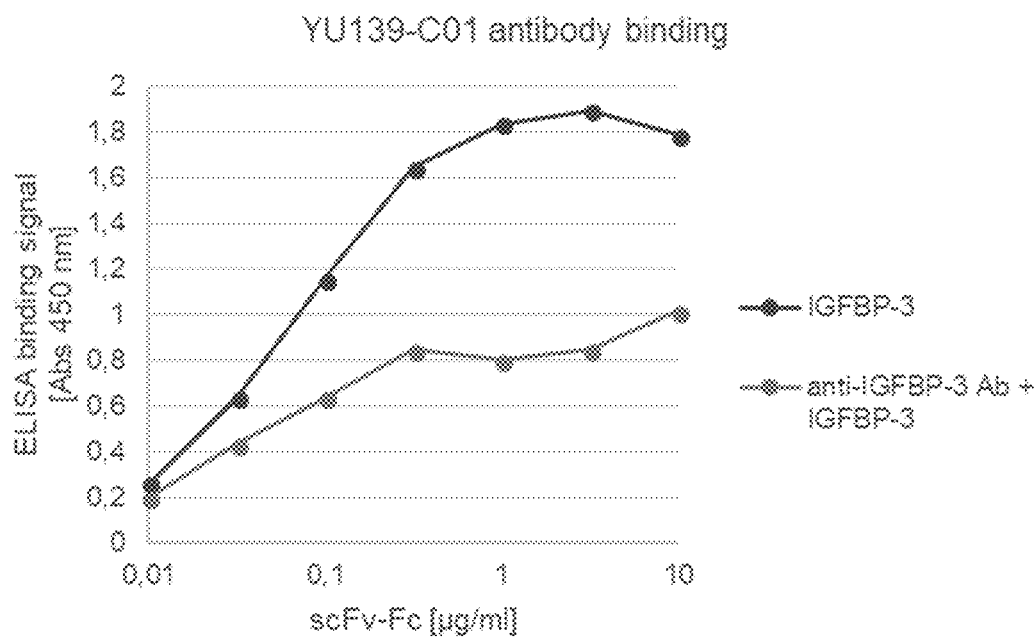
Figure 12:
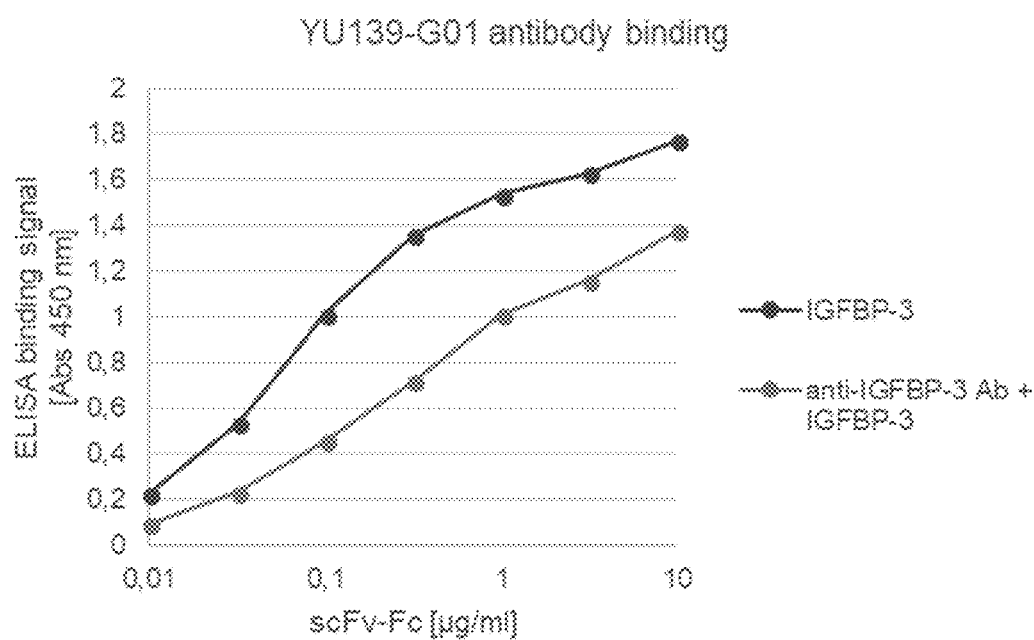
Figure 12:
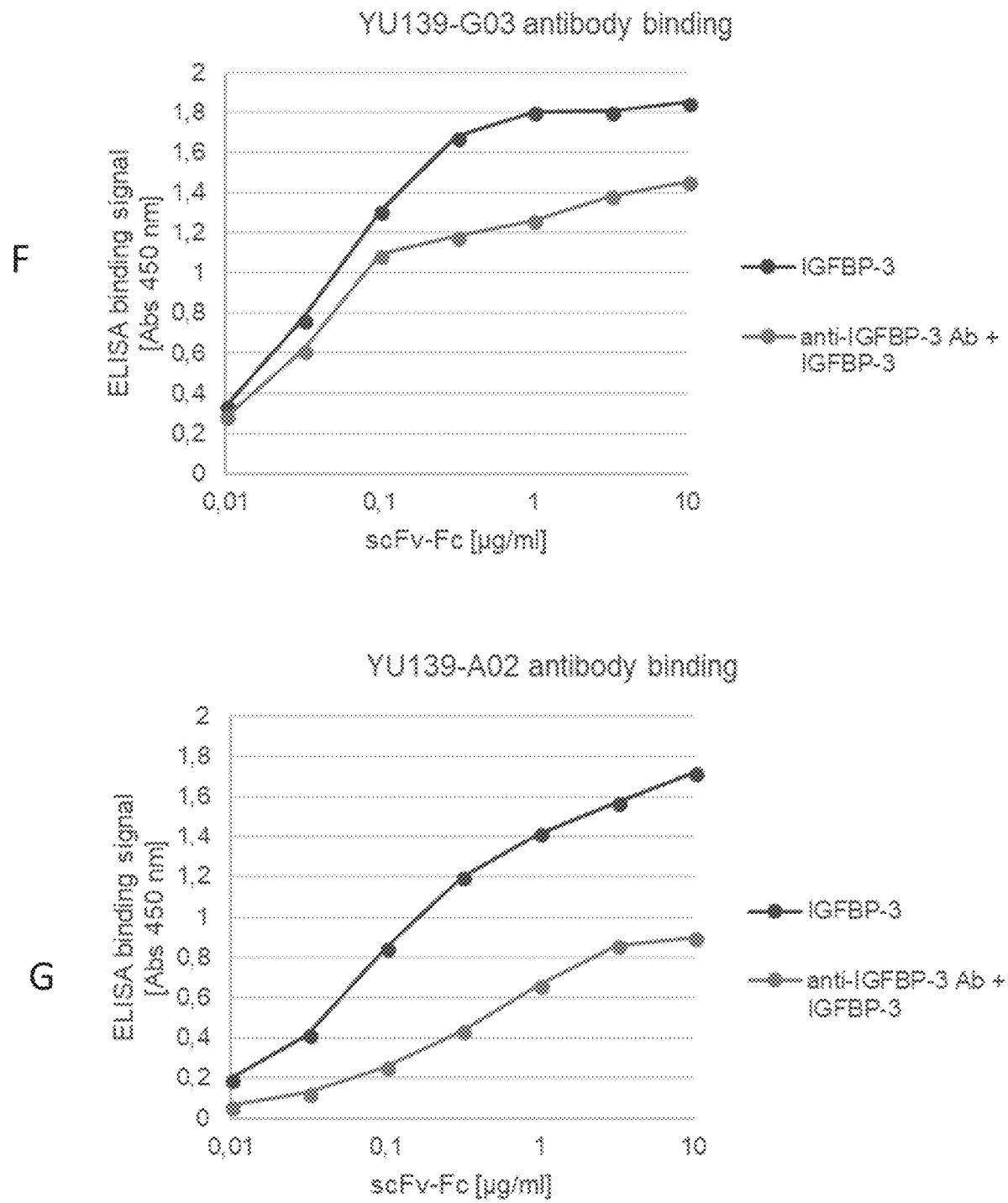

This result suggests that the epitope on IGFBP3 bound by the newly discovered antibodies is different from that of commercially available antibody (FIG. 12).

Example 4

Newly Generated Monoclonal Anti-IGFBP3 Antibodies do not Displace IGF-I-IGFBP3 Binding Competitive ELISA Binding Assay Newly generated anti-IGFBP3 mAbs were tested for their ability to displace the IGF-I-IGFBP3 interaction by using a competitive ELISA in vitro. Briefly, plate was coated with IGFBP3 (Life Technologies) 4 μg/ml. IGF-I (R&D, 291-G1-01M) was added in a dose dependent ratio with IGFBP3 (0:1, 0.5:1 and 2:1). The newly generated anti-IGFBP3 mAbs (Yumab) of the invention were added at a concentration of 1:1 as compared to IGFBP3. IGFBP3-IGF-I binding was revealed by using anti-IGF-I HRP conjugated antibody.

The following reagents were used to screen the anti-IGFBP3 Antibodies: Recombinant Human IGFBP-3 (0,223 mg/ml R&D System, 675-B3-025), IGF-I (R&D, 291-G1-01M), anti-IGFBP3 mAbs (Yumab), mouse monoclonal anti-IGFBP3 (Novus Biological, NBP2-12364), anti-IGF-I HRP (LSBio, C547140), bovine serum albumin (BSA, Sigma A7906), Tween 20 (TW), ELISA colorimetric TMB reagent (HRP substrate, Item H Sigma, RABTMB3), ELISA STOP solution (Item I, Sigma, RABSTOP3), blocking reagent solution (3% BSA in PBS) and a diluent solution (0.5% BSA, 0.05% Tw in PBS). Microplate (Thermofisher, Electron Corporation, 2801) was coated with 50 μl/well of 4 μg/ml rhIGFBP3 dissolved in PBS or PBS alone (no coating). Plate was incubated 90 minutes at 37° C. and washed with PBS (300 μl/well) and incubated with the blocking reagent (200 μl/well) 2 hours at room temperature. Samples were then diluted in the diluent solution (50 μl/well) and added to the plate as following: diluent solution (none), IGF-I at different ratios with rhIGFBP3 (0:1, 0.5:1 and 2:1) and anti-IGFBP3 mAbs at 10 μg/ml. After washing steps, plate was then incubated at room temperature for 1 hour with anti-IGF-I HRP diluted in Diluent solution (50 μl/well). ELISA plate was then read after adding visualization solution at ELISA reader.

Figure 13:
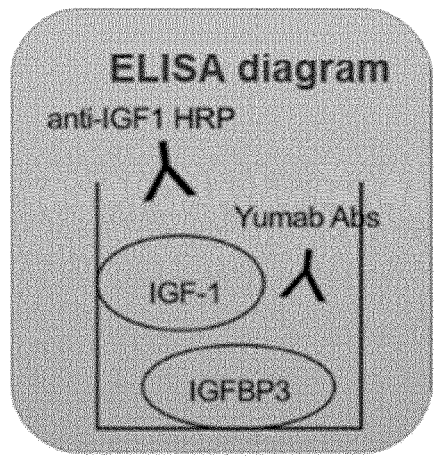
FIG. 13. Newly generated anti-IGFBP3 mAbs were tested for their ability to displace the IGF-I-IGFBP3 interaction by using a competitive ELISA in vitro. Briefly, plate was coated with IGFBP3 (Life Technologies) 4 μg/ml. IGF-I (R&D, 291-G1-01M) was added in a dose dependent ratio with IGFBP3 (0:1, 0.5:1, and 2:1). The anti-IGFBP3 mAbs (Yumab) were added at a concentration of 1:1 as compared to IGFBP3. IGFBP3-IGF-I binding was revealed by using anti-IGF-I HRP conjugated antibody. A commercial monoclonal anti-IGFBP3 antibodies (Novus Biological) was evaluated in the competitive ELISA binding assay as control.
Figure 13:
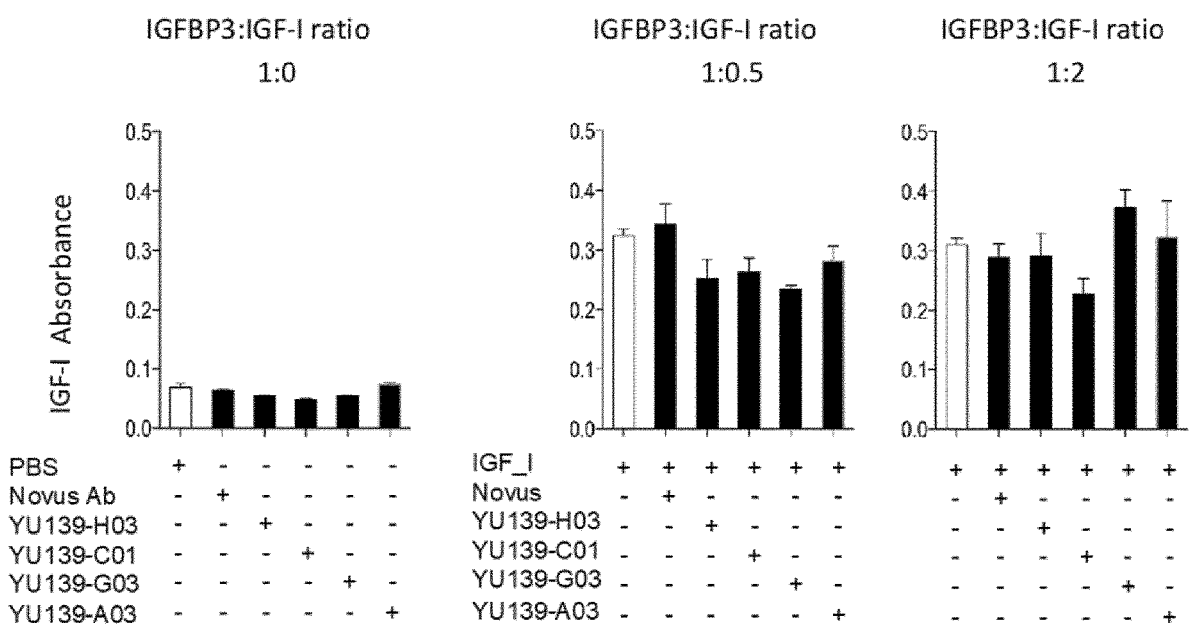

As shown in FIG. 13, newly generated anti-IGFBP3 mAbs did not reduce significatively the absorbance of IGF-I in the assay, indicating that the mAbs are unable to fully displace the IGF-I-IGFBP3 binding at low or high concentration of IGF-I. Overall, the present results confirm that when IGF-I is available, IGFBP3 preferentially binds to it and that newly generated anti-IGFBP3 mAbs do not interfere with the IGFBP3-IGF-I binding in vitro.

In other words, when IGF1 is available, IGFBP3 preferentially binds to IGFF1 and the newly generated mAbs do not interfere with the IGF1-IGFBP3 binding.

Newly Generated Monoclonal Anti-IGFBP3 Antibodies Rescue IGFBP3-Damage in Murine Mini-Guts Crypts Isolation and Murine Mini-Guts Development In order to confirm that the present invention antibodies have a similar tissue cross-reactivity profile in murine tissue in respect to the human tissues, the inventors further tested the monoclonal anti-IGFBP3 antibodies of the invention in the in vitro mini-gut assay in murine crypts. Crypts were obtained from C57BL/6J mice (632C57BL/6J Charles River Laboratories, Lyon, France). Briefly, the colon was cut into 2-4 mm pieces with scissors and fragments were washed in 30 ml of ice-cold PBS and then incubated with 20 mM EDTA-PBS at 37° C. Then, fragments were treated trypsin/DNAse solution to obtain crypts. After this step, vigorous shaking of the sample yielded supernatants enriched in colonic crypts. Crypts were mixed with Matrigel and plated on pre-warmed culture dishes. After solidification of matrigel (10-15 min at 37° C.), crypts were overlaid with culture medium (ADF, 10 mM HEPES, N-2, B27 without retinoic acid, 10 µM Y-27632, 1 µM JAG1 peptide (Anaspec, Fremont, CA, USA), 1 g/ml R-Spondin 1, 50 ng/ml EGF (Invitrogen), and 100 ng/ml Noggin (Peprotech, Rocky Hill, NJ, USA), and medium was changed every other day until day 8.

Isolated crypts were cultured to generate large crypts organoids namely mini-guts for 8 days in the presence of IGFBP3 with/without ecto-TMEM219. Newly generated anti-IGFBP3 mAbs were added at day 0 at a ratio of 1:1 (mAbs/ecto-TMEM219:IGFBP3). Miniguts development was calculated as a percentage of organoids growth after 8 days as compared to the plated isolated crypts (D'Addio F et al. Cell Stem Cell 2015 Oct. 1; 17 (4): 486-498).

Figure 14:
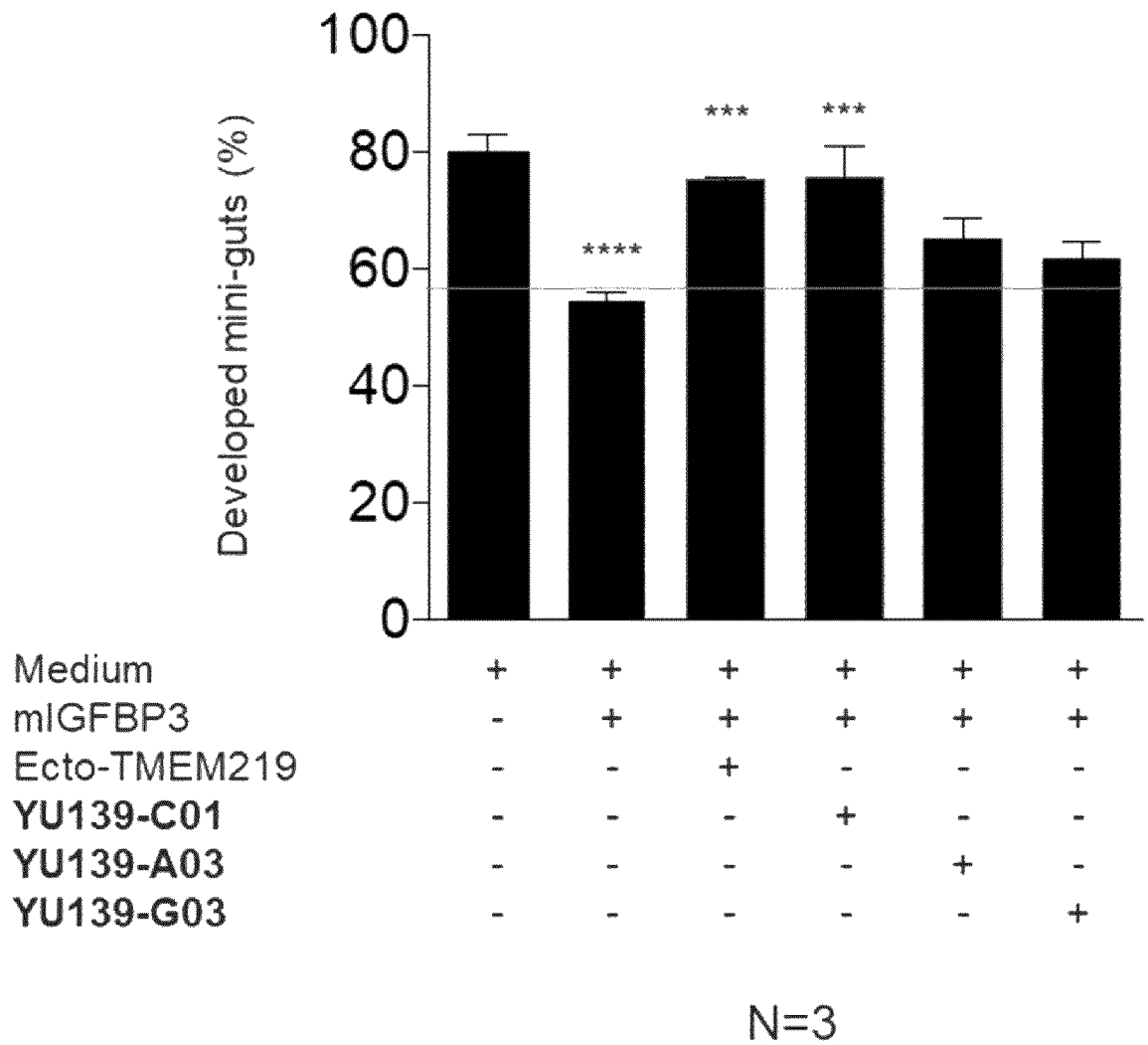
FIG. 14. Newly generated monoclonal antibodies were tested in the murine mini-gut assay. Briefly, mini-guts were generated from crypts obtained from control mice C57BL6/J (n=3) and cultured for 8 days upon IGFBP3 exposure and treated with either ecto-TMEM219 or anti-newly generated IGFBP3 mAbs at a ratio of 1:1 (mAbs/ecto-TMEM219: IGFBP3).

As shown in FIG. 14, antibodies YU139-C01, YU139-A03, YU139-G03, and YU139-H03 rescue the negative effects of IGFBP3 on murine mini-gut self-renewal ability (% development) and morphology (absence of crypts domain, generation of small spheroids) of large crypt organoids, similarly to what is observed for ecto-TMEM219.

Affinity Measurement

Octet BLI-Based Analysis

To assess the binding affinity in more detail, affinity measurements were performed using Biomolecular Interaction Analysis performed by an Octet instrument (BLItz System), which is a Biolayer Interferometry (BLI) platform. To establish the assay, the target monoclonal antibody (30 µg/ml in 1% BSA-PBST) was immobilized via Fc on the via AHC biosensor and the interaction with the antigen human IGFBP3 (R&D, cat n° 675 B3) and mouse IGFBP3 (Creative Biomart, cat n° igfbp3 829M) at different concentration was measured.

The affinity measurement of YU139-C01, YU139-H03, YU139-G03 and YU139-A03 for the target human and murine IGFBP3 are reported in the Table 9.

TABLE 9

Affinity of YU139-C01, YU139-H03, YU139-G03 and YU139-A03 for the target human and murine IGFBP3.

| Molecule id | EctoTMEM-His | YU139-C01 | YU139-H03 | YU139-A03 |
| --- | --- | --- | --- | --- |
| hIGFBP-3 KD (M) | $3.5 \times 10^{-8}$ | $1.69 \times 10^{-9}$ M | $4.0 \times 10^{-6}$ | $3.28 \times 10^{-7}$ |
| mIGFBP-3 KD (M) | $6.0 \times 10^{-8}$ | $3.42 \times 10^{-7}$ | $>10^{-6}$ | $7.35 \times 10^{-7}$ |

Newly generated anti-IGFBP3 mAbs show good human antigen binding affinity with KD below $4 \times 10^{-6}$ M. The antibodies also show murine cross reactivity. This data confirmed that mice can be considered a relevant animal species for testing of the monoclonal antibodies during preclinical development.

Anti-IGFBP3 mAbs Efficacy in IBD Mouse Model Following Intraperitoneal (IP) Administration The model of colitis induced by Dextran sulfate sodium (DSS) in C57BL/6J mice is a validated animal model to evaluate and also to confirm the anti-inflammatory properties of drugs in IBD. DSS (oral administration in the drinking water) induces prominent diarrhea followed by inflammation. This model is well characterized, reliable, reproducible and admitted by regulatory authorities in IBD with no mortality. This study was performed in C57BL/6J mice. Indeed, in this particular genetic background, mice develop acute colitis when analyzed 3 days after the last DSS administration or a chronic-like inflammation when analyzed 7 days after the last DSS administration.

Animals

Male C57BL/6J mice were supplied by Charles River laboratories, l'Arbresle, France. The mice were housed at 20±5° C. and provided with water and food ad libitum. All experimental protocols were performed in accredited facilities at Institut Pasteur from Lille according to governmental guidelines.

Establishment of DSS-Induced Mice Colitis Model and Treatment

Acute colitis was induced by feeding mice with 2.5% (w/v) DSS (45 kD; TDB Consultancy AB, Uppsala, Sweden, Batch number DB001-41) dissolved in drinking water for 5 days. The mice were randomly divided into eight groups: control group; DSS+vehicle; DSS+Yu139-CO1 0.6 mg/mouse, DSS+Ecto-TMEM 0.1 mg/mouse, DSS+mouse anti-TNFα 0.1 mg/mouse (Ozyme, B270358), DSS+Pentoxifylline (Sigma P1784, BCBQ05 15), DSS+Humira (Abbvie, 1108722) ip, DSS+Humira sc. To assess the preventive therapeutic effects of anti-IGFBP3 mAb on DSS-induced acute colitis in C57BL/6J mice, the mice were treated daily by intraperitoneal administration with indicated dose of Yu139-CO1 starting 3 days before colitis induction and were performed until euthanasia occurring 7 days after the last DSS administration. The experimental timelines of the animal model are described in FIG. 15A.

The therapeutic properties of the biologics were compared to those induced by positive control groups, mouse anti-TNFα antibody, Pentoxifylline and Humira (Taghipour N. et al Gastroenterol Hepatol Bed Bench 2016; 9 (1): 45-52).

Figure 15:
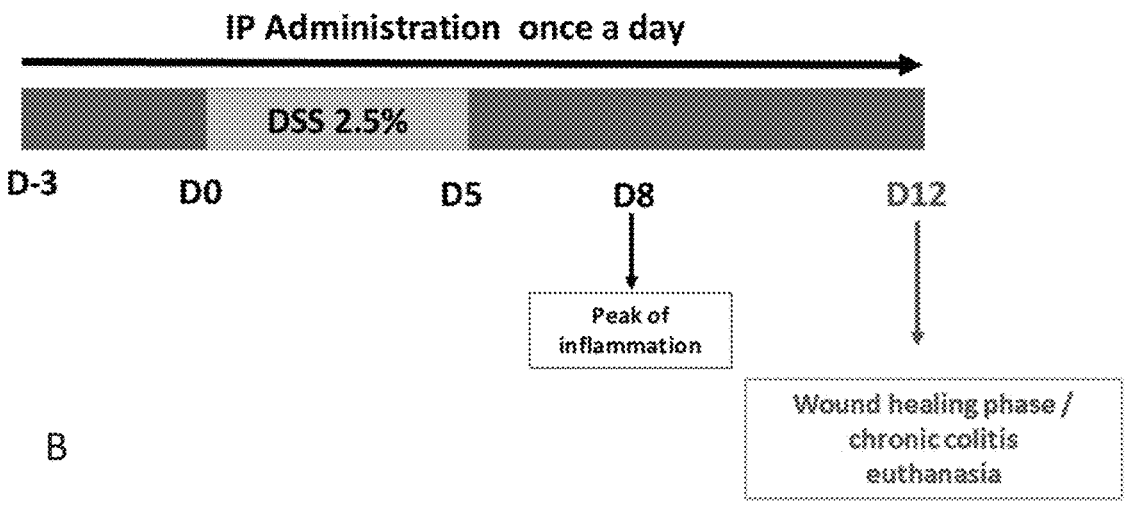
FIG. 15. Effect of newly generated anti-IGFBP3 mAbs on DSS-induced colitis in mice (A) Experimental timelines of DSS-induced colitis mice study, (B) Disease activity index (DAI) score, Blood in Stool (C) and Colon Size (D) were evaluated 7 days after the last administration of DSS during the wound healing/beginning of the chronic phase.
Figure 15:
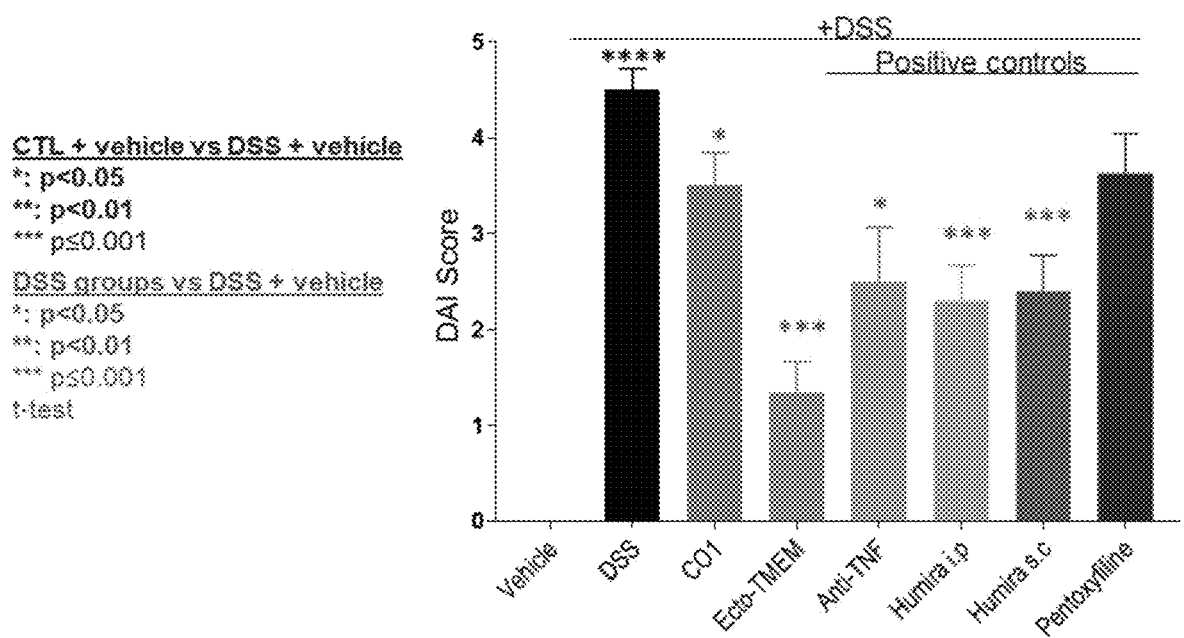
Figure 15:
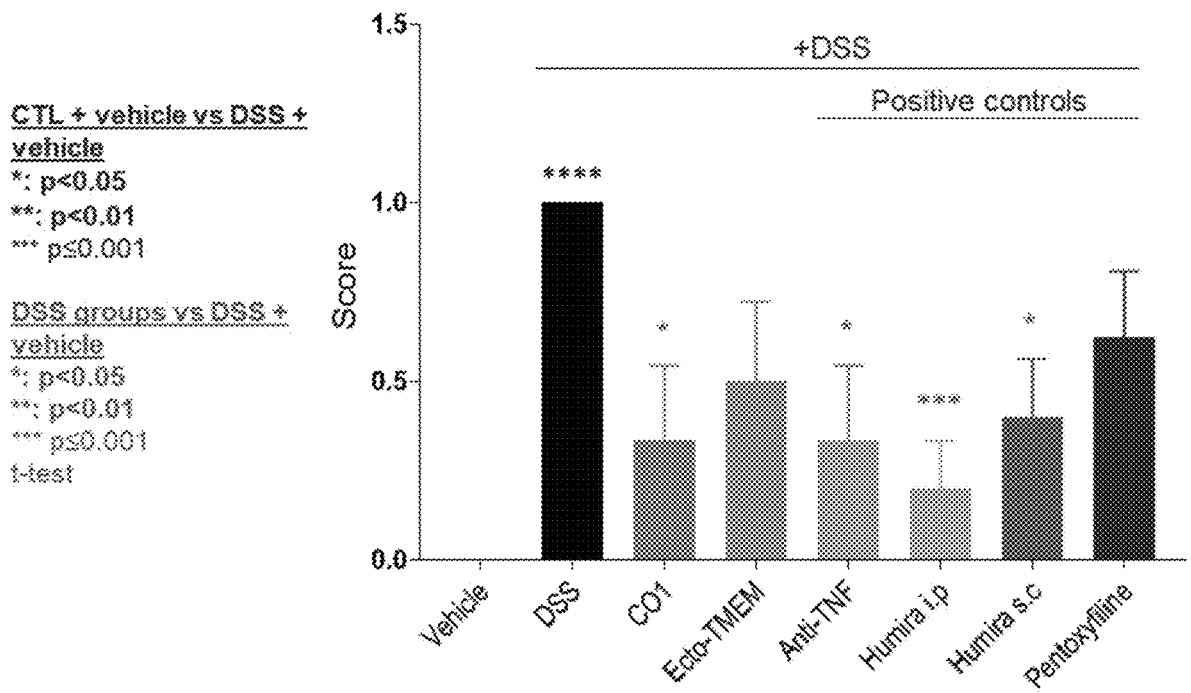
Figure 15:
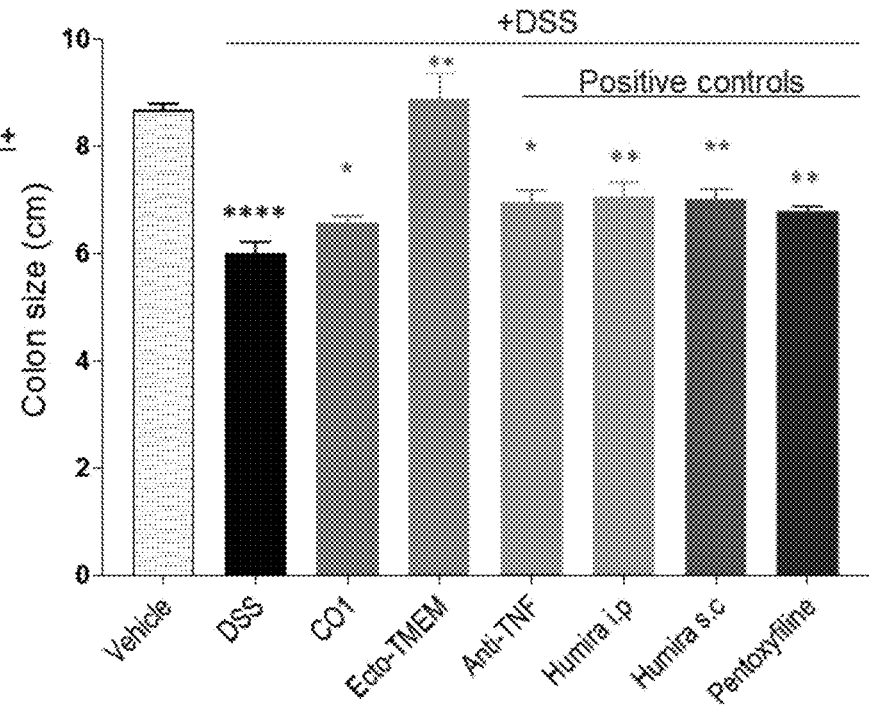

As shown on FIG. 15B, in the group of DSS mice receiving the vehicle, 7 days after the last administration of DSS, the DAI score was significantly increased compared to healthy control group (group receiving vehicle only) indicating the severity of the colitis.

A significant decrease in the DAI score was recorded in colitic mice receiving Yu139-CO1, Ecto-TMEM219, Humira and mouse anti-TNFα antibody compared to DSS mice receiving only the vehicle. This result indicates an anti-inflammatory effect of the newly generated anti-IGFBP3 mAbs.

As shown on FIG. 15C, a significant decrease of the presence of occult blood was recorded in DSS mice receiving a treatment with Yu139-CO1, Humira (the biologic benchmark used in the treatment of IBD patients, used to treat rheumatoid arthritis, psoriatic arthritis, ankylosing spondylitis, Crohn's disease, ulcerative colitis, psoriasis, hidradenitis suppurativa, uveitis, and juvenile idiopathic arthritis) and mouse anti-TNFα antibody, compared to colitic mice receiving the vehicle.

FIG. 15D shows a significant increase of the size of the colon in colitic mice receiving Yu-139-CO1, and the 4 positive controls, indicating therapeutic properties of the newly generated anti-IGFBP3 mAbs.

Clinical Scoring

In all groups, mice weight, stool consistency and blood in stool were recorded daily. The disease activity index (DAI) scores were based on changes in body weight, consistency of stool, and hemoccult bleeding according to a standard scoring system. These parameters were assessed on a scale as described in the Table 10. The DAI data are presented as an average score of these parameters taken daily. Animals were sacrificed by cervical dislocation under anesthesia. At euthanasia, colons were carefully dissected, and its weight and size were measured. At euthanasia, the presence of Occult Blood (OB) is recorded using the hemoccult method.

TABLE 10

Parameters assessed for DAI score

| | Parameters | Scores |
|---|---|---|
| Disease Activity Index (DAI) (0-5) | Weight loss | 0: no; 1: <10%; 2: ≥10% |
| | Stool consistency | 0: regular; 1: soft; 2: diarrhea |
| | Blood occurrence | 0: absence; 1: presence |

Statistical Analysis

All comparisons were analysed using the Permutation Test for two independent samples. Statistics have been calculated using the GraphPad Prism version 7.0 (GraphPad Software, San Diego, CA). Differences were considered statistically significant if the p value was <0.05.

Anti-IGFBP3 mAbs Efficacy in T1D Mouse Model Following Intraperitoneal (IP) Administration Animals Female non-obese diabetic (NOD) mice (10 weeks old) were obtained from the Jackson Laboratory, Bar Harbor, Maine (JAX stock #001976). All mice were cared for and used in accordance with institutional guidelines approved by the Jackson Laboratory Institutional Animal Care and Use Committee.

Diabetes Monitoring and Treatment

Overt diabetes (the most advanced stage, characterized by elevated fasting blood glucose concentration and classical symptoms) was defined as blood glucose levels above 300 mg/dL. Blood glucose was measured using the Breeze2 (Bayer S.p.A) blood glucose meter.

The experiment was randomly divided into three groups: control group; Yu139-CO1 0.25 mg/mouse and Ecto-TMEM 0.1 mg/mouse. To determine whether the anti-IGFBP3 mAb prevents diabetes in NOD mice, animals were treated daily for 10 days by intraperitoneal administration with the indicated dose of Yu139-CO1. The experimental timelines are described in FIG. 16A.

Statistical Analysis

Data are presented as mean and standard deviation (SD) and were tested for normal distribution with the Kolmogorov-Smirnov test and for homogeneity of variances with Levene's test. The statistical significance of differences was tested with two-tailed t-test and the chi-square ($\chi^2$) tests. Significance between the two groups was determined by two-tailed unpaired Student's t test. For multiple comparisons, the 1-way ANOVA test with Bonferroni correction was employed. Diabetes incidence among different groups was analyzed with the log-rank (Mantel-Cox) test. Statistical analysis was conducted using GraphPad Prism version 7.0 (GraphPad Software, La Jolla, CA). All statistical tests were performed at the 5% significance level.

Figure 16:
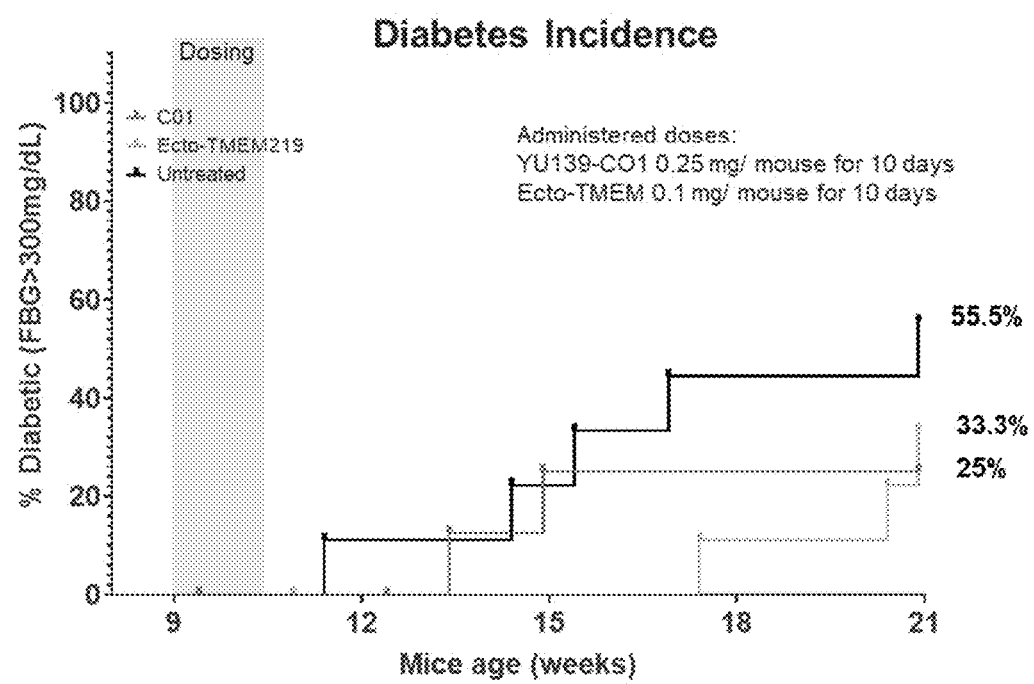
FIG. 16. Effect of newly generated anti-IGFBP3 mAbs on type-1 diabetes mice model (A) Experimental timelines of NOD mice study, (B) Anti-IGFBP3 mAbs effect on incidence of type-1 diabetes in female NOD mice detected at 21 weeks of age, diabetes prevention by anti-IGFBP3 mAbs was observed in 75% of mice.

As shown in FIG. 16B, the inventors assessed if 10 days of newly generated anti-IGFBP3 mAb administration could be effective to prevent clinical diabetes in NOD mice. Remarkably, Anti-IGFBP3 mAbs given by the intraperitoneal (IP) route keep blood glucose under control and are effective in preventing Diabetes in T1D NOD mouse model. This treatment induced diabetes prevention in 75% of the mice with 21 weeks of age.

INCORPORATION BY REFERENCE

All publications, patents, patent applications and other documents cited in this application are hereby incorporated by reference in their entireties for all purposes to the same extent as if each individual publication, patent, patent application or other document were individually indicated to be incorporated by reference for all purposes.

EQUIVALENTS

While various specific embodiments have been illustrated and described, the above specification is not restrictive. It will be appreciated that various changes can be made without departing from the spirit and scope of the invention (s). Many variations will become apparent to those skilled in the art upon review of this specification.

REFERENCES

1. Baxter R C. J Cell Commun Signal. 2013; 7 (3): 179-89.
2. Oh Y, et al., Prog Growth Factor Res. 1995; 6 (2-4): 503-12.
3. Ingermann A R, et al. IThe Journal of biological chemistry. 2010; 285 (39): 30233-46.
4. D'Addio F, et al. Cell stem cell. 2015; 17 (4): 486-98.
5. Brennand K, and Melton D. J. of cellular and molecular medicine. 2009; 13 (3): 472-87.
6. Yi P, Park J S, and Melton D A. Cell. 2014; 159 (3): 467-8.
7. Ben Nasr M, et al., Pharmacological research: the official journal of the Italian Pharmacological Society. 2015; 98:31-8.
8. Keenan H A, et al. Diabetes. 2010; 59 (11): 2846-53.
9. Meier J J, et al., Diabetologia. 2005; 48 (11): 2221-8.
10. Atkinson M A, et al., Diabetes care. 2015; 38 (6): 979-88.
11. Nguyen K H, et al., Endocrinology. 2011; 152 (6): 2184-96.
12. Yakar S, et al., FASEB J. 2009; 23 (3): 709-19.
13. Drogan D, et al., Am J Epidemiol. 2016; 183 (6): 553-60.
14. Peet A, et al., Eur J Endocrinol. 2015; 173 (2): 129-37.
15. Kaplan G G. Nat Rev Gastroenterol Hepatol. 2015; 12 (12): 720-7.
16. Cui S, and Chang P Y. World J Gastroenterol. 2016; 22 (31): 7099-110.
17. Yancu D, et al., J Gastroenterol Hepatol. 2017; 32 (1): 146-53.
18. Jung P, et al., Nature Medecine 2011; 17:1225-1227.
20. George M J, et al., Curr Diab Rep 2013; 13 (1): 72-80.
21. Marsha J D. Am Health Drug Benefits 2011; 4 (5): 312-322
22. Dhingra A K et al., Antiinflamm Antiallergy Agents Med Chem. 2015; 14 (2): 81-97.
23. Pithadia A B, SunitaJ. Pharmacoligal rep 2011; 63:629-642

24. Zhe Wang, et al., Expert Opin Drug Deliv. 2010 February; 7 (2): 159-71
25. Sumit G, Wei W, Tsutomu and Satoshi O, Antibodies 2013; 2:452-500;
26. Beck A, et al., Nat Rev Imm 2010; 10:345-352
27. Huch M, et al., Nature 2013; 494 (7436): 247-250
28. Mahé M M, et al., Curr Protoc Mouse Biol 2013; 3:217-240
29. Shimkets R A, Gene Expression Profiling. Meth. in Mol. Biology; 258. Humana Press
30. Raghavachari N, et al., Gene Expression Analaysis, Meth. in Mol. Biol; 1783. Humana Press
31. Kurien B T, et al., Western Blotting, Methods in Molecular Biology; 1312. Humana Press
32. Hnasko R, ELISA, Methods in Molecular Blology, 1318. Humana Press
33. Lipton M S, et al., Mass Spectrometry of Proteins and Peptides, Meth. in Mol. Biology, 492. Humana Press
34. Brady H, Apoptosis Methods and Protocols, Methods in Moelcualr Biology, 282. Humana Press
35. Cheryl L et al., Protein-Protein interactions, Methods in Molecular Biology, 1278. Humana Press
36. Lightfoot Y L, Chen J, Mathews C E, PLOS One. 2011; 6 (6): e20617.

The invention claimed is:

1. An isolated antibody or antigen binding fragment thereof capable of binding to human insulin-like growth factor binding protein 3 (IGFBP3), wherein the antibody or antigen binding fragment comprises three heavy chain CDRs and three light chain CDRs, wherein the six CDRs are:
Yu139-C01: SEQ ID NO:4 (VH CDR1), SEQ ID NO:11 (VH CDR2), SEQ ID NO:20 (VH CDR3), SEQ ID NO:30 (VL CDR1), SEQ ID NO:39 (VL CDR2), and SEQ ID NO:48 (VL CDR3).

2. The isolated antibody or antigen binding fragment thereof of claim 1, wherein the VH region has the sequence of SEQ ID NO:58 and the VL region has the sequence of SEQ ID NO:69.

3. The isolated antibody or antigen binding fragment thereof of claim 1, wherein the antibody or antigen binding fragment thereof is humanized.

4. The isolated antibody or antigen binding fragment thereof of claim 1, wherein the antibody or antigen binding fragment thereof is human.

5. The isolated antibody or antigen binding fragment thereof of claim 1, wherein the antibody or antigen binding fragment thereof is a humanized or human IgG2 or IgG4 antibody.

6. A pharmaceutical composition comprising an antibody or antigen binding fragment thereof capable of binding to human IGFBP3, wherein the antibody or antigen binding fragment comprises three heavy chain CDRs and three light chain CDRs, wherein the six CDRs are:
Yu139-C01: SEQ ID NO:4 (VH CDR1), SEQ ID NO:11 (VH CDR2), SEQ ID NO:20 (VH CDR3), SEQ ID NO:30 (VL CDR1), SEQ ID NO:39 (VL CDR2), and SEQ ID NO:48 (VL CDR3);
and
a pharmaceutically acceptable diluent or excipient.

7. An isolated polynucleotide or plurality of isolated polynucleotides encoding an antibody or antigen binding fragment thereof capable of binding to human IGFBP3, wherein the antibody or antigen binding fragment comprises three heavy chain CDRs and three light chain CDRs, wherein the six CDRs are:
Yu139-C01: SEQ ID NO:4 (VH CDR1), SEQ ID NO:11 (VH CDR2), SEQ ID NO:20 (VH CDR3), SEQ ID NO:30 (VL CDR1), SEQ ID NO:39 (VL CDR2), and SEQ ID NO:48 (VL CDR3).

8. A method of treating a disorder selected from diabetes, diabetic enteropathy, and inflammatory bowel disease, the method comprising:
administering to a subject diagnosed with diabetes, diabetic enteropathy, or inflammatory bowel disease a therapeutically effective amount of a pharmaceutical composition that comprises an antibody or antigen binding fragment thereof capable of binding to human IGFBP3 and preventing binding of IGFBP3 to transmembrane protein 219 (TMEM219),
wherein the antibody or antigen binding fragment comprises three heavy chain CDRs and three light chain CDRs, and
wherein the six CDRs are:
Yu139-C01: SEQ ID NO:4 (VH CDR1), SEQ ID NO:11 (VH CDR2), SEQ ID NO:20 (VH CDR3), SEQ ID NO:30 (VL CDR1), SEQ ID NO:39 (VL CDR2), and SEQ ID NO:48 (VL CDR3).

9. The method of claim 8, wherein the antibody or antigen binding fragment VH region has the sequence of SEQ ID NO:58 and the VL region has the sequence of SEQ ID NO:69.

10. The method of claim 8, wherein the antibody or antigen-binding fragment thereof is humanized or human.

11. The method of claim 10, wherein the antibody or antigen-binding fragment thereof is a humanized or human IgG2 or IgG4 antibody.

12. The method of claim 8, wherein the disorder is diabetes.

13. The method of claim 12, wherein the disorder is type 1 diabetes.

14. The method of claim 12, wherein the disorder is type 2 diabetes.

15. The method of claim 8, wherein the disorder is diabetic enteropathy.

16. The method of claim 8, wherein the disorder is inflammatory bowel disease.

17. The method of claim 16, wherein the disorder is Crohn's disease.

18. The method of claim 16, wherein the disorder is ulcerative colitis.

19. A method of inhibiting the binding of human IGFBP3 to TMEM219, the method comprising:

contacting human IGFBP3 in vivo with an antibody or antigen-binding fragment thereof comprising three heavy chain CDRs and three light chain CDRs, wherein the six CDRs are:

Yu139-C01: SEQ ID NO:4 (VH CDR1), SEQ ID NO:11 (VH CDR2), SEQ ID NO:20 (VH CDR3), SEQ ID NO:30 (VL CDR1), SEQ ID NO:39 (VL CDR2), and SEQ ID NO:48 (VL CDR3).

20. The method of claim 19, wherein the antibody or antigen binding fragment VH region has the sequence of SEQ ID NO:58 and the VL region has the sequence of SEQ ID NO:69.

21. The method of claim 19, wherein the antibody or antigen-binding fragment thereof is humanized or human.

22. The method of claim 21, wherein the antibody or antigen-binding fragment thereof is a humanized or human IgG2 or IgG4 antibody.

\* \* \* \* \*

SEQUENCE LISTING

```
<160> NUMBER OF SEQ ID NOS: 104

<210> SEQ ID NO 1
<211> LENGTH: 5
<212> TYPE: PRT
<213> ORGANISM: Artificial Sequence
<220> FEATURE:
<223> OTHER INFORMATION: synthetic

<400> SEQUENCE: 1

Ser Tyr Ala Ile Ser
1               5

<210> SEQ ID NO 2
<211> LENGTH: 5
<212> TYPE: PRT
<213> ORGANISM: Artificial Sequence
<220> FEATURE:
<223> OTHER INFORMATION: synthetic

<400> SEQUENCE: 2

Ser Tyr Gly Ile His
1               5

<210> SEQ ID NO 3
<211> LENGTH: 6
<212> TYPE: PRT
<213> ORGANISM: Artificial Sequence
<220> FEATURE:
<223> OTHER INFORMATION: synthetic

<400> SEQUENCE: 3

Ser Ser Asn Trp Trp Ser
1               5

<210> SEQ ID NO 4
<211> LENGTH: 5
<212> TYPE: PRT
<213> ORGANISM: Artificial Sequence
<220> FEATURE:
<223> OTHER INFORMATION: synthetic

<400> SEQUENCE: 4

Ser Tyr Gly Ile Ser
1               5

<210> SEQ ID NO 5
<211> LENGTH: 5
<212> TYPE: PRT
<213> ORGANISM: Artificial Sequence
<220> FEATURE:
<223> OTHER INFORMATION: synthetic

<400> SEQUENCE: 5
```

```
Ser Tyr Gly Met His
1               5

<210> SEQ ID NO 6
<211> LENGTH: 5
<212> TYPE: PRT
<213> ORGANISM: Artificial Sequence
<220> FEATURE:
<223> OTHER INFORMATION: synthetic

<400> SEQUENCE: 6

Asp Tyr Gly Ile Ser
1               5

<210> SEQ ID NO 7
<211> LENGTH: 5
<212> TYPE: PRT
<213> ORGANISM: Artificial Sequence
<220> FEATURE:
<223> OTHER INFORMATION: synthetic

<400> SEQUENCE: 7

Thr Tyr Val Thr Ser
1               5

<210> SEQ ID NO 8
<211> LENGTH: 17
<212> TYPE: PRT
<213> ORGANISM: Artificial Sequence
<220> FEATURE:
<223> OTHER INFORMATION: synthetic

<400> SEQUENCE: 8

Gly Ile Ile Pro Ile Phe Gly Thr Ala Asn Tyr Ala Gln Lys Phe Gln
1               5                   10                  15

Gly

<210> SEQ ID NO 9
<211> LENGTH: 17
<212> TYPE: PRT
<213> ORGANISM: Artificial Sequence
<220> FEATURE:
<223> OTHER INFORMATION: synthetic

<400> SEQUENCE: 9

Ile Val Ser Tyr Asp Gly Arg His Lys Tyr Tyr Ala Asp Ser Val Lys
1               5                   10                  15

Gly

<210> SEQ ID NO 10
<211> LENGTH: 16
<212> TYPE: PRT
<213> ORGANISM: Artificial Sequence
<220> FEATURE:
<223> OTHER INFORMATION: synthetic

<400> SEQUENCE: 10

Glu Val Tyr His Ser Gly Ser Thr Asn Tyr Asn Pro Ser Leu Lys Ser
1               5                   10                  15

<210> SEQ ID NO 11
<211> LENGTH: 17
<212> TYPE: PRT
<213> ORGANISM: Artificial Sequence
<220> FEATURE:
```

```
<223> OTHER INFORMATION: synthetic

<400> SEQUENCE: 11

Trp Ile Asn Thr Tyr Asn Gly Asn Thr Asn Tyr Ala Gln Lys Leu Gln
1               5                   10                  15

Gly

<210> SEQ ID NO 12
<211> LENGTH: 17
<212> TYPE: PRT
<213> ORGANISM: Artificial Sequence
<220> FEATURE:
<223> OTHER INFORMATION: synthetic

<400> SEQUENCE: 12

Trp Ile Ser Ala Tyr Asn Gly Asn Thr Asn Tyr Ala Gln Lys Leu Gln
1               5                   10                  15

Gly

<210> SEQ ID NO 13
<211> LENGTH: 17
<212> TYPE: PRT
<213> ORGANISM: Artificial Sequence
<220> FEATURE:
<223> OTHER INFORMATION: synthetic

<400> SEQUENCE: 13

Val Ile Ser Tyr Asp Gly Ser Asn Lys Tyr Tyr Ala Asp Ser Val Lys
1               5                   10                  15

Gly

<210> SEQ ID NO 14
<211> LENGTH: 17
<212> TYPE: PRT
<213> ORGANISM: Artificial Sequence
<220> FEATURE:
<223> OTHER INFORMATION: synthetic

<400> SEQUENCE: 14

Trp Ile Ser Gly Asp Asn Val Lys Thr Thr Tyr Ala Lys Lys Phe Gln
1               5                   10                  15

Gly

<210> SEQ ID NO 15
<211> LENGTH: 17
<212> TYPE: PRT
<213> ORGANISM: Artificial Sequence
<220> FEATURE:
<223> OTHER INFORMATION: synthetic

<400> SEQUENCE: 15

Trp Ile Ser Ala Tyr Asn Gly Asn Thr Tyr Tyr Ala Gln Lys Leu Gln
1               5                   10                  15

Gly

<210> SEQ ID NO 16
<211> LENGTH: 17
<212> TYPE: PRT
<213> ORGANISM: Artificial Sequence
<220> FEATURE:
<223> OTHER INFORMATION: synthetic

<400> SEQUENCE: 16
```

Gly Ile Ile Pro Met Phe Asp Thr Thr Glu Tyr Ala Gln Lys Leu Glu
1               5                   10                  15

Gly

<210> SEQ ID NO 17
<211> LENGTH: 15
<212> TYPE: PRT
<213> ORGANISM: Artificial Sequence
<220> FEATURE:
<223> OTHER INFORMATION: synthetic

<400> SEQUENCE: 17

Asp Tyr Tyr Asp Ser Ser Gly Tyr Tyr Phe Asp Ala Phe Asp Ile
1               5                   10                  15

<210> SEQ ID NO 18
<211> LENGTH: 13
<212> TYPE: PRT
<213> ORGANISM: Artificial Sequence
<220> FEATURE:
<223> OTHER INFORMATION: synthetic

<400> SEQUENCE: 18

Asp Ser Gly Asn Ser Gly Leu Glu Gly Ile His Asp Tyr
1               5                   10

<210> SEQ ID NO 19
<211> LENGTH: 19
<212> TYPE: PRT
<213> ORGANISM: Artificial Sequence
<220> FEATURE:
<223> OTHER INFORMATION: synthetic

<400> SEQUENCE: 19

Asn Ile Pro Leu Ser Ser Ser Trp Pro Asn Tyr Tyr Tyr Tyr Gly
1               5                   10                  15

Met Asp Val

<210> SEQ ID NO 20
<211> LENGTH: 19
<212> TYPE: PRT
<213> ORGANISM: Artificial Sequence
<220> FEATURE:
<223> OTHER INFORMATION: synthetic

<400> SEQUENCE: 20

Asp Ile Gly Tyr Ser Gly Ser Tyr Tyr Ser Pro Tyr Tyr Tyr Gly
1               5                   10                  15

Met Asp Val

<210> SEQ ID NO 21
<211> LENGTH: 21
<212> TYPE: PRT
<213> ORGANISM: Artificial Sequence
<220> FEATURE:
<223> OTHER INFORMATION: synthetic

<400> SEQUENCE: 21

Val Pro Ser Glu Tyr Tyr Asp Phe Trp Ser Gly Tyr Tyr Thr Glu Glu
1               5                   10                  15

Asn Ala Phe Asp Ile
                20

<210> SEQ ID NO 22

```
<211> LENGTH: 15
<212> TYPE: PRT
<213> ORGANISM: Artificial Sequence
<220> FEATURE:
<223> OTHER INFORMATION: synthetic

<400> SEQUENCE: 22

Asp Asn Gly Asp Tyr Gly Tyr Tyr Tyr Tyr Tyr Met Asp Val
1               5                   10                  15

<210> SEQ ID NO 23
<211> LENGTH: 7
<212> TYPE: PRT
<213> ORGANISM: Artificial Sequence
<220> FEATURE:
<223> OTHER INFORMATION: synthetic

<400> SEQUENCE: 23

Gly Gly Ile Val Phe Asp Tyr
1               5

<210> SEQ ID NO 24
<211> LENGTH: 10
<212> TYPE: PRT
<213> ORGANISM: Artificial Sequence
<220> FEATURE:
<223> OTHER INFORMATION: synthetic

<400> SEQUENCE: 24

Leu Ser Tyr Tyr Asn Tyr Ala Met Asp Val
1               5                   10

<210> SEQ ID NO 25
<211> LENGTH: 9
<212> TYPE: PRT
<213> ORGANISM: Artificial Sequence
<220> FEATURE:
<223> OTHER INFORMATION: synthetic

<400> SEQUENCE: 25

Ala Gly Gly Leu Ser His Phe Asp Tyr
1               5

<210> SEQ ID NO 26
<211> LENGTH: 11
<212> TYPE: PRT
<213> ORGANISM: Artificial Sequence
<220> FEATURE:
<223> OTHER INFORMATION: synthetic

<400> SEQUENCE: 26

Val Lys Trp Glu Leu Gly Trp Ala Phe Asp Ile
1               5                   10

<210> SEQ ID NO 27
<211> LENGTH: 13
<212> TYPE: PRT
<213> ORGANISM: Artificial Sequence
<220> FEATURE:
<223> OTHER INFORMATION: synthetic

<400> SEQUENCE: 27

Ser Gly Ser Ser Ser Asn Ile Gly Thr Asn Thr Val Ser
1               5                   10

<210> SEQ ID NO 28
<211> LENGTH: 11
```

```
<212> TYPE: PRT
<213> ORGANISM: Artificial Sequence
<220> FEATURE:
<223> OTHER INFORMATION: synthetic

<400> SEQUENCE: 28

Arg Ala Ser Gln Gly Ile Ser Ser Trp Leu Ala
1               5                   10

<210> SEQ ID NO 29
<211> LENGTH: 11
<212> TYPE: PRT
<213> ORGANISM: Artificial Sequence
<220> FEATURE:
<223> OTHER INFORMATION: synthetic

<400> SEQUENCE: 29

Gln Gly Asp Ser Leu Arg Asn Tyr Tyr Ala Ser
1               5                   10

<210> SEQ ID NO 30
<211> LENGTH: 11
<212> TYPE: PRT
<213> ORGANISM: Artificial Sequence
<220> FEATURE:
<223> OTHER INFORMATION: synthetic

<400> SEQUENCE: 30

Gln Gly Asp Gly Leu Arg Asn Tyr Phe Ala Ser
1               5                   10

<210> SEQ ID NO 31
<211> LENGTH: 11
<212> TYPE: PRT
<213> ORGANISM: Artificial Sequence
<220> FEATURE:
<223> OTHER INFORMATION: synthetic

<400> SEQUENCE: 31

Arg Ala Ser Gln Ser Ile Ser Ser Tyr Leu Asn
1               5                   10

<210> SEQ ID NO 32
<211> LENGTH: 11
<212> TYPE: PRT
<213> ORGANISM: Artificial Sequence
<220> FEATURE:
<223> OTHER INFORMATION: synthetic

<400> SEQUENCE: 32

Arg Ala Ser Gln Ser Ile Ser Arg Trp Leu Ala
1               5                   10

<210> SEQ ID NO 33
<211> LENGTH: 12
<212> TYPE: PRT
<213> ORGANISM: Artificial Sequence
<220> FEATURE:
<223> OTHER INFORMATION: synthetic

<400> SEQUENCE: 33

Arg Ala Ser Gln Ser Val Ser Gly Asn Tyr Leu Ala
1               5                   10

<210> SEQ ID NO 34
<211> LENGTH: 14
<212> TYPE: PRT
```

```
<213> ORGANISM: Artificial Sequence
<220> FEATURE:
<223> OTHER INFORMATION: synthetic

<400> SEQUENCE: 34

Thr Gly Thr Ser Ser Asp Val Gly Gly Tyr Asn His Val Ser
1               5                   10

<210> SEQ ID NO 35
<211> LENGTH: 16
<212> TYPE: PRT
<213> ORGANISM: Artificial Sequence
<220> FEATURE:
<223> OTHER INFORMATION: synthetic

<400> SEQUENCE: 35

Arg Ser Ser Gln Ser Leu Leu His Ser Asn Gly Asn Asn Tyr Leu Asn
1               5                   10                  15

<210> SEQ ID NO 36
<211> LENGTH: 14
<212> TYPE: PRT
<213> ORGANISM: Artificial Sequence
<220> FEATURE:
<223> OTHER INFORMATION: synthetic

<400> SEQUENCE: 36

Thr Gly Ser Ser Ser Asn Ile Gly Ala Gly Tyr Asp Val His
1               5                   10

<210> SEQ ID NO 37
<211> LENGTH: 7
<212> TYPE: PRT
<213> ORGANISM: Artificial Sequence
<220> FEATURE:
<223> OTHER INFORMATION: synthetic

<400> SEQUENCE: 37

Asn Asn Asn Glu Arg Pro Ser
1               5

<210> SEQ ID NO 38
<211> LENGTH: 7
<212> TYPE: PRT
<213> ORGANISM: Artificial Sequence
<220> FEATURE:
<223> OTHER INFORMATION: synthetic

<400> SEQUENCE: 38

Ala Ala Ser Ser Leu Gln Ser
1               5

<210> SEQ ID NO 39
<211> LENGTH: 7
<212> TYPE: PRT
<213> ORGANISM: Artificial Sequence
<220> FEATURE:
<223> OTHER INFORMATION: synthetic

<400> SEQUENCE: 39

Gly Lys Asn Asn Arg Pro Ser
1               5

<210> SEQ ID NO 40
<211> LENGTH: 7
<212> TYPE: PRT
<213> ORGANISM: Artificial Sequence
```

```
<220> FEATURE:
<223> OTHER INFORMATION: synthetic

<400> SEQUENCE: 40

Asp Ala Ser Ser Leu Glu Ser
1               5

<210> SEQ ID NO 41
<211> LENGTH: 7
<212> TYPE: PRT
<213> ORGANISM: Artificial Sequence
<220> FEATURE:
<223> OTHER INFORMATION: synthetic

<400> SEQUENCE: 41

Gly Ala Ser Ser Arg Ala Thr
1               5

<210> SEQ ID NO 42
<211> LENGTH: 7
<212> TYPE: PRT
<213> ORGANISM: Artificial Sequence
<220> FEATURE:
<223> OTHER INFORMATION: synthetic

<400> SEQUENCE: 42

Glu Val Ser Asn Arg Pro Ser
1               5

<210> SEQ ID NO 43
<211> LENGTH: 7
<212> TYPE: PRT
<213> ORGANISM: Artificial Sequence
<220> FEATURE:
<223> OTHER INFORMATION: synthetic

<400> SEQUENCE: 43

Leu Ser Ser Arg Arg Ala Ser
1               5

<210> SEQ ID NO 44
<211> LENGTH: 7
<212> TYPE: PRT
<213> ORGANISM: Artificial Sequence
<220> FEATURE:
<223> OTHER INFORMATION: synthetic

<400> SEQUENCE: 44

Gly Asn Ser Asn Arg Pro Ser
1               5

<210> SEQ ID NO 45
<211> LENGTH: 11
<212> TYPE: PRT
<213> ORGANISM: Artificial Sequence
<220> FEATURE:
<223> OTHER INFORMATION: synthetic

<400> SEQUENCE: 45

Ala Ala Trp Asp Asp Asn Leu Thr Gly Leu Val
1               5                   10

<210> SEQ ID NO 46
<211> LENGTH: 9
<212> TYPE: PRT
<213> ORGANISM: Artificial Sequence
<220> FEATURE:
```

<223> OTHER INFORMATION: synthetic

<400> SEQUENCE: 46

Gln Gln Ala Asn Ser Phe Pro Leu Thr
1               5

<210> SEQ ID NO 47
<211> LENGTH: 11
<212> TYPE: PRT
<213> ORGANISM: Artificial Sequence
<220> FEATURE:
<223> OTHER INFORMATION: synthetic

<400> SEQUENCE: 47

Asn Ser Arg Asp Ser Ser Ala Lys His Trp Val
1               5                   10

<210> SEQ ID NO 48
<211> LENGTH: 11
<212> TYPE: PRT
<213> ORGANISM: Artificial Sequence
<220> FEATURE:
<223> OTHER INFORMATION: synthetic

<400> SEQUENCE: 48

Asn Ser Arg Asp Gly Ser Gly Lys His Leu Val
1               5                   10

<210> SEQ ID NO 49
<211> LENGTH: 8
<212> TYPE: PRT
<213> ORGANISM: Artificial Sequence
<220> FEATURE:
<223> OTHER INFORMATION: synthetic

<400> SEQUENCE: 49

Gln Gln Ser Tyr Ser Thr Trp Thr
1               5

<210> SEQ ID NO 50
<211> LENGTH: 9
<212> TYPE: PRT
<213> ORGANISM: Artificial Sequence
<220> FEATURE:
<223> OTHER INFORMATION: synthetic

<400> SEQUENCE: 50

Gln Gln Ser Tyr Ser Thr Pro Leu Thr
1               5

<210> SEQ ID NO 51
<211> LENGTH: 9
<212> TYPE: PRT
<213> ORGANISM: Artificial Sequence
<220> FEATURE:
<223> OTHER INFORMATION: synthetic

<400> SEQUENCE: 51

Gln Gln Tyr Gly Ser Ser Pro Gly Thr
1               5

<210> SEQ ID NO 52
<211> LENGTH: 10
<212> TYPE: PRT
<213> ORGANISM: Artificial Sequence
<220> FEATURE:
<223> OTHER INFORMATION: synthetic

```
<400> SEQUENCE: 52

Ser Ser Tyr Thr Ser Ser Asn Thr Trp Val
1               5                   10

<210> SEQ ID NO 53
<211> LENGTH: 9
<212> TYPE: PRT
<213> ORGANISM: Artificial Sequence
<220> FEATURE:
<223> OTHER INFORMATION: synthetic

<400> SEQUENCE: 53

Met Gln Gly Leu Gln Thr Pro Trp Thr
1               5

<210> SEQ ID NO 54
<211> LENGTH: 10
<212> TYPE: PRT
<213> ORGANISM: Artificial Sequence
<220> FEATURE:
<223> OTHER INFORMATION: synthetic

<400> SEQUENCE: 54

Gln Ser Tyr Asp Ser Ser Leu Ser Thr Val
1               5                   10

<210> SEQ ID NO 55
<211> LENGTH: 124
<212> TYPE: PRT
<213> ORGANISM: Artificial Sequence
<220> FEATURE:
<223> OTHER INFORMATION: synthetic

<400> SEQUENCE: 55

Gln Val Gln Leu Val Gln Ser Gly Ala Glu Val Lys Lys Pro Gly Ser
1               5                   10                  15

Ser Val Lys Val Ser Cys Lys Ala Ser Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Glu Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Asp Tyr Tyr Asp Ser Ser Gly Tyr Tyr Phe Asp Ala Phe Asp
            100                 105                 110

Ile Trp Gly Gln Gly Thr Met Val Thr Val Ser Ser
        115                 120

<210> SEQ ID NO 56
<211> LENGTH: 122
<212> TYPE: PRT
<213> ORGANISM: Artificial Sequence
<220> FEATURE:
<223> OTHER INFORMATION: synthetic

<400> SEQUENCE: 56

Gln Val Gln Leu Val Gln Ser Gly Gly Gly Val Val Gln Pro Gly Arg
1               5                   10                  15
```

Ser Leu Arg Leu Ser Cys Ala Ala Ser Gly Phe Thr Phe Ser Ser Tyr
            20                  25                  30

Gly Ile His Trp Val Arg Gln Ala Pro Gly Lys Gly Leu Glu Trp Val
        35                  40                  45

Ala Ile Val Ser Tyr Asp Gly Arg His Lys Tyr Tyr Ala Asp Ser Val
 50                  55                  60

Lys Gly Arg Phe Thr Ile Ser Arg Asp Asp Ser Lys Asn Thr Ile Tyr
 65                  70                  75                  80

Leu Gln Met Asp Ser Leu Arg Ala Glu Asp Thr Ala Val Tyr Tyr Cys
                85                  90                  95

Ala Lys Asp Ser Gly Asn Ser Gly Leu Glu Gly Ile His Asp Tyr Trp
            100                 105                 110

Gly Gln Gly Thr Leu Val Thr Val Ser Ser
        115                 120

<210> SEQ ID NO 57
<211> LENGTH: 128
<212> TYPE: PRT
<213> ORGANISM: Artificial Sequence
<220> FEATURE:
<223> OTHER INFORMATION: synthetic

<400> SEQUENCE: 57

Gln Val Gln Leu Gln Glu Ser Gly Pro Gly Leu Val Lys Pro Ser Gly
 1               5                  10                  15

Thr Leu Ser Leu Thr Cys Ala Val Ser Gly Gly Ser Ile Ser Ser Ser
            20                  25                  30

Asn Trp Trp Ser Trp Val Arg Gln Pro Pro Gly Lys Gly Leu Glu Trp
        35                  40                  45

Ile Gly Glu Val Tyr His Ser Gly Ser Thr Asn Tyr Asn Pro Ser Leu
 50                  55                  60

Lys Ser Arg Val Thr Ile Ser Val Asp Lys Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ala Arg Asn Ile Pro Leu Ser Ser Trp Pro Asn Tyr Tyr Tyr Tyr Tyr
            100                 105                 110

Tyr Gly Met Asp Val Trp Gly Gln Gly Thr Thr Val Thr Val Ser Ser
        115                 120                 125

<210> SEQ ID NO 58
<211> LENGTH: 128
<212> TYPE: PRT
<213> ORGANISM: Artificial Sequence
<220> FEATURE:
<223> OTHER INFORMATION: synthetic

<400> SEQUENCE: 58

Gln Val Gln Leu Val Gln Ser Gly Ala Glu Val Lys Lys Pro Gly Ala
 1               5                  10                  15

Ser Val Lys Val Ser Cys Lys Ala Ser Gly Tyr Thr Phe Thr Ser Tyr
            20                  25                  30

Gly Ile Ser Trp Val Arg Gln Ala Pro Gly Gln Gly Leu Glu Trp Met
        35                  40                  45

Gly Trp Ile Asn Thr Tyr Asn Gly Asn Thr Asn Tyr Ala Gln Lys Leu
 50                  55                  60

Gln Gly Arg Val Thr Met Thr Thr Asp Thr Ser Thr Thr Thr Ala Tyr
 65                  70                  75                  80

Met Glu Leu Arg Ser Leu Arg Ser Asp Asp Thr Ala Val Tyr Tyr Cys
            85                  90                  95

Ala Arg Asp Ile Gly Tyr Ser Gly Ser Tyr Tyr Ser Pro Tyr Tyr Tyr
                100                 105                 110

Tyr Gly Met Asp Val Trp Gly Gln Gly Thr Thr Val Thr Val Ser Ser
        115                 120                 125

<210> SEQ ID NO 59
<211> LENGTH: 130
<212> TYPE: PRT
<213> ORGANISM: Artificial Sequence
<220> FEATURE:
<223> OTHER INFORMATION: synthetic

<400> SEQUENCE: 59

Glu Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
            35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Val Pro Ser Glu Tyr Tyr Asp Phe Trp Ser Gly Tyr Tyr Thr
                100                 105                 110

Glu Glu Asn Ala Phe Asp Ile Trp Gly Gln Gly Thr Met Val Thr Val
            115                 120                 125

Ser Ser
    130

<210> SEQ ID NO 60
<211> LENGTH: 124
<212> TYPE: PRT
<213> ORGANISM: Artificial Sequence
<220> FEATURE:
<223> OTHER INFORMATION: synthetic

<400> SEQUENCE: 60

Glu Val Gln Leu Val Glu Ser Gly Gly Gly Val Val Gln Pro Gly Arg
1               5                   10                  15

Ser Leu Arg Leu Ser Cys Ala Ala Ser Gly Phe Thr Phe Ser Ser Tyr
                20                  25                  30

Gly Met His Trp Val Arg Gln Ala Pro Gly Lys Gly Leu Glu Trp Val
            35                  40                  45

Ala Val Ile Ser Tyr Asp Gly Ser Asn Lys Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Asp Asn Gly Asp Tyr Gly Tyr Tyr Tyr Tyr Tyr Met Asp
                100                 105                 110

Val Trp Gly Lys Gly Thr Thr Val Thr Val Ser Ser

-continued

```
                115                 120

<210> SEQ ID NO 61
<211> LENGTH: 116
<212> TYPE: PRT
<213> ORGANISM: Artificial Sequence
<220> FEATURE:
<223> OTHER INFORMATION: synthetic

<400> SEQUENCE: 61

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Ser Asp Tyr
            20                  25                  30

Gly Ile Ser Trp Val Arg Gln Ala Pro Gly Gln Gly Leu Glu Trp Met
        35                  40                  45

Gly Trp Ile Ser Gly Asp Asn Val Lys Thr Thr Tyr Ala Lys Lys Phe
    50                  55                  60

Gln Gly Arg Val Thr Leu Thr Thr Asp Thr Ser Thr Ser Thr Ala Tyr
65                  70                  75                  80

Met Glu Leu Arg Ser Leu Thr Ser Asp Asp Thr Ala Ala Tyr Tyr Cys
                85                  90                  95

Ala Arg Gly Gly Ile Val Phe Asp Tyr Trp Gly Gln Gly Thr Leu Val
            100                 105                 110

Thr Val Ser Ser
        115

<210> SEQ ID NO 62
<211> LENGTH: 116
<212> TYPE: PRT
<213> ORGANISM: Artificial Sequence
<220> FEATURE:
<223> OTHER INFORMATION: synthetic

<400> SEQUENCE: 62

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
            20                  25                  30

Gly Ile Ser Trp Val Arg Gln Ala Thr Gly Gln Gly Leu Glu Trp Met
        35                  40                  45

Gly Trp Ile Ser Ala Tyr Asn Gly Asn Thr Asn Tyr Ala Gln Lys Leu
    50                  55                  60

Gln Gly Arg Val Thr Met Thr Thr Asp Thr Ser Thr Ser Thr Ala Tyr
65                  70                  75                  80

Met Glu Leu Arg Ser Leu Arg Ser Asp Asp Thr Ala Val Tyr Tyr Cys
                85                  90                  95

Ala Arg Gly Gly Ile Val Phe Asp Tyr Trp Gly Gln Gly Thr Leu Val
            100                 105                 110

Thr Val Ser Ser
        115

<210> SEQ ID NO 63
<211> LENGTH: 119
<212> TYPE: PRT
<213> ORGANISM: Artificial Sequence
<220> FEATURE:
<223> OTHER INFORMATION: synthetic

<400> SEQUENCE: 63
```

Gln Met Gln Leu Val Gln Ser Gly Ala Glu Val Lys Met Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Tyr Tyr Ala Gln Lys Leu
    50                  55                  60

Gln Gly Arg Val Thr Met Thr Ala Asp Thr Ser Thr Ser Thr Ala Tyr
65                  70                  75                  80

Met Asp Leu Arg Ser Leu Arg Ser Asp Asp Thr Ala Val Tyr Tyr Cys
                85                  90                  95

Ala Arg Leu Ser Tyr Tyr Asn Tyr Ala Met Asp Val Trp Gly Gln Gly
                100                 105                 110

Thr Thr Val Thr Val Ser Ser
            115

<210> SEQ ID NO 64
<211> LENGTH: 118
<212> TYPE: PRT
<213> ORGANISM: Artificial Sequence
<220> FEATURE:
<223> OTHER INFORMATION: synthetic

<400> SEQUENCE: 64

Gln Val Gln Leu Gln Gln Ser Gly Ala Glu Val Lys Lys Pro Gly Ser
1               5                   10                  15

Ser Val Lys Val Ser Cys Lys Ala Ser Gly Gly Ile Phe Ser Thr Tyr
                20                  25                  30

Val Thr Ser Trp Val Arg Gln Ala Pro Gly Gln Gly Leu Glu Trp Met
        35                  40                  45

Gly Gly Ile Ile Pro Met Phe Asp Thr Thr Glu Tyr Ala Gln Lys Leu
    50                  55                  60

Glu Gly Arg Val Thr Ile Thr Val Asp Glu Ser Thr Asn Thr Ala Tyr
65                  70                  75                  80

Met Glu Leu Ser Ser Leu Arg Phe Glu Asp Thr Ala Val Tyr Tyr Cys
                85                  90                  95

Ala Arg Ala Gly Gly Leu Ser His Phe Asp Tyr Trp Gly Gln Gly Thr
                100                 105                 110

Leu Val Thr Val Ser Ser
            115

<210> SEQ ID NO 65
<211> LENGTH: 120
<212> TYPE: PRT
<213> ORGANISM: Artificial Sequence
<220> FEATURE:
<223> OTHER INFORMATION: synthetic

<400> SEQUENCE: 65

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Ser Tyr
                20                  25                  30

Gly Ile Ser Trp Val Arg Gln Ala Pro Gly Gln Gly Leu Glu Trp Met
        35                  40                  45

Gly Trp Ile Ser Ala Tyr Asn Gly Asn Thr Asn Tyr Ala Gln Lys Leu

```
                    50                  55                  60
Gln Gly Arg Val Thr Met Thr Thr Asp Thr Ser Thr Ser Thr Ala Tyr
 65                  70                  75                  80

Met Glu Leu Arg Ser Leu Arg Ser Asp Asp Thr Ala Val Tyr Tyr Cys
                     85                  90                  95

Ala Arg Val Lys Trp Glu Leu Gly Trp Ala Phe Asp Ile Trp Gly Gln
                100                 105                 110

Gly Thr Met Val Thr Val Ser Ser
            115                 120

<210> SEQ ID NO 66
<211> LENGTH: 110
<212> TYPE: PRT
<213> ORGANISM: Artificial Sequence
<220> FEATURE:
<223> OTHER INFORMATION: synthetic

<400> SEQUENCE: 66

Gln Ala Gly Leu Thr Gln Pro Pro Ser Ala Ser Gly Thr Pro Gly Gln
 1               5                  10                  15

Arg Val Ile Ile Ser Cys Ser Gly Ser Ser Ser Asn Ile Gly Thr Asn
                20                  25                  30

Thr Val Ser Trp Tyr Gln His Leu Pro Gly Thr Ala Pro Lys Leu Leu
            35                  40                  45

Ile Tyr Asn Asn Asn Glu Arg Pro Ser Gly Val Pro Arg Arg Phe Ser
        50                  55                  60

Gly Ser Arg Ser Gly Ala Ser Ala Ser Leu Ala Ile Ser Gly Leu Gln
 65                  70                  75                  80

Ser Asp Asp Glu Ala His Tyr Tyr Cys Ala Ala Trp Asp Asp Asn Leu
                 85                  90                  95

Thr Gly Leu Val Phe Gly Gly Gly Thr Lys Leu Thr Val Leu
            100                 105                 110

<210> SEQ ID NO 67
<211> LENGTH: 107
<212> TYPE: PRT
<213> ORGANISM: Artificial Sequence
<220> FEATURE:
<223> OTHER INFORMATION: synthetic

<400> SEQUENCE: 67

Asp Val Val Met Thr Gln Ser Pro Ser Ser Val Ser Ala Ser Val Gly
 1               5                  10                  15

Asp Arg Val Thr Ile Thr Cys Arg Ala Ser Gln Gly Ile Ser Ser Trp
                20                  25                  30

Leu Ala Trp Tyr Gln Gln Lys Pro Gly Lys Ala Pro Lys Leu Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Asp Phe Thr Leu Thr Ile Ser Ser Leu Gln Pro
 65                  70                  75                  80

Glu Asp Phe Gly Thr Tyr Tyr Cys Gln Gln Ala Asn Ser Phe Pro Leu
                 85                  90                  95

Thr Phe Gly Gly Gly Thr Lys Val Glu Ile Lys
            100                 105

<210> SEQ ID NO 68
<211> LENGTH: 107
```

```
<212> TYPE: PRT
<213> ORGANISM: Artificial Sequence
<220> FEATURE:
<223> OTHER INFORMATION: synthetic

<400> SEQUENCE: 68

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Asn Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Asn Gly Ala Gln Ala Glu
65                  70                  75                  80

Asp Glu Ala Asp Tyr Tyr Cys Asn Ser Arg Asp Ser Ser Ala Lys His
                85                  90                  95

Trp Val Phe Gly Gly Gly Thr Lys Leu Thr Val
            100                 105

<210> SEQ ID NO 69
<211> LENGTH: 107
<212> TYPE: PRT
<213> ORGANISM: Artificial Sequence
<220> FEATURE:
<223> OTHER INFORMATION: synthetic

<400> SEQUENCE: 69

Ser Ser Glu Leu Thr Gln Asp Pro Ala Val Ser Val Ala Leu Gly Gln
1               5                   10                  15

Thr Val Arg Ile Thr Cys Gln Gly Asp Gly Leu Arg Asn Tyr Phe Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Arg Ile Ala Gly Ala Gln Ala Glu
65                  70                  75                  80

Asp Glu Ala Asp Tyr Tyr Cys Asn Ser Arg Asp Gly Ser Gly Lys His
                85                  90                  95

Leu Val Phe Gly Gly Gly Thr Lys Leu Thr Val
            100                 105

<210> SEQ ID NO 70
<211> LENGTH: 106
<212> TYPE: PRT
<213> ORGANISM: Artificial Sequence
<220> FEATURE:
<223> OTHER INFORMATION: synthetic

<400> SEQUENCE: 70

Asp Ile Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
```

```
                    50                  55                  60
Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ser Thr Trp Thr
                    85                  90                  95

Phe Gly Gln Gly Thr Lys Val Glu Ile Lys
                100                 105

<210> SEQ ID NO 71
<211> LENGTH: 107
<212> TYPE: PRT
<213> ORGANISM: Artificial Sequence
<220> FEATURE:
<223> OTHER INFORMATION: synthetic

<400> SEQUENCE: 71

Asp Ile Gln Met Thr Gln Ser Pro Ser Thr Leu Ser Ala Ser Val Gly
 1                   5                  10                  15

Asp Arg Val Thr Ile Thr Cys Arg Ala Ser Gln Ser Ile Ser Arg Trp
                    20                  25                  30

Leu Ala Trp Tyr Gln Gln Lys Pro Gly Lys Ala Pro Lys Leu Leu Ile
                    35                  40                  45

Tyr Asp Ala Ser Ser Leu Glu Ser Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Ser Tyr Ser Thr Pro Leu
                    85                  90                  95

Thr Phe Gly Pro Gly Thr Lys Val Asp Ile Lys
                100                 105

<210> SEQ ID NO 72
<211> LENGTH: 108
<212> TYPE: PRT
<213> ORGANISM: Artificial Sequence
<220> FEATURE:
<223> OTHER INFORMATION: synthetic

<400> SEQUENCE: 72

Glu Thr Thr Leu Thr Gln Ser Pro Gly Thr Leu Ser Leu Ser Pro Gly
 1                   5                  10                  15

Glu Arg Ala Thr Leu Ser Cys Arg Ala Ser Gln Ser Val Ser Gly Asn
                    20                  25                  30

Tyr Leu Ala Trp Tyr Gln Gln Lys Pro Gly Gln Pro Pro Arg Leu Leu
                    35                  40                  45

Ile Phe Gly Ala Ser Ser Arg Ala Thr Gly Ile Pro Asp Arg Phe Ser
         50                  55                  60

Gly Ser Gly Ser Gly Thr Asp Phe Thr Leu Thr Ile Ser Arg Leu Glu
 65                  70                  75                  80

Pro Glu Asp Phe Gly Val Tyr Tyr Cys Gln Gln Tyr Gly Ser Ser Pro
                    85                  90                  95

Gly Thr Phe Gly Gln Gly Thr Lys Val Glu Ile Lys
                100                 105

<210> SEQ ID NO 73
<211> LENGTH: 107
<212> TYPE: PRT
<213> ORGANISM: Artificial Sequence
<220> FEATURE:
```

<223> OTHER INFORMATION: synthetic

<400> SEQUENCE: 73

```
Asp Val Val Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Asn Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Ser Thr Pro Leu
                85                  90                  95

Thr Phe Gly Gly Gly Thr Lys Val Glu Ile Lys
            100                 105
```

<210> SEQ ID NO 74
<211> LENGTH: 110
<212> TYPE: PRT
<213> ORGANISM: Artificial Sequence
<220> FEATURE:
<223> OTHER INFORMATION: synthetic

<400> SEQUENCE: 74

```
Gln Ser Ala Leu Thr Gln Pro Pro Ser Ala Ser Gly Ser Pro Gly Gln
1               5                   10                  15

Ser Val Thr Ile Ser Cys Thr Gly Thr Ser Ser Asp Val Gly Gly Tyr
            20                  25                  30

Asn His Val Ser Trp Tyr Gln Gln His Pro Gly Lys Ala Pro Lys Leu
        35                  40                  45

Met Ile Tyr Glu Val Ser Asn Arg Pro Ser Gly Val Pro Asn Arg Phe
50                  55                  60

Ser Gly Ser Lys Ser Gly Asn Thr Ala Ser Leu Thr Ile Ser Gly Leu
65                  70                  75                  80

Gln Ala Glu Asp Glu Ala Asp Tyr Tyr Cys Ser Ser Tyr Thr Ser Ser
                85                  90                  95

Asn Thr Trp Val Phe Gly Gly Gly Thr Lys Leu Thr Val Leu
            100                 105                 110
```

<210> SEQ ID NO 75
<211> LENGTH: 112
<212> TYPE: PRT
<213> ORGANISM: Artificial Sequence
<220> FEATURE:
<223> OTHER INFORMATION: synthetic

<400> SEQUENCE: 75

```
Glu Ile Val Leu Thr Gln Ser Pro Leu Ser Leu Pro Val Thr Pro Gly
1               5                   10                  15

Glu Pro Ala Ser Ile Ser Cys Arg Ser Ser Gln Ser Leu Leu His Ser
            20                  25                  30

Asn Gly Asn Asn Tyr Leu Asn Trp Tyr Leu Gln Lys Pro Gly Gln Ser
        35                  40                  45

Pro Gln Leu Leu Ile Tyr Leu Ser Ser Arg Arg Ala Ser Gly Val Pro
50                  55                  60

Asp Arg Phe Ser Gly Ser Gly Ser Gly Thr Asp Phe Thr Leu Lys Ile
```

```
                65                  70                  75                  80
Ser Arg Val Glu Ala Glu Asp Val Gly Val Tyr Tyr Cys Met Gln Gly
                    85                  90                  95

Leu Gln Thr Pro Trp Thr Phe Gly Gln Gly Thr Lys Val Glu Thr Lys
                100                 105                 110

<210> SEQ ID NO 76
<211> LENGTH: 110
<212> TYPE: PRT
<213> ORGANISM: Artificial Sequence
<220> FEATURE:
<223> OTHER INFORMATION: synthetic

<400> SEQUENCE: 76

Gln Ala Val Leu Thr Gln Pro Pro Ser Val Ser Gly Ala Pro Gly Gln
1               5                   10                  15

Arg Val Thr Ile Ser Cys Thr Gly Ser Ser Ser Asn Ile Gly Ala Gly
                20                  25                  30

Tyr Asp Val His Trp Tyr Gln Gln Leu Pro Gly Thr Ala Pro Lys Leu
            35                  40                  45

Leu Ile Tyr Gly Asn Ser Asn Arg Pro Ser Gly Val Pro Asp Arg Phe
        50                  55                  60

Ser Gly Ser Lys Ser Gly Thr Ser Ala Pro Leu Ala Ile Thr Gly Leu
65                  70                  75                  80

Gln Ala Glu Asp Glu Ala Asp Tyr Tyr Cys Gln Ser Tyr Asp Ser Ser
                85                  90                  95

Leu Ser Thr Val Phe Gly Gly Gly Thr Lys Leu Thr Val Leu
                100                 105                 110

<210> SEQ ID NO 77
<211> LENGTH: 372
<212> TYPE: DNA
<213> ORGANISM: Artificial Sequence
<220> FEATURE:
<223> OTHER INFORMATION: synthetic

<400> SEQUENCE: 77
caggttcagc tggtgcagtc tggggctgag gtgaagaagc ctgggtcctc ggtgaaggtc        60
tcctgcaagg cttctggagg caccttcagc agctatgcta tcagctgggt gcgacaggcc       120
cctggacaag gcttgagtg gatgggaggg atcatcccta tctttggtac agcaaactac       180
gcacagaagt tccagggcag agtcacgatt accgcggacg aatccacgag cacagcctac       240
atggagctga gcagcctgag atctgaggac acggccgtgt attactgtgc gagagattac       300
tatgatagta gtggttatta ctttgatgct tttgatatct ggggccaagg gacaatggtc       360
accgtctctt ca                                                           372

<210> SEQ ID NO 78
<211> LENGTH: 366
<212> TYPE: DNA
<213> ORGANISM: Artificial Sequence
<220> FEATURE:
<223> OTHER INFORMATION: synthetic

<400> SEQUENCE: 78
caggtccagc tggtacaatc tggggaggc gtggtccagc tgggaggtc cctgagactc         60 tcctgtgcag cctctggatt caccttcagt agctatggca tccactgggt ccgccaggct       120
ccaggcaagg ggctggagtg gtggcaatt gtatcatatg atggaagaca taaatattat       180
```

```
gcagactccg tgaagggccg attcaccatc tccagagacg attccaagaa cacgatctat    240
ctgcaaatgg acagcctgag agctgaggac acggctgtat attactgtgc gaaagatagt    300
gggaactccg gtctggaagg tatccatgac tactggggcc agggaaccct ggtcaccgtc    360
tcctca                                                                366
```

<210> SEQ ID NO 79
<211> LENGTH: 384
<212> TYPE: DNA
<213> ORGANISM: Artificial Sequence
<220> FEATURE:
<223> OTHER INFORMATION: synthetic

<400> SEQUENCE: 79

```
caggtgcagc tgcaggagtc gggcccagga ctggtgaagc cttcggggac cctgtccctc     60
acctgcgctg tctctggtgg ctccatcagc agtagtaact ggtggagttg ggtccgccag    120
cccccaggga aggggctgga gtggattggg aagtctatc atagtgggag caccaactac     180
aacccgtccc tcaagagtcg agtcaccata tcagtagaca agtccaagaa ccagttctcc    240
ctgaagctga gctctgtgac cgccgcggac acggccgtgt attactgtgc gagaaacatc    300 cccttagca gcagctggcc taattactac tactactacg gtatggacgt ctggggccaa    360
gggaccacgg tcaccgtctc ctca                                           384
```

<210> SEQ ID NO 80
<211> LENGTH: 384
<212> TYPE: DNA
<213> ORGANISM: Artificial Sequence
<220> FEATURE:
<223> OTHER INFORMATION: synthetic

<400> SEQUENCE: 80

```
caggtccagc tggtgcaatc tggagctgag gtgaagaagc ctggggcctc agtgaaggtc     60
tcctgcaagg cttctggcta cacctttacc agctatggta tcagctgggt gcgacaggcc    120
cctggacaag gcttgagtg gatgggatgg atcaacactt acaatggtaa cacaaactat    180
gcacagaaac tccagggcag agtcaccatg accacagaca catccacgac cacagcctac    240
atggagctga ggagcctgag atctgacgac acggccgtat attactgtgc gagagatatc    300
gggtatagtg ggagctacta ttcgccctac tactactacg gtatggacgt ctggggccaa    360
gggaccacgg tcaccgtctc ctca                                           384
```

<210> SEQ ID NO 81
<211> LENGTH: 390
<212> TYPE: DNA
<213> ORGANISM: Artificial Sequence
<220> FEATURE:
<223> OTHER INFORMATION: synthetic

<400> SEQUENCE: 81

```
gaggtgcagc tggtgcagtc tggggctgag gtgaagaagc ctggggcttc agtgaaggtc     60
tcctgcaagg cttctggtta cacctttacc agctatggta tcagctgggt gcgacaggcc    120
cctggacaag gcttgagtg gatgggatgg atcagcgctt acaatggtaa cacaaactat    180
gcacagaagc tccagggcag agtcaccatg accacagaca catccacgag cacagcctac    240
atggagctga ggagcctgag atctgacgac acggctgtgt attactgtgc gagagttccc    300
tcagagtatt acgattttg gagtggttat tataccgaag agaatgcttt tgatatctgg    360
ggccaaggga caatggtcac cgtctcttca                                     390
```

<210> SEQ ID NO 82
<211> LENGTH: 372
<212> TYPE: DNA
<213> ORGANISM: Artificial Sequence
<220> FEATURE:
<223> OTHER INFORMATION: synthetic

<400> SEQUENCE: 82

```
gaggtgcagc tggtggagtc tgggggaggc gtggtccagc ctggggaggtc cctgagactc      60 tcctgtgcag cctctggatt caccttcagt agctatggca tgcactgggt ccgccaggct     120
ccaggcaagg ggctggagtg ggtggcagtt atatcatatg atggaagtaa taaatactat     180
gcagactccg tgaagggccg attcaccatc tccagagaca attccaagaa cacgctgtat     240
ctgcaaatga acagcctgag agctgaggac acggctgtgt attactgtgc gaaagataac     300
ggtgactacg gatactacta ctactactac atggacgtct ggggcaaagg gaccacggtc     360
accgtctcct ca                                                         372
```

<210> SEQ ID NO 83
<211> LENGTH: 348
<212> TYPE: DNA
<213> ORGANISM: Artificial Sequence
<220> FEATURE:
<223> OTHER INFORMATION: synthetic

<400> SEQUENCE: 83

```
caggtgcagc tggtgcagtc tggagctgag gtgaagaagc ctgggggcctc agtgaaggtc      60 tcctgcaagg cttctggtta caccttttcc gactatggta tcagctgggt gcgacaggcc     120
cctggacaag ggcttgagtg gatgggatgg atcagcggtg acaatgttaa gactacctat     180
gcaaagaagt tccagggcag agtcaccctg accacagaca catccacgag cacagcctac     240
atggagctga ggagcctgac atctgacgac acggccgcat attactgtgc gagaggggggg     300 atcgtatttg actactgggg ccagggaacc ctggtcaccg tctcctca                  348
```

<210> SEQ ID NO 84
<211> LENGTH: 348
<212> TYPE: DNA
<213> ORGANISM: Artificial Sequence
<220> FEATURE:
<223> OTHER INFORMATION: synthetic

<400> SEQUENCE: 84

```
caggttcagc tggtgcagtc tggggctgag gtgaagaagc ctggggcctc agtgaaggtc       60
tcctgcaagg cttctggtta cacctttacc agctatggta tcagctgggt gcgacaggcc     120
actggacaag ggcttgagtg gatgggatgg atcagcgctt acaatggtaa cacaaactat     180
gcacagaagc tccagggcag agtcaccatg accacagaca catccacgag cacagcctac     240
atggagctga ggagcctgag atctgacgac acggccgtgt attactgtgc gagaggggggg     300 atcgtatttg actactgggg ccagggaacc ctggtcaccg tctcctca                  348
```

<210> SEQ ID NO 85
<211> LENGTH: 357
<212> TYPE: DNA
<213> ORGANISM: Artificial Sequence
<220> FEATURE:
<223> OTHER INFORMATION: synthetic

<400> SEQUENCE: 85

```
caaatgcagc tggtacagtc tggggctgag gtgaagatgc tggggcctc agtgaaggtc      60 tcctgcaagg cttctggtta caccttacc agctatggta tcagctgggt gcgacaggcc     120
cctggacaag ggcttgagtg gatggggtgg atcagcgctt acaatggtaa cacatactat    180
gcacagaaac tccagggcag agtcaccatg accgcagaca catccacgag cacagcctac    240
atggacctga ggagcctgag atctgacgac acggccgtgt attactgtgc gagactatca    300 tattcaact acgctatgga cgtctggggc caagggacca cggtcaccgt ctcctca        357
```

```
<210> SEQ ID NO 86
<211> LENGTH: 354
<212> TYPE: DNA
<213> ORGANISM: Artificial Sequence
<220> FEATURE:
<223> OTHER INFORMATION: synthetic

<400> SEQUENCE: 86
caggtacagc tgcagcagtc aggggctgag gtgaagaagc tgggtcctc ggtgaaggtg      60 tcctgcaagg cttctggagg catcttcagc acctatgtga ccagctgggt gcgacaggcc    120
cctggacaag ggcttgagtg gatgggaggg atcatcccta tgtttgacac aacagagtac    180
gcacagaagc tcgagggcag agtcacgatc accgtgacg aatccacgaa cacagcctac    240
atggagctga gcagcctgag atttgaggac acggccgtat attactgtgc gagagcggga    300
ggtttgagcc actttgacta ctggggccag ggaactctgg tcaccgtctc gtca           354
```

```
<210> SEQ ID NO 87
<211> LENGTH: 360
<212> TYPE: DNA
<213> ORGANISM: Artificial Sequence
<220> FEATURE:
<223> OTHER INFORMATION: synthetic

<400> SEQUENCE: 87
caggtccagc tggtacagtc tggagctgag gtgaagaagc tggggcctc agtgaaggtc      60 tcctgcaagg cttctggtta caccttacc agctatggta tcagctgggt gcgacaggcc    120
cctggacaag ggcttgagtg gatgggatgg atcagcgctt acaatggtaa cacaaactat    180
gcacagaagc tccagggcag agtcaccatg accacagaca catccacaag cacagcctac    240
atggagctga ggagcctgag atctgacgac acggccgtgt attactgtgc gagagtgaag    300
tgggagctag ggtgggcttt tgatatctgg ggccaaggga caatggtcac cgtctcttca    360
```

```
<210> SEQ ID NO 88
<211> LENGTH: 330
<212> TYPE: DNA
<213> ORGANISM: Artificial Sequence
<220> FEATURE:
<223> OTHER INFORMATION: synthetic

<400> SEQUENCE: 88
caggctgggc tgactcagcc accctcagcg tctgggaccc ccgggcagag ggtcatcatc      60
tcttgttctg gaagcagctc caacatcgga actaatactg taagctggta tcaacacctc     120
ccaggaacgg ccccccaagct cctcatctat aacaataatg aacggccctc agggtccct    180 cgccgattct ctggctccag gtctggcgcc tcagcctccc tggccatcag tgggctccag    240
tctgacgatg aggctcatta ttattgtgca gcctgggatg acaacctgac tggcttggtg    300
ttcggcggag ggaccaaact gaccgtccta                                      330
```

```
<210> SEQ ID NO 89
<211> LENGTH: 321
<212> TYPE: DNA
<213> ORGANISM: Artificial Sequence
<220> FEATURE:
<223> OTHER INFORMATION: synthetic

<400> SEQUENCE: 89
gatgttgtga tgactcagtc tccttcttcc gtgtctgcat ctgtaggaga cagagtcacc    60
atcacttgtc gggcgagtca gggtattagc agctggttag cctggtatca gcagaaacca   120
gggaaagccc ctaagctcct gatctatgct gcatccagtt tgcaaagtgg ggtcccatca   180
aggttcagcg gcagtggatc tgggacagat ttcacactca ccatcagcag cctgcagcct   240
gaagattttg aacttacta ttgtcaacag gctaacagtt ttccgctcac tttcggcgga   300
gggaccaagg tggagatcaa a                                             321

<210> SEQ ID NO 90
<211> LENGTH: 321
<212> TYPE: DNA
<213> ORGANISM: Artificial Sequence
<220> FEATURE:
<223> OTHER INFORMATION: synthetic

<400> SEQUENCE: 90
tcttctgagc tgactcagga ccctgctgtg tctgtggcct tgggacagac agtcaggatc    60
acatgccaag agacagcct cagaaactat tatgcaagct ggtaccagca gaagccagga   120
caggcccctg tacttgtcat ctatggtaaa aacaaccggc cctcaggat cccagaccga   180 ttctctggct ccagctcagg aaacacagct tccttgacca tcaatggggc tcaggcggaa   240
gatgaggctg actattactg taactcccgg gacagcagtg ctaaacattg ggtgttcggc   300
ggagggacca agctgaccgt c                                             321

<210> SEQ ID NO 91
<211> LENGTH: 321
<212> TYPE: DNA
<213> ORGANISM: Artificial Sequence
<220> FEATURE:
<223> OTHER INFORMATION: synthetic

<400> SEQUENCE: 91
tcttctgagc tgactcagga ccctgctgtg tctgtggcct tgggacagac agtcaggatc    60
acgtgccaag agacggcct cagaaactat tttgcaagtt ggtaccagca gaagccagga   120
caggcccctg tacttgtcat ctatggtaaa aacaaccggc cctcaggat cccagaccga   180 ttctctggct ccagctcagg aaacacagct tccttgagaa tcgctggggc tcaggcggaa   240
gatgaggctg actattactg taattcccgg gacggcagtg taagcatct ggtattcggc   300 ggagggacca agttgaccgt c                                             321

<210> SEQ ID NO 92
<211> LENGTH: 318
<212> TYPE: DNA
<213> ORGANISM: Artificial Sequence
<220> FEATURE:
<223> OTHER INFORMATION: synthetic

<400> SEQUENCE: 92
gacatcgtga tgacccagtc tccatcctcc ctgtctgcat ctgtaggaga cagagtcacc    60
atcacttgcc gggcaagtca gagcattagc agctatttaa attggtatca gcagaaacca   120
```

```
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta cctggacgtt cggccaaggg    300
accaaggtgg aaatcaaa                                                   318
```

<210> SEQ ID NO 93
<211> LENGTH: 321
<212> TYPE: DNA
<213> ORGANISM: Artificial Sequence
<220> FEATURE:
<223> OTHER INFORMATION: synthetic

<400> SEQUENCE: 93

```
gacatccaga tgactcagtc tccttccacc ctgtctgcat ctgtaggaga cagagtcacc     60
atcacttgcc gggccagtca gagtattagt aggtggttgg cctggtatca gcagaaacca    120
gggaaagccc ctaagctcct gatctatgat gcctccagtt tggaaagtgg ggtcccatca    180
aggttcagcg gcagtggatc tgggacagaa ttcactctca ccatcagcag cctgcagcct    240
gatgattttg caacttatta ctgtcaacag agttacagta cccctcttac tttcggccct    300
gggaccaaag tggatatcaa a                                              321
```

<210> SEQ ID NO 94
<211> LENGTH: 324
<212> TYPE: DNA
<213> ORGANISM: Artificial Sequence
<220> FEATURE:
<223> OTHER INFORMATION: synthetic

<400> SEQUENCE: 94

```
gaaacgacac tcacgcagtc tccaggcacc ctgtctttgt ctccagggga aagagccacc     60
ctctcctgca gggccagtca gagtgttagt ggcaactact tagcctggta ccagcagaaa    120
cctggccagc ctcccaggct cctcatcttt ggtgcatcca gcagggccac tggcatccca    180
gacaggttca gtggcagtgg gtctgggaca gacttcactc tcaccatcag cagactggag    240
cctgaagatt ttggagtgta ttactgtcag cagtatggta gctcaccagg gacgttcggc    300
caagggacca aggtggaaat caaa                                           324
```

<210> SEQ ID NO 95
<211> LENGTH: 321
<212> TYPE: DNA
<213> ORGANISM: Artificial Sequence
<220> FEATURE:
<223> OTHER INFORMATION: synthetic

<400> SEQUENCE: 95

```
gatgttgtga tgactcagtc tccatcctcc ctgtctgcat ctgtaggaga cagagtcacc     60
atcacttgcc gggcaagtca gagcattagc agctatttaa attggtatca gcagaaacca    120
gggaaagccc ctaagctcct gatctatgct gcatccagtt tgcaaagtgg ggtcccatca    180
aggttcagtg gcagtggatc tgggacagat ttcactctca ccatcagcag tctgcaacct    240
gaagattttg caacttacta ctgtcaacag agttacagta ccccgctcac tttcggcgga    300
gggaccaagg tggagatcaa a                                              321
```

<210> SEQ ID NO 96
<211> LENGTH: 330
<212> TYPE: DNA
<213> ORGANISM: Artificial Sequence
<220> FEATURE:
<223> OTHER INFORMATION: synthetic

<400> SEQUENCE: 96

```
cagtctgccc tgactcagcc tccctccgcg tccgggtccc ctggacagtc agtcaccatc    60
tcctgcactg gaaccagcag tgatgttggt ggttataacc atgtctcctg gtaccagcaa   120
cacccaggca aagcccccaa actcatgatt tatgaggtca gtaatcggcc ctcaggagtt   180
cctaatcgct tctctggctc caagtctggc aacacggcct ccctgaccat ctctgggctc   240
caggctgagg acgaggctga ttattactgc agctcatata caagcagcaa cacttgggtg   300
ttcggcggag ggaccaagct gaccgtccta                                    330
```

<210> SEQ ID NO 97
<211> LENGTH: 336
<212> TYPE: DNA
<213> ORGANISM: Artificial Sequence
<220> FEATURE:
<223> OTHER INFORMATION: synthetic

<400> SEQUENCE: 97

```
gaaattgtgc tgactcagtc tccactctcc ctgcccgtca cccctggaga gccggcctcc    60
atctcctgca ggtctagtca gagcctcctg catagtaatg gaaacaacta tttgaattgg   120
tacctgcaga agccagggca gtctccacag ctcctgatct atttgagttc tcgtcgggcc   180
tccggggtcc ctgacaggtt cagtggcagt ggatcaggca cagatttac actgaaaatt    240
agcagagtgg aggctgagga tgttggggtt tattactgca tgcaaggtct acaaactccg   300
tggacgttcg gccaagggac caaggtggaa accaaa                             336
```

<210> SEQ ID NO 98
<211> LENGTH: 330
<212> TYPE: DNA
<213> ORGANISM: Artificial Sequence
<220> FEATURE:
<223> OTHER INFORMATION: synthetic

<400> SEQUENCE: 98

```
caggcagtgc tgactcagcc accctcagtg tctggggccc cagggcagag ggtcaccatc    60
tcctgcactg ggagcagctc caacatcggg gcaggttatg atgtacactg gtaccagcag   120
cttccaggaa cagcccccaa actcctcatc tatggtaaca gcaatcggcc ctcaggggtc   180
cctgaccgat tctctggctc caagtctggc acctcagccc ccctggccat cactgggctc   240
caggctgagg acgaggctga ttattactgc cagtcttatg acagcagcct gagtacggta   300
ttcggcggag ggaccaagct gaccgtccta                                    330
```

<210> SEQ ID NO 99
<211> LENGTH: 327
<212> TYPE: PRT
<213> ORGANISM: Artificial Sequence
<220> FEATURE:
<223> OTHER INFORMATION: synthetic

<400> SEQUENCE: 99

```
Ala Ser Thr Lys Gly Pro Ser Val Phe Pro Leu Ala Pro Cys Ser Arg
 1               5                  10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45
```

Gly Val His Thr Phe Pro Ala Val Leu Gln Ser Ser Gly Leu Tyr Ser
            50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Ser Cys Pro Ala Pro
            100                 105                 110

Glu Phe Leu Gly Gly Pro Ser Val Phe Leu Phe Pro Pro Lys Pro Lys
            115                 120                 125

Asp Thr Leu Met Ile Ser Arg Thr Pro Glu Val Thr Cys Val Val Val
            130                 135                 140

Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
            180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
            260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Ser Leu Ser Leu Gly Lys
                325

<210> SEQ ID NO 100
<211> LENGTH: 326
<212> TYPE: PRT
<213> ORGANISM: Artificial Sequence
<220> FEATURE:
<223> OTHER INFORMATION: synthetic

<400> SEQUENCE: 100

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
            35                  40                  45

Gly Val His Thr Phe Pro Ala Val Leu Gln Ser Ser Gly Leu Tyr Ser
            50                  55                  60

Leu Ser Ser Val Val Thr Val Pro Ser Ser Asn Phe Gly Thr Gln Thr
65                  70                  75                  80

Tyr Thr Cys Asn Val Asp His Lys Pro Ser Asn Thr Lys Val Asp Lys
                85                  90                  95

Thr Val Glu Arg Lys Cys Cys Val Glu Cys Pro Pro Cys Pro Ala Pro
            100                 105                 110

Pro Val Ala Gly Pro Ser Val Phe Leu Phe Pro Pro Lys Pro Lys Asp
            115                 120                 125

Thr Leu Met Ile Ser Arg Thr Pro Glu Val Thr Cys Val Val Val Asp
        130                 135                 140

Val Ser His Glu Asp Pro Glu Val Gln Phe Asn Trp Tyr Val Asp Gly
145                 150                 155                 160

Val Glu Val His Asn Ala Lys Thr Lys Pro Arg Glu Glu Gln Phe Asn
                165                 170                 175

Ser Thr Phe Arg Val Val Ser Val Leu Thr Val Val His Gln Asp Trp
            180                 185                 190

Leu Asn Gly Lys Glu Tyr Lys Cys Lys Val Ser Asn Lys Gly Leu Pro
        195                 200                 205

Ala Pro Ile Glu Lys Thr Ile Ser Lys Thr Lys Gly Gln Pro Arg Glu
    210                 215                 220

Pro Gln Val Tyr Thr Leu Pro Pro Ser Arg Glu Glu Met Thr Lys Asn
225                 230                 235                 240

Gln Val Ser Leu Thr Cys Leu Val Lys Gly Phe Tyr Pro Ser Asp Ile
                245                 250                 255

Ser Val Glu Trp Glu Ser Asn Gly Gln Pro Glu Asn Asn Tyr Lys Thr
            260                 265                 270

Thr Pro Pro Met Leu Asp Ser Asp Gly Ser Phe Phe Leu Tyr Ser Lys
        275                 280                 285

Leu Thr Val Asp Lys Ser Arg Trp Gln Gln Gly Asn Val Phe Ser Cys
    290                 295                 300

Ser Val Met His Glu Ala Leu His Asn His Tyr Thr Gln Lys Ser Leu
305                 310                 315                 320

Ser Leu Ser Pro Gly Lys
                325

<210> SEQ ID NO 101
<211> LENGTH: 106
<212> TYPE: PRT
<213> ORGANISM: Artificial Sequence
<220> FEATURE:
<223> OTHER INFORMATION: synthetic

<400> SEQUENCE: 101

Gly Gln Pro Lys Ala Asn Pro Thr Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Gly Ser Pro
        35                  40                  45

Val Lys Ala Gly Val Glu Thr Thr Lys Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105

<210> SEQ ID NO 102
<211> LENGTH: 106
<212> TYPE: PRT
<213> ORGANISM: Artificial Sequence
<220> FEATURE:
<223> OTHER INFORMATION: synthetic

<400> SEQUENCE: 102

```
Gly Gln Pro Lys Ala Ala Pro Ser Val Thr Leu Phe Pro Pro Ser Ser
1               5                   10                  15

Glu Glu Leu Gln Ala Asn Lys Ala Thr Leu Val Cys Leu Ile Ser Asp
            20                  25                  30

Phe Tyr Pro Gly Ala Val Thr Val Ala Trp Lys Ala Asp Ser Ser Pro
        35                  40                  45

Val Lys Ala Gly Val Glu Thr Thr Thr Pro Ser Lys Gln Ser Asn Asn
    50                  55                  60

Lys Tyr Ala Ala Ser Ser Tyr Leu Ser Leu Thr Pro Glu Gln Trp Lys
65                  70                  75                  80

Ser His Arg Ser Tyr Ser Cys Gln Val Thr His Glu Gly Ser Thr Val
                85                  90                  95

Glu Lys Thr Val Ala Pro Thr Glu Cys Ser
            100                 105
```

<210> SEQ ID NO 103
<211> LENGTH: 107
<212> TYPE: PRT
<213> ORGANISM: Artificial Sequence
<220> FEATURE:
<223> OTHER INFORMATION: synthetic

<400> SEQUENCE: 103

```
Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 104
<211> LENGTH: 162
<212> TYPE: PRT
<213> ORGANISM: Artificial Sequence
<220> FEATURE:
<223> OTHER INFORMATION: synthetic

<400> SEQUENCE: 104

```
Thr His Arg Thr Gly Leu Arg Ser Pro Asp Ile Pro Gln Asp Trp Val
1               5                   10                  15

Ser Phe Leu Arg Ser Phe Gly Gln Leu Thr Leu Cys Pro Arg Asn Gly
            20                  25                  30
```

-continued

```
Thr Val Thr Gly Lys Trp Arg Gly Ser His Val Val Gly Leu Leu Thr
        35              40              45

Thr Leu Asn Phe Gly Asp Gly Pro Asp Arg Asn Lys Thr Arg Thr Phe
    50              55              60

Gln Ala Thr Val Leu Gly Ser Gln Met Gly Leu Lys Gly Ser Ser Ala
65              70              75              80

Gly Gln Leu Val Leu Ile Thr Ala Arg Val Thr Thr Glu Arg Thr Ala
                85              90              95

Gly Thr Cys Leu Tyr Phe Ser Ala Val Pro Gly Ile Leu Pro Ser Ser
            100             105             110

Gln Pro Pro Ile Ser Cys Ser Glu Glu Gly Ala Gly Asn Ala Thr Leu
        115             120             125

Ser Pro Arg Met Gly Glu Glu Cys Val Ser Val Trp Ser His Glu Gly
    130             135             140

Leu Val Leu Thr Lys Leu Leu Thr Ser Glu Glu Leu Ala Leu Cys Gly
145             150             155             160

Ser Arg
```